(12) United States Patent
Chiang et al.

(10) Patent No.: US 9,877,699 B2
(45) Date of Patent: Jan. 30, 2018

(54) TABLET ULTRASOUND SYSTEM

(71) Applicant: Teratech Corporation, Burlington, MA (US)

(72) Inventors: Alice M. Chiang, Weston, MA (US); William M. Wong, Milton, MA (US); Noah Berger, Sudbury, MA (US)

(73) Assignee: Teratech Corporation, Burlington, MA (US)

( * ) Notice: Subject to any disclaimer, the term of this patent is extended or adjusted under 35 U.S.C. 154(b) by 0 days.

(21) Appl. No.: 14/037,106

(22) Filed: Sep. 25, 2013

(65) Prior Publication Data

US 2014/0121524 A1   May 1, 2014

Related U.S. Application Data

(63) Continuation-in-part of application No. PCT/US2013/033941, filed on Mar. 26, 2013, which
(Continued)

(51) Int. Cl.
*A61B 8/00* (2006.01)
*A61B 8/08* (2006.01)
(Continued)

(52) U.S. Cl.
CPC .......... *A61B 8/4427* (2013.01); *A61B 8/0841* (2013.01); *A61B 8/0883* (2013.01);
(Continued)

(58) Field of Classification Search
CPC ...... G06F 3/0488; G06F 3/041; G06F 3/0486; G06F 3/04886; G06F 19/3406;
(Continued)

(56) References Cited

U.S. PATENT DOCUMENTS 6,063,030 A    5/2000  Vara et al.
6,106,472 A    8/2000  Chiang et al.
(Continued)

FOREIGN PATENT DOCUMENTS

CN    102525556 A    7/2012
CN    102626324 A    8/2012
(Continued)

OTHER PUBLICATIONS

Butrus, T. Khuri-Yakub, et al., "Capacitive Micromachined Ultrasonic Transducers for Medical Imaging and Therapy; CMUTS for Medical Imaging and Therapy," Journal of Micromechanics and Microengineering, Institute of Physics Publishing, vol. 21, No. 5, Apr. 28, 2013, p. 54004 (XP020190354).
(Continued)

*Primary Examiner* — Sanjay Cattungal
(74) *Attorney, Agent, or Firm* — McCarter & English, LLP

(57) ABSTRACT

Exemplary embodiments provide systems and methods for portable medical ultrasound imaging. Preferred embodiments utilize a tablet touchscreen display operative to control imaging and display operations without the need for using traditional keyboards or controls. Certain embodiments provide ultrasound imaging system in which the scan head includes a beamformer circuit that performs far field sub array beamforming or includes a sparse array selecting circuit that actuates selected elements. Exemplary embodiments also provide an ultrasound engine circuit board including one or more multi-chip modules, and a portable medical ultrasound imaging system including an ultrasound engine circuit board with one or more multi-chip modules. Exemplary embodiments also provide methods for using a hierarchical two-stage or three-stage beamforming system,
(Continued)

three dimensional ultrasound images which can be generated in real-time.

59 Claims, 56 Drawing Sheets

Related U.S. Application Data is a continuation-in-part of application No. 13/838,694, filed on Mar. 15, 2013.

(60) Provisional application No. 61/615,627, filed on Mar. 26, 2012, provisional application No. 61/704,254, filed on Sep. 21, 2012.

(51) Int. Cl.
| | |
|---|---|
| *G01S 7/52* | (2006.01) |
| *G06F 3/0488* | (2013.01) |
| *H01L 25/065* | (2006.01) |
| *G06F 19/00* | (2011.01) |
| *A61B 8/13* | (2006.01) |
| *A61B 8/06* | (2006.01) |
| *G01S 15/89* | (2006.01) |

(52) U.S. Cl.
CPC .......... *A61B 8/0891* (2013.01); *A61B 8/4405* (2013.01); *A61B 8/4477* (2013.01); *A61B 8/4483* (2013.01); *A61B 8/461* (2013.01); *A61B 8/462* (2013.01); *A61B 8/463* (2013.01); *A61B 8/465* (2013.01); *A61B 8/467* (2013.01); *A61B 8/468* (2013.01); *A61B 8/469* (2013.01); *A61B 8/5207* (2013.01); *A61B 8/56* (2013.01); *A61B 8/565* (2013.01); *G01S 7/52019* (2013.01); *G01S 7/52023* (2013.01); *G01S 7/52074* (2013.01); *G01S 7/52082* (2013.01); *G01S 7/52084* (2013.01); *G01S 15/8925* (2013.01); *G06F 3/0488* (2013.01); *G06F 3/04883* (2013.01); *G06F 19/321* (2013.01); *G06F 19/3406* (2013.01); *H01L 25/0657* (2013.01); *A61B 8/06* (2013.01); *A61B 8/08* (2013.01); *A61B 8/13* (2013.01); *A61B 8/4444* (2013.01); *A61B 8/54* (2013.01); *G01S 15/8979* (2013.01); *H01L 2224/32145* (2013.01); *H01L 2224/32245* (2013.01); *H01L 2224/48091* (2013.01); *H01L 2224/73265* (2013.01); *H01L 2924/181* (2013.01)

(58) Field of Classification Search
CPC . G06F 19/321; G06F 3/04883; A61B 8/4427; A61B 8/565; A61B 8/468; A61B 8/469; A61B 8/465; A61B 8/462; A61B 8/56; A61B 8/463; A61B 8/467; A61B 8/461; A61B 8/5207; A61B 8/0883; A61B 8/0891; A61B 8/4483; A61B 8/4405; A61B 8/4477; A61B 8/08; H01L 25/0657; H01L 2924/181; H01L 2224/32245; H01L 2224/48091; H01L 2224/32145; H01L 2224/73265; G01S 15/8925; G01S 7/52023; G01S 7/5201; G01S 7/52074; G01S 7/52084
USPC ................................................ 600/437–469
See application file for complete search history.

(56) References Cited

U.S. PATENT DOCUMENTS

| | | | |
|---|---|---|---|
| 6,447,451 B1 | 9/2002 | Wing et al. | |
| 6,468,212 B1 | 10/2002 | Scott et al. | |
| 6,530,887 B1 | 3/2003 | Gilbert et al. | |
| 6,575,908 B2 | 6/2003 | Barnes et al. | |
| 6,669,633 B2 | 12/2003 | Brodsky et al. | |
| 8,435,183 B2 | 5/2013 | Barnes et al. | |
| 9,033,879 B2 | 5/2015 | Urness et al. | |
| 9,072,471 B2 | 7/2015 | Kato et al. | |
| 9,113,825 B2 | 8/2015 | Chaggares et al. | |
| 9,301,730 B2 | 4/2016 | Poland | |
| 9,314,225 B2 * | 4/2016 | Steen ................... A61B 8/5207 |
| 9,504,448 B2 | 11/2016 | Cheng et al. | |
| 2003/0078501 A1 | 4/2003 | Barnes et al. | |
| 2003/0139664 A1 * | 7/2003 | Hunt ....................... A61B 8/00 600/407 |
| 2003/0195418 A1 | 10/2003 | Barnes et al. | |
| 2003/0212327 A1 | 11/2003 | Wang et al. | |
| 2004/0015079 A1 | 1/2004 | Berger et al. | |
| 2004/0152982 A1 | 8/2004 | Hwang et al. | |
| 2004/0152986 A1 | 8/2004 | Fidel et al. | |
| 2004/0158154 A1 * | 8/2004 | Hanafy ................ A61B 8/4483 600/446 |
| 2006/0020204 A1 | 1/2006 | Serra et al. | |
| 2006/0020206 A1 | 1/2006 | Serra et al. | |
| 2007/0139873 A1 | 6/2007 | Thomas et al. | |
| 2008/0161686 A1 | 7/2008 | Halmann | |
| 2008/0215982 A1 | 9/2008 | Washburn et al. | |
| 2009/0054781 A1 | 2/2009 | Stonefield et al. | |
| 2009/0177086 A1 | 7/2009 | Steen | |
| 2009/0198132 A1 | 8/2009 | Pelissier et al. | |
| 2009/0275835 A1 * | 11/2009 | Hwang ............... G01S 7/52079 600/443 |
| 2010/0022890 A1 | 1/2010 | Fukukita et al. | |
| 2010/0094132 A1 | 4/2010 | Hansen et al. | |
| 2010/0145195 A1 | 6/2010 | Hyun | |
| 2010/0217123 A1 | 8/2010 | Eran et al. | |
| 2010/0217128 A1 | 8/2010 | Betts | |
| 2010/0305444 A1 | 12/2010 | Fujii et al. | |
| 2011/0050594 A1 * | 3/2011 | Kim ..................... G06F 3/04847 345/173 |
| 2011/0125022 A1 | 5/2011 | Lazebnik | |
| 2011/0237948 A1 | 9/2011 | Corn | |
| 2011/0313292 A1 | 12/2011 | Kwak et al. | |
| 2012/0010508 A1 | 1/2012 | Sokulin et al. | |
| 2012/0053463 A1 | 3/2012 | Yoo | |
| 2012/0065513 A1 | 3/2012 | Lee | |
| 2012/0078108 A1 | 3/2012 | Kim et al. | |
| 2012/0089024 A1 | 4/2012 | Hong | |
| 2012/0095342 A1 | 4/2012 | Lee | |
| 2012/0101378 A1 | 4/2012 | Lee | |
| 2012/0108962 A1 | 5/2012 | Yoon | |
| 2012/0108964 A1 | 5/2012 | Lee et al. | |
| 2012/0112605 A1 | 5/2012 | Kim | |
| 2012/0130244 A1 | 5/2012 | Kim | |
| 2012/0133601 A1 * | 5/2012 | Marshall ............... G06F 19/321 345/173 |
| 2012/0136252 A1 | 5/2012 | Cho | |
| 2012/0136254 A1 | 5/2012 | Kim | |
| 2012/0157836 A1 | 6/2012 | Kim | |
| 2012/0157847 A1 | 6/2012 | Kim | |
| 2012/0157848 A1 | 6/2012 | Kim | |
| 2012/0184849 A1 | 7/2012 | Sandstrom et al. | |
| 2012/0190984 A1 | 7/2012 | Kim et al. | |
| 2012/0215108 A1 | 8/2012 | Park et al. | |
| 2012/0220873 A1 | 8/2012 | Hyun | |
| 2012/0232399 A1 | 9/2012 | Lee | |
| 2012/0265027 A1 | 10/2012 | Lee et al. | |
| 2012/0265074 A1 | 10/2012 | Na et al. | |
| 2012/0302883 A1 | 11/2012 | Kong et al. | |
| 2012/0316444 A1 | 12/2012 | Shim et al. | |
| 2013/0018265 A1 | 1/2013 | Kim et al. | |
| 2013/0019193 A1 * | 1/2013 | Rhee ..................... G06F 3/0486 715/769 |
| 2013/0072797 A1 | 3/2013 | Lee | |
| 2013/0079627 A1 | 3/2013 | Lee | |
| 2013/0144169 A1 | 6/2013 | Lee et al. | |
| 2013/0144194 A1 | 6/2013 | Ahn et al. | |
| 2013/0184578 A1 | 7/2013 | Lee et al. | |
| 2013/0202169 A1 | 8/2013 | Lee et al. | |
| 2013/0202174 A1 | 8/2013 | Lee | |
| 2013/0218014 A1 | 8/2013 | Shim et al. | |

(56) References Cited

U.S. PATENT DOCUMENTS

| | | | |
|---|---|---|---|
| 2013/0218024 A1* | 8/2013 | Boctor | A61B 34/20 600/476 |
| 2013/0226001 A1 | 8/2013 | Steen et al. | |
| 2013/0226004 A1 | 8/2013 | Lee | |
| 2013/0237824 A1 | 9/2013 | Kim | |
| 2013/0237828 A1 | 9/2013 | Lee et al. | |
| 2013/0239052 A1 | 9/2013 | Moody et al. | |
| 2013/0245449 A1 | 9/2013 | Barnes et al. | |
| 2013/0253316 A1 | 9/2013 | Choi | |
| 2013/0253323 A1 | 9/2013 | Kim | |
| 2013/0261434 A1 | 10/2013 | Kim et al. | |
| 2013/0261448 A1 | 10/2013 | Hyun et al. | |
| 2013/0261459 A1 | 10/2013 | Na et al. | |
| 2013/0324850 A1 | 12/2013 | Petruzzelli et al. | |
| 2013/0328810 A1* | 12/2013 | Li | G06F 3/043 345/173 |
| 2013/0331694 A1 | 12/2013 | Barnes et al. | |
| 2014/0009686 A1* | 1/2014 | Segal | H04N 5/2222 348/722 |
| 2014/0111451 A1* | 4/2014 | Park | G06F 3/0488 345/173 |
| 2014/0114190 A1 | 4/2014 | Chiang et al. | |
| 2014/0164965 A1* | 6/2014 | Lee | G06F 3/04842 715/765 |
| 2014/0180111 A1* | 6/2014 | Gopinathan | A61B 8/565 600/447 |
| 2014/0187946 A1 | 7/2014 | Miller et al. | |
| 2014/0194742 A1 | 7/2014 | Sundaran Baby Sarojam et al. | |
| 2014/0200456 A1* | 7/2014 | Owen | A61B 8/4427 600/447 |
| 2015/0182197 A1 | 7/2015 | Willems et al. | |
| 2015/0238168 A1 | 8/2015 | Poland | |
| 2016/0135786 A1 | 5/2016 | Mullen et al. | |
| 2016/0174937 A1 | 6/2016 | Bakshi et al. | |
| 2016/0228091 A1 | 8/2016 | Chiang et al. | |
| 2017/0055951 A1 | 3/2017 | Messina et al. | |

FOREIGN PATENT DOCUMENTS

| | | |
|---|---|---|
| CN | 102636787 A | 8/2012 |
| CN | 102872542 A | 1/2013 |
| CN | 102930170 A | 2/2013 |
| CN | 102940507 A | 2/2013 |
| CN | 102988043 A | 3/2013 |
| CN | 103140175 A | 6/2013 |
| CN | 103876781 A | 6/2014 |
| EP | 2422705 A1 | 2/2012 |
| EP | 2425784 A1 | 3/2012 |
| EP | 2453256 A2 | 5/2012 |
| EP | 2455753 A2 | 5/2012 |
| EP | 2468191 A1 | 6/2012 |
| EP | 2575628 A2 | 4/2013 |
| EP | 2599442 A1 | 6/2013 |
| EP | 2605035 A2 | 6/2013 |
| EP | 2637166 A2 | 9/2013 |
| JP | H11-508461 A | 7/1999 |
| JP | 2004-530463 A | 10/2004 |
| JP | 2008-515583 A | 5/2008 |
| JP | 2009-183720 A | 8/2009 |
| JP | 2009-240779 A | 10/2009 |
| JP | 2010-131396 A | 6/2010 |
| JP | 2011-87949 A | 5/2011 |
| JP | 2012101075 A | 5/2012 |
| JP | 2013043082 A | 3/2013 |
| KR | 20120043642 A | 5/2012 |
| KR | 20120047785 A | 5/2012 |
| KR | 20120071319 A | 7/2012 |
| KR | 20120097324 A | 9/2012 |
| KR | 20120117714 A | 10/2012 |
| KR | 20120137206 A | 12/2012 |
| KR | 20120138478 A | 12/2012 |
| KR | 20130011793 A | 1/2013 |
| KR | 20130012501 A | 2/2013 |
| KR | 20130012844 A | 2/2013 |
| KR | 20130020035 A | 2/2013 |
| KR | 20130020054 A | 2/2013 |
| KR | 20130020371 A | 2/2013 |
| KR | 20130022249 A | 3/2013 |
| KR | 20130026041 A | 3/2013 |
| KR | 20130030663 A | 3/2013 |
| KR | 20130033717 A | 4/2013 |
| KR | 20130036327 A | 4/2013 |
| KR | 101269459 B1 | 5/2013 |
| KR | 20130043702 A | 5/2013 |
| KR | 20130054013 A | 5/2013 |
| KR | 20130056676 A | 5/2013 |
| KR | 101273585 B1 | 6/2013 |
| KR | 20130059307 A | 6/2013 |
| KR | 20130060007 A | 6/2013 |
| KR | 20130066821 A | 6/2013 |
| KR | 20130074398 A | 7/2013 |
| KR | 20130074399 A | 7/2013 |
| KR | 20130075458 A | 7/2013 |
| KR | 20130075465 A | 7/2013 |
| KR | 20130075472 A | 7/2013 |
| KR | 20130075477 A | 7/2013 |
| KR | 20130075481 A | 7/2013 |
| KR | 20130075486 A | 7/2013 |
| KR | 20130076031 A | 7/2013 |
| KR | 20130076042 A | 7/2013 |
| KR | 20130076054 A | 7/2013 |
| KR | 20130076064 A | 7/2013 |
| KR | 20130076071 A | 7/2013 |
| KR | 20130076404 A | 7/2013 |
| KR | 20130076428 A | 7/2013 |
| KR | 20130077118 A | 7/2013 |
| KR | 20130077121 A | 7/2013 |
| KR | 20130077406 A | 7/2013 |
| KR | 20130078935 A | 7/2013 |
| KR | 20130078972 A | 7/2013 |
| KR | 20130080640 A | 7/2013 |
| KR | 20130081067 A | 7/2013 |
| KR | 20130081626 A | 7/2013 |
| KR | 20130081684 A | 7/2013 |
| KR | 20130082267 A | 7/2013 |
| KR | 20130083725 A | 7/2013 |
| KR | 20130084049 A | 7/2013 |
| KR | 20130087291 A | 8/2013 |
| KR | 20130087478 | 8/2013 |
| KR | 20130088478 A | 8/2013 |
| KR | 20130089037 A | 8/2013 |
| KR | 20130090038 A | 8/2013 |
| KR | 20130094671 A | 8/2013 |
| KR | 20130095160 A | 8/2013 |
| KR | 20130095236 A | 8/2013 |
| KR | 20130095505 A | 8/2013 |
| WO | 2002/068992 A2 | 9/2002 |
| WO | 2005/053664 A2 | 6/2005 |
| WO | 2006/040697 A1 | 4/2006 |
| WO | 2008/069021 A1 | 6/2008 |
| WO | 2010/042282 A1 | 4/2010 |
| WO | 2010/051587 A1 | 5/2010 |
| WO | 2012091518 A2 | 7/2012 |
| WO | 2012141550 A2 | 10/2012 |
| WO | 2013095032 A1 | 6/2013 |
| WO | 2013122320 A1 | 8/2013 |
| WO | 2015/114484 A1 | 8/2015 |
| WO | 2016/001865 A1 | 1/2016 |
| WO | 2017/013511 A1 | 1/2017 |

OTHER PUBLICATIONS

International Search Report and Written Opinion of the International Searching Authority on International application No. PCT/US2013/0333941, dated Oct. 8, 2013.

International Report on Patentability by the International Bureau of WIPO for International Application No. PCT/US2013/033941 dated Oct. 1, 2014. (24 pages).

Invitation to Pay Additional Fees including Communication Relating to the Results of the Partial International Search by the International Searching Authority for International Application No. PCT/US2014/057516 dated Jan. 13, 2015. (6 pages).

(56) References Cited

OTHER PUBLICATIONS

U.S. Appl. No. 13/838,694, filed Mar. 15, 2013.
U.S. Appl. No. 15/025,058, filed Mar. 25, 2016.
GE Healthcare Venue 40 Basic User Manual, Technical Publications Direction 5265930-100, Rev. 5. 288 pages (2008-2010).
NanoMaxx Ultrasound System—Sonosite—User Guide.

* cited by examiner

Tap

Flick

Pinch

Rotate

Flick

Drag

Rotate

Press

Double Tap

Press & Tag

Spread

Palm

TABLET ULTRASOUND SYSTEM

CROSS REFERENCE TO RELATED APPLICATIONS

This application is a continuation-in-part of PCT Application PCT/US2013/033941 filed Mar. 26, 2013, and of U.S. application Ser. No. 13/838,694 filed Mar. 15, 2013, and claims priority to U.S. Provisional Application No. 61/615,627, filed Mar. 26, 2012 and U.S. Provisional Application No. 61/704,254, filed Sep. 21, 2012, these applications being incorporated herein by reference in their entirety.

BACKGROUND OF THE INVENTION

Medical ultrasound imaging has become an industry standard for many medical imaging applications. In recent years, there has been an increasing need for medical ultrasound imaging equipment that is portable to allow medical personnel to easily transport the equipment to and from hospital and/or field locations, and more user-friendly to accommodate medical personnel who may possess a range of skill levels.

Conventional medical ultrasound imaging equipment typically includes at least one ultrasound probe/transducer, a keyboard and/or a knob, a computer, and a display. In a typical mode of operation, the ultrasound probe/transducer generates ultrasound waves that can penetrate tissue to different depths based on frequency level, and receives ultrasound waves reflected back from the tissue. Further, medical personnel can enter system inputs to the computer via the keyboard and/or the knob, and view ultrasound images of tissue structures on the display.

However, conventional medical ultrasound imaging equipment that employ such keyboards and/or knobs can be bulky, and therefore may not be amenable to portable use in hospital and/or field locations. Moreover, because such keyboards and/or knobs typically have uneven surfaces, they can be difficult to keep clean in hospital and/or field environments, where maintenance of a sterile field can be crucial to patient health. Some conventional medical ultrasound imaging equipment have incorporated touch screen technology to provide a partial user input interface. However, conventional medical ultrasound imaging equipment that employ such touch screen technology generally provide only limited touch screen functionality in conjunction with a traditional keyboard and/or knob, and can therefore not only be difficult to keep clean, but also complicated to use.

SUMMARY OF THE INVENTION

In accordance with the present application, systems and methods of medical ultrasound imaging are disclosed. The presently disclosed systems and methods of medical ultrasound imaging employ medical ultrasound imaging equipment that includes a handheld housing in a tablet form factor, and a touch screen display disposed on a front panel of the housing. The touch screen display includes a multi-touch touchscreen that can recognize and distinguish one or more single, multiple, and/or simultaneous touches on a surface of the touch screen display, thereby allowing the use of gestures, ranging from simple single point gestures to complex multipoint moving gestures, as user inputs to the medical ultrasound imaging equipment.

In accordance with one aspect, exemplary medical ultrasound imaging system includes a housing having a front panel and a rear panel rigidly mounted to each other in parallel planes, a touch screen display, a computer having at least one processor and at least one memory, an ultrasound beamforming system, and a battery. The housing of the medical ultrasound imaging equipment is implemented in a tablet form factor. The touch screen display is disposed on the front panel of the housing, and includes a multi-touch LCD touch screen that can recognize and distinguish one or more single, multiple, and/or simultaneous touches or gestures on a surface of the touch screen display. The computer, the ultrasound beamforming system or engine, and the battery are operatively disposed within the housing. The medical ultrasound imaging equipment can use a Firewire connection operatively connected between the computer and the ultrasound engine within the housing and a probe connector having a probe attach/detach lever to facilitate the connection of at least one ultrasound probe/transducer. In addition, the exemplary medical ultrasound imaging system includes an I/O port connector and a DC power input.

In an exemplary mode of operation, medical personnel can employ simple single point gestures and/or more complex multipoint gestures as user inputs to the multi-touch LCD touch screen for controlling operational modes and/or functions of the exemplary medical ultrasound imaging equipment. Such single point/multipoint gestures can correspond to single and/or multipoint touch events that are mapped to one or more predetermined operations that can be performed by the computer and/or the ultrasound engine. Medical personnel can make such single point/multipoint gestures by various finger, palm, and/or stylus motions on the surface of the touch screen display. The multi-touch LCD touch screen receives the single point/multipoint gestures as user inputs, and provides the user inputs to the computer, which executes, using the processor, program instructions stored in the memory to carry out the predetermined operations associated with the single point/multipoint gestures, at least at some times, in conjunction with the ultrasound engine. Such single point/multipoint gestures on the surface of the touch screen display can include, but are not limited to, a tap gesture, a pinch gesture, a flick gesture, a rotate gesture, a double tap gesture, a spread gesture, a drag gesture, a press gesture, a press and drag gesture, and a palm gesture. In contrast to existing ultrasound systems that rely on numerous control features operated by mechanical switching, keyboard elements, or touchpad trackball interface, preferred embodiments of the present invention employ a single on/off switch. All other operations have been implemented using touchscreen controls. Moreover, the preferred embodiments employ a capacitive touchscreen display that is sufficiently sensitive to detect touch gestures actuated by bare fingers of the user as well as gloved fingers of the user. Often medical personnel must wear sterilized plastic gloves during medical procedures. Consequently, it is highly desirable to provide a portable ultrasound device that can be used by gloved hands; however, this has previously prevented the use of touchscreen display control functions in ultrasound systems for many applications requiring sterile precautions. Preferred embodiments of the present invention provide control of all ultrasound imaging operations by gloved personnel on the touchscreen display using the programmed touch gestures.

In accordance with an exemplary aspect, at least one flick gesture may be employed to control the depth of tissue penetration of ultrasound waves generated by the ultrasound probe/transducer. For example, a single flick gesture in the "up" direction on the touch screen display surface can increase the penetration depth by one (1) centimeter or any other suitable amount, and a single flick gesture in the "down" direction on the touch screen display surface can decrease the penetration depth by one (1) centimeter or any other suitable amount. Further, a drag gesture in the "up" or "down" direction on the touch screen display surface can increase or decrease the penetration depth in multiples of one (1) centimeter or any other suitable amount. Additional operational modes and/or functions controlled by specific single point/multipoint gestures on the touch screen display surface can include, but are not limited to, freeze/store operations, 2-dimensional mode operations, gain control, color control, split screen control, PW imaging control, cine/time-series image clip scrolling control, zoom and pan control, full screen control, Doppler and 2-dimensional beam steering control, and/or body marking control. At least some of the operational modes and/or functions of the exemplary medical ultrasound imaging equipment can be controlled by one or more touch controls implemented on the touch screen display in which beamforming parameters can be reset by moving touch gestures. Medical personnel can provide one or more specific single point/multipoint gestures as user inputs for specifying at least one selected subset of the touch controls to be implemented, as required and/or desired, on the touch screen display. A larger number of touchscreen controls enable greater functionality when operating in full screen mode when a few or more virtual buttons or icons are available for use.

In accordance with another exemplary aspect, a press gesture can be employed inside a region of the touch screen display, and, in response to the press gesture, a virtual window can be provided on the touch screen display for displaying at least a magnified portion of an ultrasound image displayed on the touch screen display. In accordance with still another exemplary aspect, a press and drag gesture can be employed inside the region of the touch screen display, and, in response to the press and drag gesture, a predetermined feature of the ultrasound image can be traced. Further, a tap gesture can be employed inside the region of the touch screen display, substantially simultaneously with a portion of the press and drag gesture, and, in response to the tap gesture, the tracing of the predetermined feature of the ultrasound image can be completed. These operations can operate in different regions of a single display format, so that a moving gesture within a region of interest within the image, for example, may perform a different function than the same gesture executed within the image but outside the region of interest.

By providing medical ultrasound imaging equipment with a multi-touch touchscreen, medical personnel can control the equipment using simple single point gestures and/or more complex multipoint gestures, without the need of a traditional keyboard or knob. Because the multi-touch touch screen obviates the need for a traditional keyboard or knob, such medical ultrasound imaging equipment is easier to keep clean in hospital and/or field environments, provides an intuitive user friendly interface, while providing fully functional operations. Moreover, by providing such medical ultrasound imaging equipment in a tablet form factor, medical personnel can easily transport the equipment between hospital and/or field locations.

Certain exemplary embodiments provide a multi-chip module for an ultrasound engine of a portable medical ultrasound imaging system, in which a transmit/receive (TR) chip, a pre-amp/time gain compensation (TGC) chip and a beamformer chip are assembled in a vertically stacked configuration. The transmission circuit provides high voltage electrical driving pulses to the transducer elements to generate a transmit beam. As the transmit chip operates at voltages greater than 80V, a CMOS process utilizing a 1 micron design rule has been utilized for the transmit chip and a submicron design rule has been utilized for the low-voltage receiving circuits (less than 5V).

Preferred embodiments of the present invention utilize a submicron process to provide integrated circuits with sub-circuits operating at a plurality of voltages, for example, 2.5V, 5V and 60V or higher. These features can be used in conjunction with a bi-plane transducer probe in accordance with certain preferred embodiments of the invention.

Thus, a single IC chip can be utilized that incorporates high voltage transmission, low voltage amplifier/TGC and low voltage beamforming circuits in a single chip. Using a 0.25 micron design rule, this mixed signal circuit can accommodate beamforming of 32 transducer channels in a chip area less than 0.7×0.7 (0.49) cm$^2$. Thus, 128 channels can be processed using four 32 channel chips in a total circuit board area of less than 1.5×1.5 (2.25) cm$^2$.

The term "multi-chip module," as used herein, refers to an electronic package in which multiple integrated circuits (IC) are packaged with a unifying substrate, facilitating their use as a single component, i.e., as a higher processing capacity IC packaged in a much smaller volume. Each IC can comprise a circuit fabricated in a thinned semiconductor wafer. Exemplary embodiments also provide an ultrasound engine including one or more such multi-chip modules, and a portable medical ultrasound imaging system including an ultrasound engine circuit board with one or more multi-chip modules. Exemplary embodiments also provide methods for fabricating and assembling multi-chip modules as taught herein. Vertically stacking the TR chip, the pre-amp/TGC chip, and the beamformer chip on a circuit board minimizes the packaging size (e.g., the length and width) and the footprint occupied by the chips on the circuit board.

The TR chip, the pre-amp/TGC chip, and the beamformer chip in a multi-chip module may each include multiple channels (for example, 8 channels per chip to 64 channels per chip). In certain embodiments, the high-voltage TR chip, the pre-amp/TGC chip, and the sample-interpolate receive beamformer chip may each include 8, 16, 32, 64 channels. In a preferred embodiment, each circuit in a two layer beamformer module has 32 beamformer receive channels to provide a 64 channel receiving beamformer. A second 64 channel two layer module can be used to form a 128 channel handheld tablet ultrasound device having an overall thickness of less than 2 cm. A transmit multi-chip beamformer can also be used having the same or similar channel density in each layer.

Exemplary numbers of chips vertically integrated in a multi-chip module may include, but are not limited to, two, three, four, five, six, seven, eight, and the like. In one embodiment of an ultrasound device, a single multi-chip module is provided on a circuit board of an ultrasound engine that performs ultrasound-specific operations. In other embodiments, a plurality of multi-chip modules are provided on a circuit board of an ultrasound engine. The plurality of multi-chip modules may be stacked vertically on top of one another on the circuit board of the ultrasound engine to further minimize the packaging size and the footprint of the circuit board.

Providing one or more multi-chip modules on a circuit board of an ultrasound engine achieves a high channel count while minimizing the overall packaging size and footprint. For example, a 128-channel ultrasound engine circuit board can be assembled, using multi-chip modules, within exemplary planar dimensions of about 10 cm× about 10 cm, which is a significant improvement over the much larger space requirements of conventional ultrasound circuits. A single circuit board of an ultrasound engine including one or more multi-chip modules may have 16 to 128 channels in some embodiments. In certain embodiments, a single circuit board of an ultrasound engine including one or more multi-chip modules may have 16, 32, 64, 128 or 192 channels, and the like.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which.

DETAILED DESCRIPTION

Systems and methods of medical ultrasound imaging are disclosed. The presently disclosed systems and methods of medical ultrasound imaging employ medical ultrasound imaging equipment that includes housing in a tablet form factor, and a touch screen display disposed on a front panel of the housing. The touch screen display includes a multi-touch touch screen that can recognize and distinguish one or more single, multiple, and/or simultaneous touches on a surface of the touch screen display, thereby allowing the use of gestures, ranging from simple single point gestures to complex multipoint gestures, as user inputs to the medical ultrasound imaging equipment. Further details regarding tablet ultrasound systems and operations are described in U.S. application Ser. No. 10/997,062 filed on Nov. 11, 2004, Ser. No. 10/386,360 filed Mar. 11, 2003 and U.S. Pat. No. 6,969,352, the entire contents of these patents and applications are incorporated herein by reference.

Figure 1:
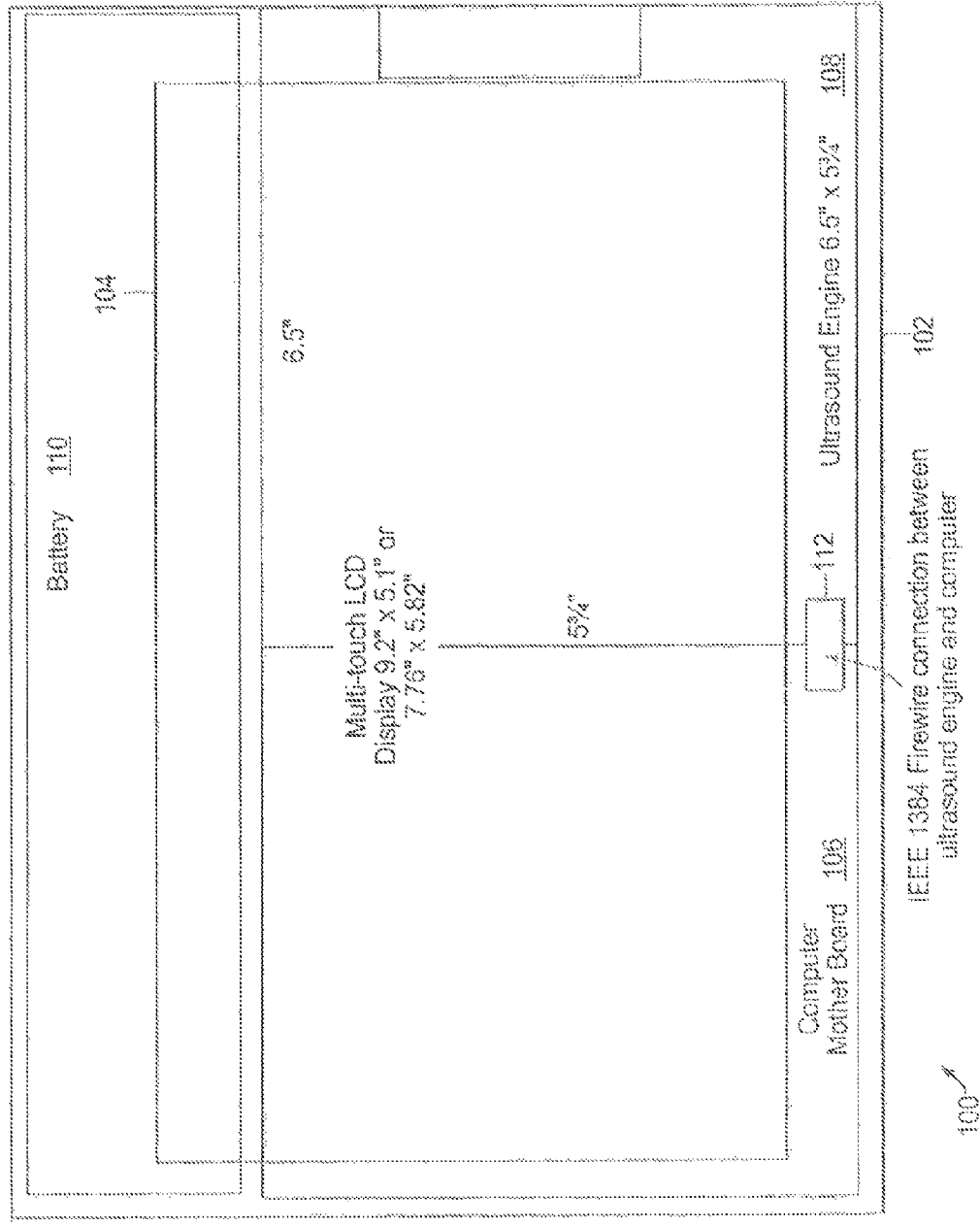
FIG. 1 is a plan view of exemplary medical ultrasound imaging equipment, in accordance with an exemplary embodiment of the present application.

FIG. 1 depicts an illustrative embodiment of exemplary medical ultrasound imaging equipment 100, in accordance with the present application. As shown in FIG. 1, the medical ultrasound imaging equipment 100 includes a housing 102, a touch screen display 104, a computer having at least one processor and at least one memory implemented on a computer motherboard 106, an ultrasound engine 108, and a battery 110. For example, the housing 102 can be implemented in a tablet form factor, or any other suitable form factor. The housing 102 has a front panel 101 and a rear panel 103. The touch screen display 104 is disposed on the front panel 101 of the housing 102, and includes a multi-touch LCD touch screen that can recognize and distinguish one or more multiple and/or simultaneous touches on a surface 105 of the touch screen display 104. The computer motherboard 106, the ultrasound engine 108, and the battery 110 are operatively disposed within the housing 102. The medical ultrasound imaging equipment 100 further includes a Firewire connection 112 (see also FIG. 2A) operatively connected between the computer motherboard 106 and the ultrasound engine 108 within the housing 102, and a probe connector 114 having a probe attach/detach lever 115 (see also FIGS. 2A and 2B) to facilitate the connection of at least one ultrasound probe/transducer. The transducer probe housing can include circuit components including a transducer array, transmit and receive circuitry, as well as beamformer and beamformer control circuits in certain preferred embodiments. In addition, the medical ultrasound imaging equipment 100 has one or more I/O port connectors 116 (see FIG. 2A), which can include, but are not limited to, one or more USB connectors, one or more SD cards, one or more network ports, one or more mini display ports, and a DC power input.

In an exemplary mode of operation, medical personnel (also referred to herein as the "user" or "users") can employ simple single point gestures and/or more complex multi-point gestures as user inputs to the multi-touch LCD touch screen of the touch screen display 104 for controlling one or more operational modes and/or functions of the medical ultrasound imaging equipment 100. Such a gesture is defined herein as a movement, a stroke, or a position of at least one finger, a stylus, and/or a palm on the surface 105 of the touch screen display 104. For example, such single point/multipoint gestures can include static or dynamic gestures, continuous or segmented gestures, and/or any other suitable gestures. A single point gesture is defined herein as a gesture that can be performed with a single touch contact point on the touch screen display 104 by a single finger, a stylus, or a palm. A multipoint gesture is defined herein as a gesture that can be performed with multiple touch contact points on the touch screen display 104 by multiple fingers, or any suitable combination of at least one finger, a stylus, and a palm. A static gesture is defined herein as a gesture that does not involve the movement of at least one finger, a stylus, or a palm on the surface 105 of the touch screen display 104. A dynamic gesture is defined herein as a gesture that involves the movement of at least one finger, a stylus, or a palm, such as the movement caused by dragging one or more fingers across the surface 105 of the touch screen display 104. A continuous gesture is defined herein as a gesture that can be performed in a single movement or stroke of at least one finger, a stylus, or a palm on the surface 105 of the touch screen display 104. A segmented gesture is defined herein as a gesture that can be performed in multiple movements or stokes of at least one finger, a stylus, or a palm on the surface 105 of the touch screen display 104.

Figure 3A:
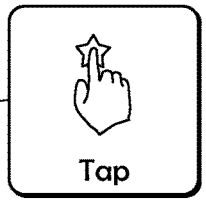
FIG. 3AA-3AL illustrates exemplary single point and multipoint gestures that can be employed as user inputs to the medical ultrasound imaging system in accordance with preferred embodiments of the invention.
Figure 3A:
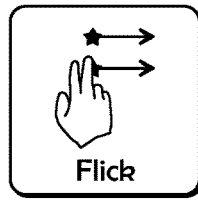
Figure 3A:
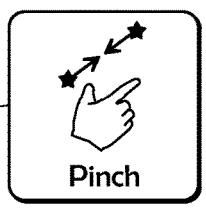
Figure 3A:
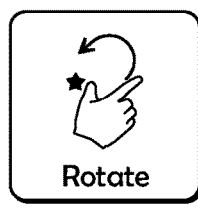
Figure 3A:
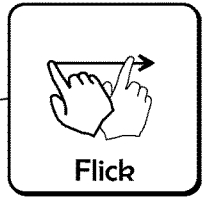
Figure 3A:
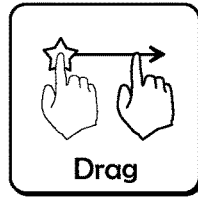
Figure 3A:
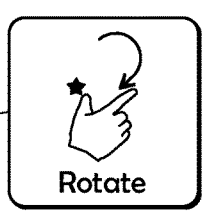
Figure 3A:
Figure 3A:
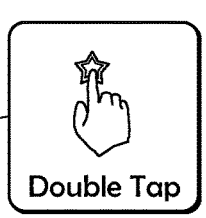
Figure 3A:
Figure 3A:
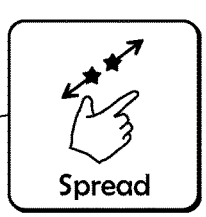
Figure 3A:

Such single point/multipoint gestures performed on the surface 105 of the touch screen display 104 can correspond to single or multipoint touch events, which are mapped to one or more predetermined operations that can be performed by the computer and/or the ultrasound engine 108. Users can make such single point/multipoint gestures by various single finger, multi-finger, stylus, and/or palm motions on the surface 105 of the touch screen display 104. The multi-touch LCD touch screen receives the single point/multipoint gestures as user inputs, and provides the user inputs to the processor, which executes program instructions stored in the memory to carry out the predetermined operations associated with the single point/multipoint gestures, at least at some times, in conjunction with the ultrasound engine 108. As shown in FIG. 3AA-3AL, such single point/multipoint gestures on the surface 105 of the touch screen display 104 can include, but are not limited to, a tap gesture 302, a pinch gesture 304, a flick gesture 306, 314, a rotate gesture 308, 316, a double tap gesture 310, a spread gesture 312, a drag gesture 318, a press gesture 320, a press and drag gesture 322, and/or a palm gesture 324. For example, such single point/multipoint gestures can be stored in at least one gesture library in the memory implemented on the computer motherboard 106. The computer program operative to control system operations can be stored on a computer readable medium and can optionally be implemented using a touch processor connected to an image processor and a control processor connected to the system beamformer. Thus beamformer delays associated with both transmission and reception can be adjusted in response to both static and moving touch gestures.

In accordance with the illustrative embodiment of FIG. 1, at least one flick gesture 306 or 314 may be employed by a user of the medical ultrasound imaging equipment 100 to control the depth of tissue penetration of ultrasound waves generated by the ultrasound probe/transducer. For example, a dynamic, continuous, flick gesture 306 or 314 in the "up" direction, or any other suitable direction, on the surface 105 of the touch screen display 104 can increase the penetration depth by one (1) centimeter, or any other suitable amount. Further, a dynamic, continuous, flick gesture 306 or 314 in the "down" direction, or any other suitable direction, on the surface 105 of the touch screen display 104 can decrease the penetration depth by one (1) centimeter, or any other suitable amount. Moreover, a dynamic, continuous, drag gesture 318 in the "up" or "down" direction, or any other suitable direction, on the surface 105 of the touch screen display 104 can increase or decrease the penetration depth in multiple centimeters, or any other suitable amounts.

Additional operational modes and/or functions controlled by specific single point/multipoint gestures on the surface 105 of the touch screen display 104 can include, but are not limited to, freeze/store operations, 2-dimensional mode operations, gain control, color control, split screen control, PW imaging control, cine/time-series image clip scrolling control, zoom and pan control, full screen display, Doppler and 2-dimensional beam steering control, and/or body marking control. At least some of the operational modes and/or functions of the medical ultrasound imaging equipment 100 can be controlled by one or more touch controls implemented on the touch screen display 104. Further, users can provide one or more specific single point/multipoint gestures as user inputs for specifying at least one selected subset of the touch controls to be implemented, as required and/or desired, on the touch screen display 104.

Figure 3B:
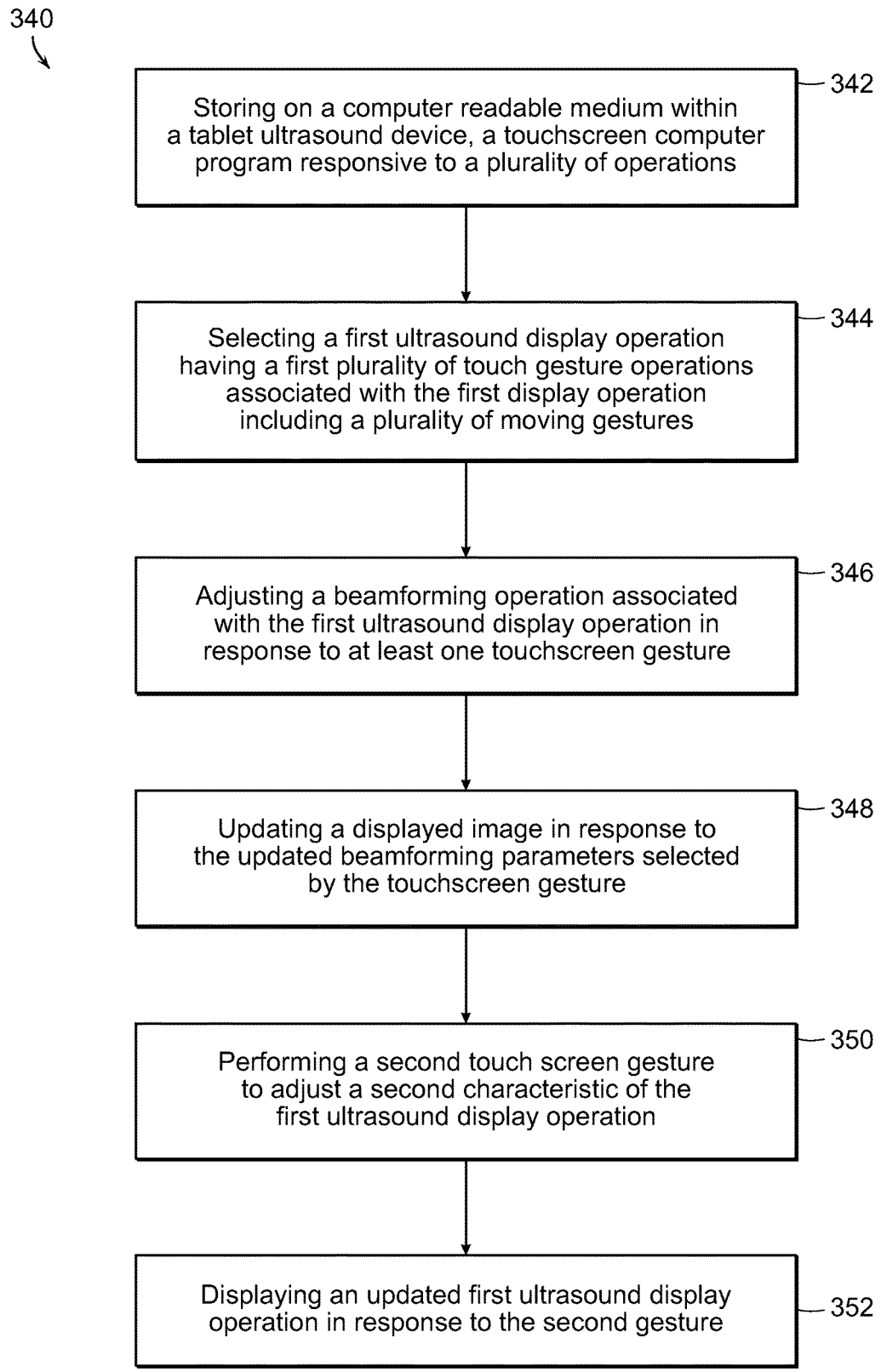
FIG. 3B illustrates a process flow diagram for operating a tablet ultrasound system in accordance with preferred embodiments of the invention.

Shown in FIG. 3B is a process sequence in which ultrasound beamforming and imaging operations 340 are controlled in response to touch gestures entered on a touchscreen. Various static and moving touch gestures have been programmed into the system such that the data processor operable to control beamforming and image processing operations 342 within the tablet device. A user can select 344 a first display operation having a first plurality of touch gestures associated therewith. Using a static or moving gesture the user can perform one of the plurality of gestures operable to control the imaging operation and can specifically select one of a plurality of gestures that can adjust beamforming parameters 346 being used to generate image data associated with the first display operation. The displayed image is updated and displayed 348 response to the updated beamforming procedure. The user can further elect to perform a different gesture having a different velocity characteristic (direction or speed or both) to adjust 350 a second characteristic of the first ultrasound display operation. The displayed image is then updated 352 based on the second gesture, which can modify imaging processing parameters or beamforming parameters. Examples of this process are described in further detail herein where changes in velocity and direction of different gestures can be associated with distinct imaging parameters of a selected display operation.

Ultrasound images of flow or tissue movement, whether color flow or spectral Doppler, are essentially obtained from measurements of movement. In ultrasound scanners, a series of pulses is transmitted to detect movement of blood. Echoes from stationary targets are the same from pulse to pulse. Echoes from moving scatterers exhibit slight differences in the time for the signal to be returned to the scanner.

Figures 3C, 3D:
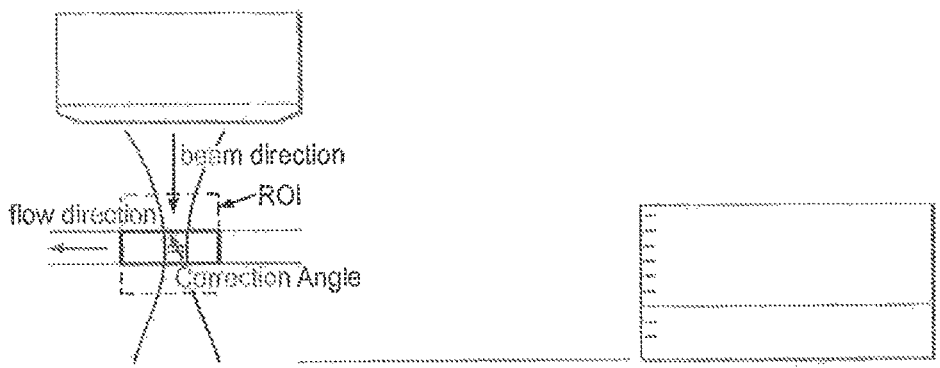
FIG. 3C-3K illustrates details of touchscreen gestures to adjust beamforming and display operation.
Figures 3E, 3F:
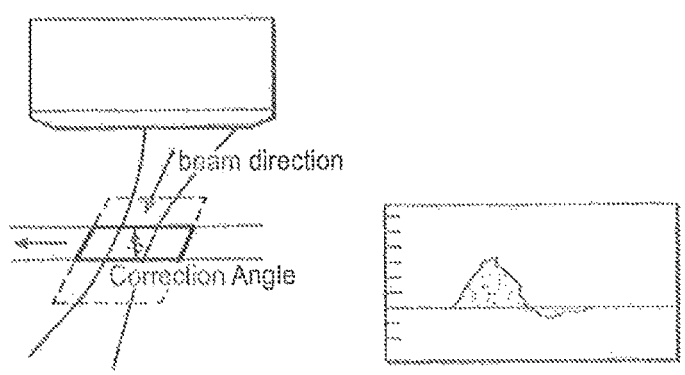
Figures 3G, 3H:
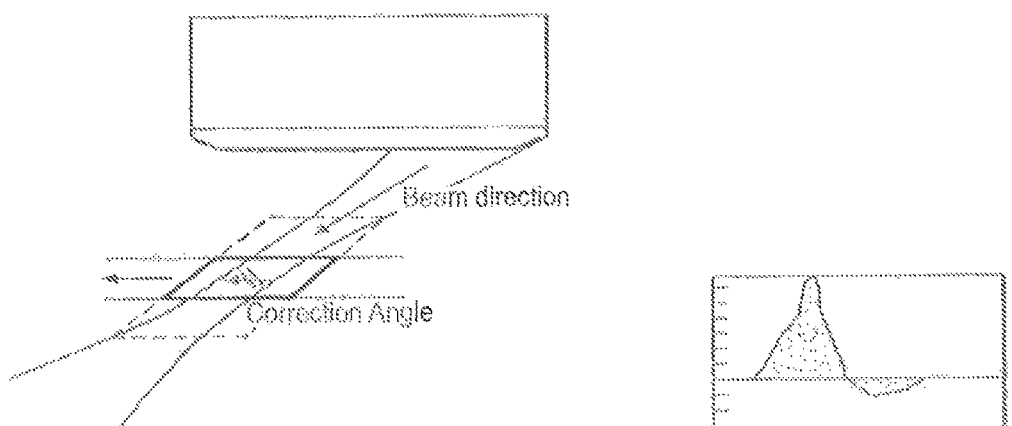

As can be seen from FIG. 3C-3H, there has to be motion in the direction of the beam; if the flow is perpendicular to the beam, there is no relative motion from pulse to pulse receive, there is no flow detected. These differences can be measured as a direct time difference or, more usually, in terms of a phase shift from which the 'Doppler frequency' is obtained. They are then processed to produce either a color flow display or a Doppler sonogram. In FIG. 3C-3D, the flow direction is perpendicular to the beam direction, no flow is measured by Pulse Wave spectral Doppler. In FIG. 3G-3H when the ultrasound beam is steered to an angle that is better aligned to the flow, a weak flow is shown in the color flow map, and in addition flow is measured by Pulse Wave Doppler. In FIG. 3H, when the ultrasound beam is steered to an angle much better aligned to the flow direction in response to a moving, the color flow map is stronger, in addition when the correction angle of the PWD is placed aligned to the flow, a strong flow is measured by the PWD.

Figure 3I:
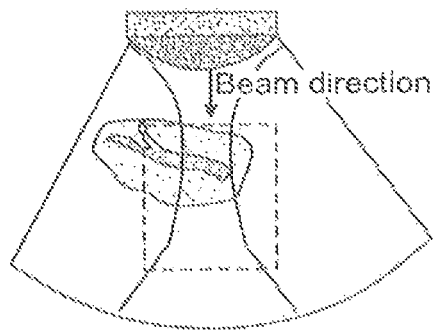
Figure 3J:
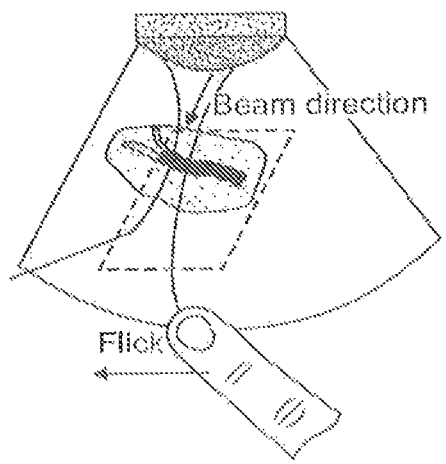

In this tablet ultrasound system, an ROI, region of interest, is also used to define the direction in response to a moving gesture of the ultrasound transmit beam. A liver image with a branch of renal flow in color flow mode is shown in FIG. 3I since the ROI is straight down from the transducer, the flow direction is almost normal to the ultrasound beam, so very week renal flow is detected. Hence, the color flow mode is used to image a renal flow in liver. As can be seen, the beam is almost normal to the flow and very weak flow is detected. A flick gesture with the finger outside of the ROI is used to steer the beam. As can be seen in FIG. 3J, the ROI is steered by resetting beamforming parameters so that the beam direction is more aligned to the flow direction, a much stronger flow within the ROI is detected. In FIG. 3J, a flick gesture with the finger outside of the ROI is used to steer the ultrasound beam into the direction more aligned to the flow direction. Stronger flow within the ROI can be seen. A panning gesture with the finger inside the ROI will move the ROI box into a position that covers the entire renal region, i.e., panning allows a translation movement of the ROI box such that the box covers the entire target area.

Figure 3K:
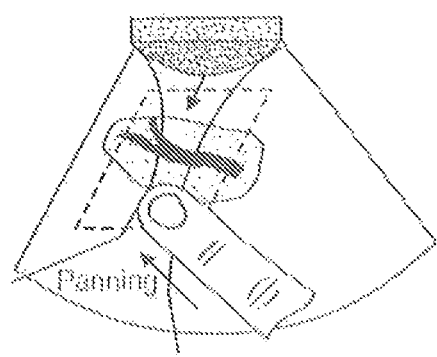

FIG. 3K demonstrates a panning gesture. With the finger inside the ROI, it can move the ROI box to any place within the image plane. In the above embodiment, it is easy to differentiate a "flick" gesture with a finger outside an "ROI" box is intended for steering a beam, and a "drag-and-move, panning" gesture with a finger inside the "ROI" is intended for moving the ROI box. However, there are applications in which no ROI as a reference region, then it is easy to see that it is difficult to differentiate a "flick" or a "panning" gesture, in this case, the touch-screen program needs to track the initial velocity or acceleration of the finger to determine it is a "flick" gesture or a "drag-and-move" gesture. Thus, the touch engine that receives data from the touchscreen sensor device is programmed to discriminate between velocity thresholds that indicate different gestures. Thus, the time, speed and direction associated with different moving gestures can have preset thresholds. Two and three finger static and moving gestures can have separate thresholds to differentiate these control operations. Note that preset displayed icons or virtual buttons can have distinct static pressure or time duration thresholds. When operated in full screen mode, the touchscreen processor, which is preferably operating on the systems central processing unit that performs other imaging operations such as scan conversion, switches off the static icons.

Figure 4A:
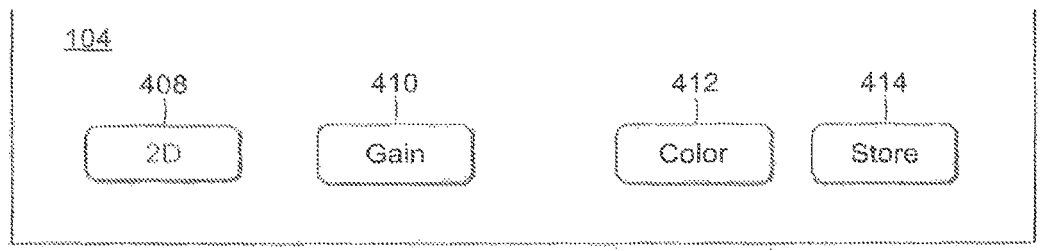
FIGS. 4A-4C illustrates exemplary subsets of touch controls that can be implemented on the medical ultrasound imaging system in accordance with preferred embodiments of the invention.
Figure 4B:
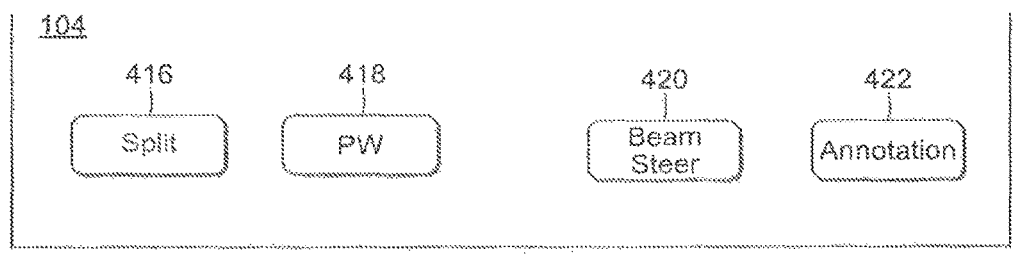
Figure 4C:
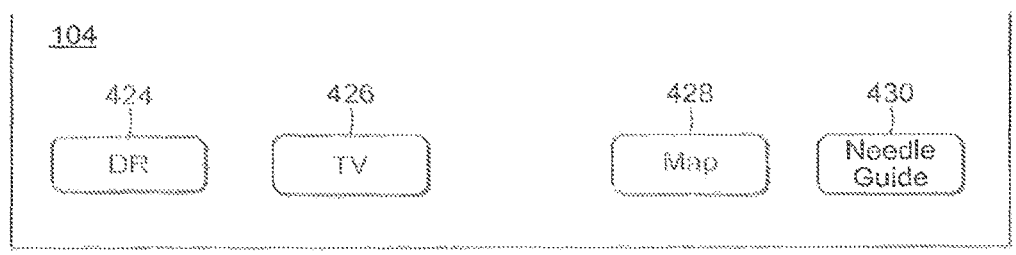

FIGS. 4A-4C depict exemplary subsets 402, 404, 406 of touch controls that can be implemented by users of the medical ultrasound imaging equipment 100 on the touch screen display 104. It is noted that any other suitable subset(s) of touch controls can be implemented, as required and/or desired, on the touch screen display 104. As shown in FIG. 4A, the subset 402 includes a touch control 408 for performing 2-dimensional (2D) mode operations, a touch control 410 for performing gain control operations, a touch control 412 for performing color control operations, and a touch control 414 for performing image/clip freeze/store operations. For example, a user can employ the press gesture 320 to actuate the touch control 408, returning the medical ultrasound imaging equipment 100 to 2D mode. Further, the user can employ the press gesture 320 against one side of the touch control 410 to decrease a gain level, and employ the press gesture 320 against another side of the touch control 410 to increase the gain level. Moreover, the user can employ the drag gesture 318 on the touch control 412 to identify ranges of densities on a 2D image, using a predetermined color code. In addition, the user can employ the press gesture 320 to actuate the touch control 414 to freeze/store a still image or to acquire a cine image clip.

As shown in FIG. 4B, the subset 404 includes a touch control 416 for performing split screen control operations, a touch control 418 for performing PW imaging control operations, a touch control 420 for performing Doppler and 2-dimensional beam steering control operations, and a touch control 422 for performing annotation operations. For example, a user can employ the press gesture 320 against the touch control 416, allowing the user to toggle between opposing sides of the split touch screen display 104 by alternately employing the tap gesture 302 on each side of the split screen. Further, the user can employ the press gesture 320 to actuate the touch control 418 and enter the PW mode, which allows (1) user control of the angle correction, (2) movement (e.g., "up" or "down") of a baseline that can be displayed on the touch screen display 104 by employing the press and drag gesture 322, and/or (3) an increase or a decrease of scale by employing the tap gesture 302 on a scale bar that can be displayed on the touch screen display 104. Moreover, the user can employ the press gesture 320 against one side of the touch control 420 to perform 2D beam steering to the "left" or any other suitable direction in increments of five (5) or any other suitable increment, and employ the press gesture 320 against another side of the touch control 420 to perform 2D beam steering to the "right" or any other suitable direction in increments of five (5) or any other suitable increment. In addition, the user can employ the tap gesture 302 on the touch control 422, allowing the user to enter annotation information via a pop-up keyboard that can be displayed on the touch screen display 104.

As shown in FIG. 4C, the subset 406 includes a touch control 424 for performing dynamic range operations, a touch control 426 for performing Teravision™ software operations, a touch control 428 for performing map operations, and a touch control 430 for performing needle guide operations. For example, a user can employ the press gesture 320 and/or the press and drag gesture 322 against the touch control 424 to control or set the dynamic range. Further, the user can employ the tap gesture 302 on the touch control 426 to choose a desired level of the Teravision™ software to be executed from the memory by the processor on the computer motherboard 106. Moreover, the user can employ the tap gesture 302 on the touch control 428 to perform a desired map operation. In addition, the user can employ the press gesture 320 against the touch control 430 to perform a desired needle guide operation.

In accordance with the present application, various measurements and/or tracings of objects (such as organs, tissues, etc.) displayed as ultrasound images on the touch screen display 104 of the medical ultrasound imaging equipment 100 (see FIG. 1) can be performed, using single point/multipoint gestures on the surface 105 of the touch screen display 104. The user can perform such measurements and/or tracings of objects directly on an original ultrasound image of the displayed object, on a magnified version of the ultrasound image of the displayed object, and/or on a magnified portion of the ultrasound image within a virtual window 506 (see FIGS. 5C and 5D) on the touch screen display 104.

Figure 5A:
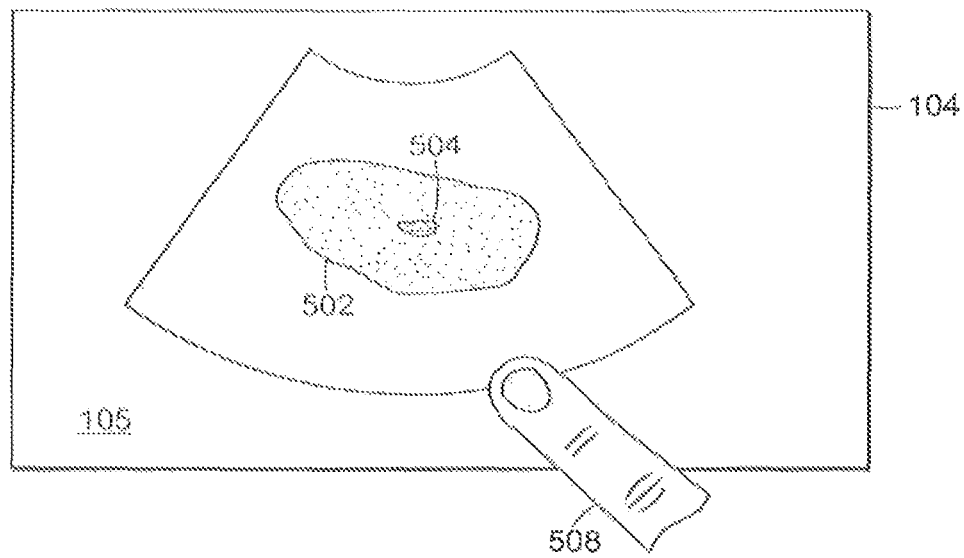
FIGS. 5A and 5B are exemplary representations of a liver with a cystic lesion on a touch screen display of the medical ultrasound imaging system in accordance with preferred embodiments of the invention.
Figure 5B:
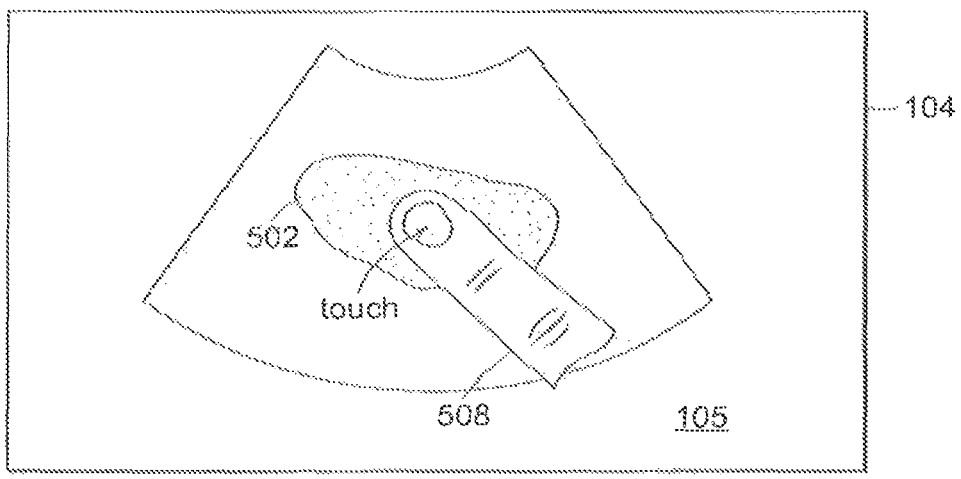
Figure 5C:
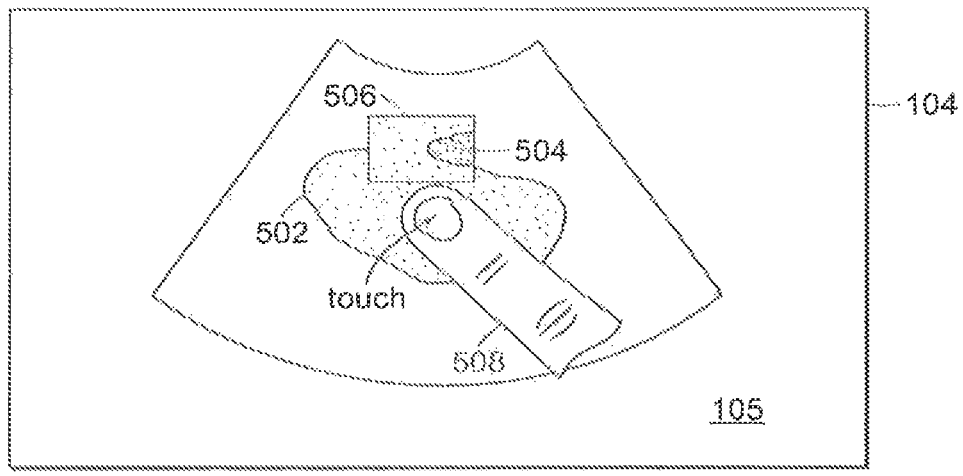
FIGS. 5C and 5D are exemplary representations of the liver and cystic lesion on the touch screen display of FIGS. 5A and 5B, including a virtual window that corresponds to a magnified portion of the liver.
Figure 5D:
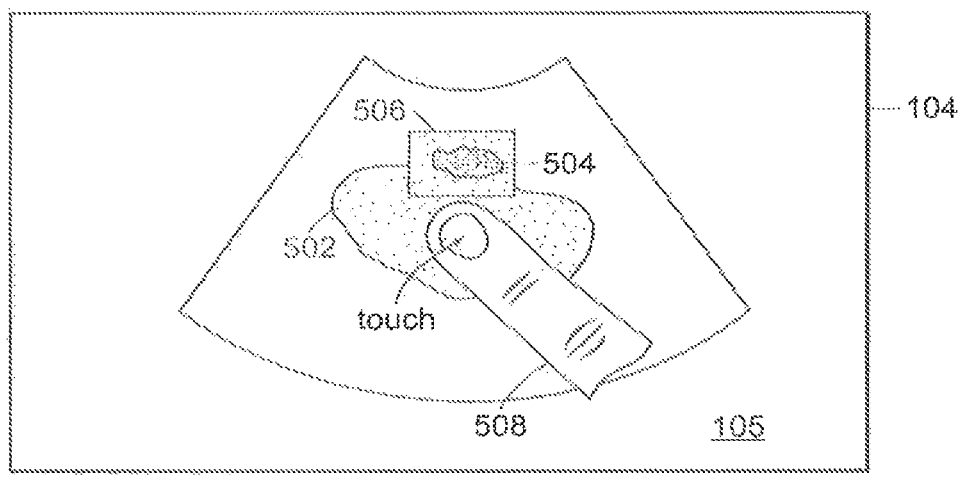

FIGS. 5A and 5B depict an original ultrasound image of an exemplary object, namely, a liver 502 with a cystic lesion 504, displayed on the touch screen display 104 of the medical ultrasound imaging equipment 100 (see FIG. 1). It is noted that such an ultrasound image can be generated by the medical ultrasound imaging equipment 100 in response to penetration of the liver tissue by ultrasound waves generated by an ultrasound probe/transducer operatively connected to the equipment 100. Measurements and/or tracings of the liver 502 with the cystic lesion 504 can be performed directly on the original ultrasound image displayed on the touch screen display 104 (see FIGS. 5A and 5B), or on a magnified version of the ultrasound image. For example, the user can obtain such a magnified version of the ultrasound image using a spread gesture (see, e.g., the spread gesture 312; FIG. 3) by placing two (2) fingers on the surface 105 of the touch screen display 104, and spreading them apart to magnify the original ultrasound image. Such measurements and/or tracings of the liver 502 and cystic lesion 504 can also be performed on a magnified portion of the ultrasound image within the virtual window 506 (see FIGS. 5C and 5D) on the touch screen display 104.

For example, using his or her finger (see, e.g., a finger 508; FIGS. 5A-5D), the user can obtain the virtual window 506 by employing a press gesture (see, e.g., the press gesture 320; FIG. 3) against the surface 105 of the touch screen display 104 (see FIG. 5B) in the vicinity of a region of interest, such as the region corresponding to the cystic lesion 504. In response to the press gesture, the virtual window 506 (see FIGS. 5C and 5D) is displayed on the touch screen display 104, possibly at least partially superimposed on the original ultrasound image, thereby providing the user with a view of a magnified portion of the liver 502 in the vicinity of the cystic lesion 504. For example, the virtual window 506 of FIG. 5C can provide a view of a magnified portion of the ultrasound image of the cystic lesion 504, which is covered by the finger 508 pressed against the surface 105 of the touch screen display 104. To re-position the magnified cystic lesion 504 within the virtual window 506, the user can employ a press and drag gesture (see, e.g., the press and drag gesture 322; FIG. 3) against the surface 105 of the touch screen display 104 (see FIG. 5D), thereby moving the image of the cystic lesion 504 to a desired position within the virtual window 506. In one embodiment, the medical ultrasound imaging equipment 100 can be configured to allow the user to select a level of magnification within the virtual window 506 to be 2 times larger, 4 times larger, or any other suitable number of times larger than the original ultrasound image. The user can remove the virtual window 506 from the touch screen display 104 by lifting his or her finger (see, e.g., the finger 508; FIGS. 5A-5D) from the surface 105 of the touch screen display 104.

Figure 6A:
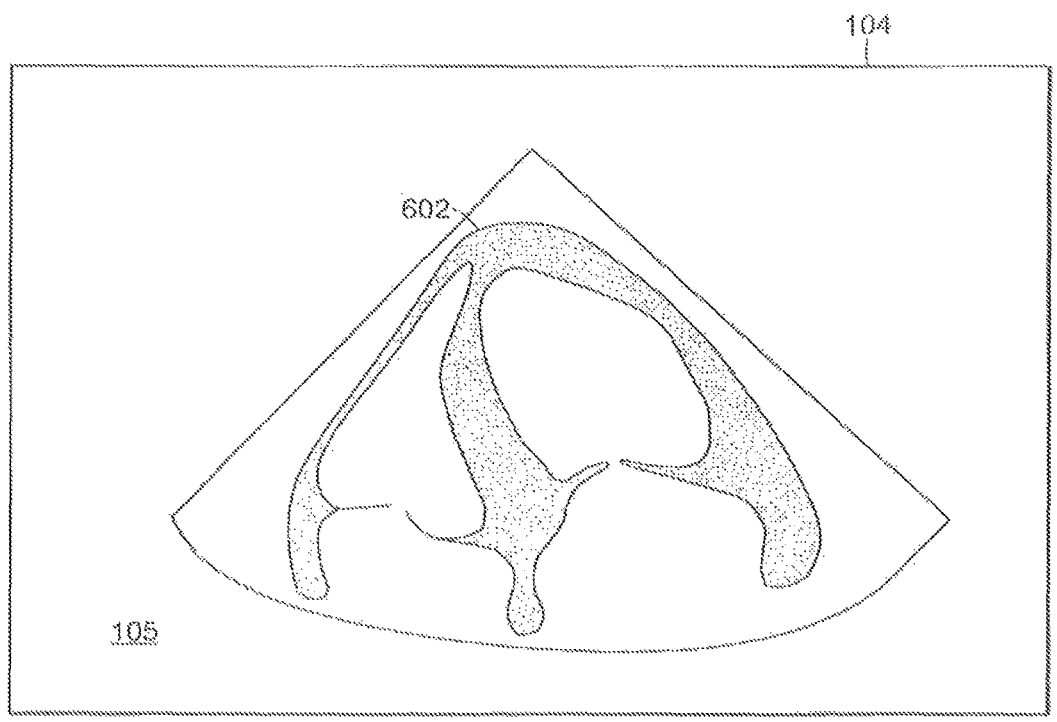
FIG. 6A is an exemplary representation of an apical four (4) chamber view of a heart on the touch screen display of the medical ultrasound imaging system.
Figure 6B:
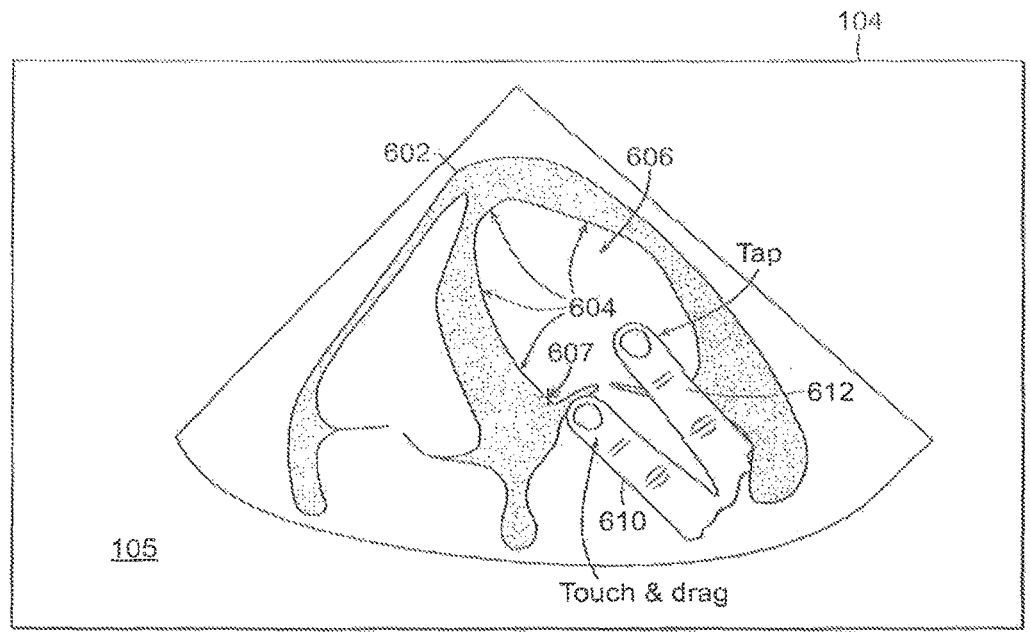
FIGS. 6B-6E illustrates an exemplary manual tracing of an endocardial border of a left ventricle of the heart on the touch screen display of FIG. 6A.

FIG. 6A depicts an ultrasound image of another exemplary object, namely, an apical four (4) chamber view of a heart 602, displayed on the touch screen display 104 of the medical ultrasound imaging equipment 100 (see FIG. 1). It is noted that such an ultrasound image can be generated by the medical ultrasound imaging equipment 100 in response to penetration of the heart tissue by ultrasound waves generated by an ultrasound probe/transducer operatively connected to the equipment 100. Measurements and/or tracings of the heart 602 can be performed directly on the original ultrasound image displayed on the touch screen display 104 (see FIGS. 6A-6E), or on a magnified version of the ultrasound image. For example, using his or her fingers (see, e.g., fingers 610, 612; FIGS. 6B-6E), the user can perform a manual tracing of an endocardial border 604 (see FIG. 6B) of a left ventricle 606 (see FIGS. 6B-6E) of the heart 602 by employing one or more multi-finger gestures on the surface 105 of the touch screen display 104. In one embodiment, using his or her fingers (see, e.g., the fingers 610, 612; FIGS. 6B-6E), the user can obtain a cursor 607 (see FIG. 6B) by employing a double tap gesture (see, e.g., the double tap gesture 310; FIG. 3AA-3AL) on the surface 105 of the touch screen display 104, and can move the cursor 607 by employing a drag gesture (see, e.g., the drag gesture 318; FIG. 3AA-3AL) using one finger, such as the finger 610, thereby moving the cursor 607 to a desired location on the touch screen display 104. The systems and methods described herein can be used for the quantitative measurement of heart wall motion and specifically for the measurement of ventricular dysynchrony as described in detail in U.S. application Ser. No. 10/817,316 filed on Apr. 2, 2004, the entire contents of which is incorporated herein by reference.

Figure 6C:
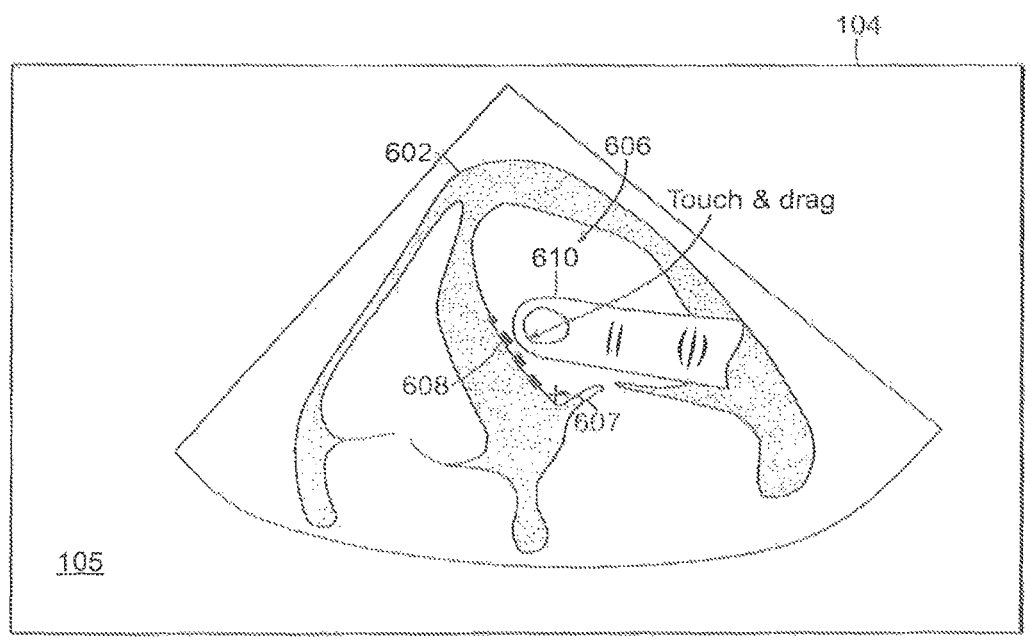
Figure 6D:
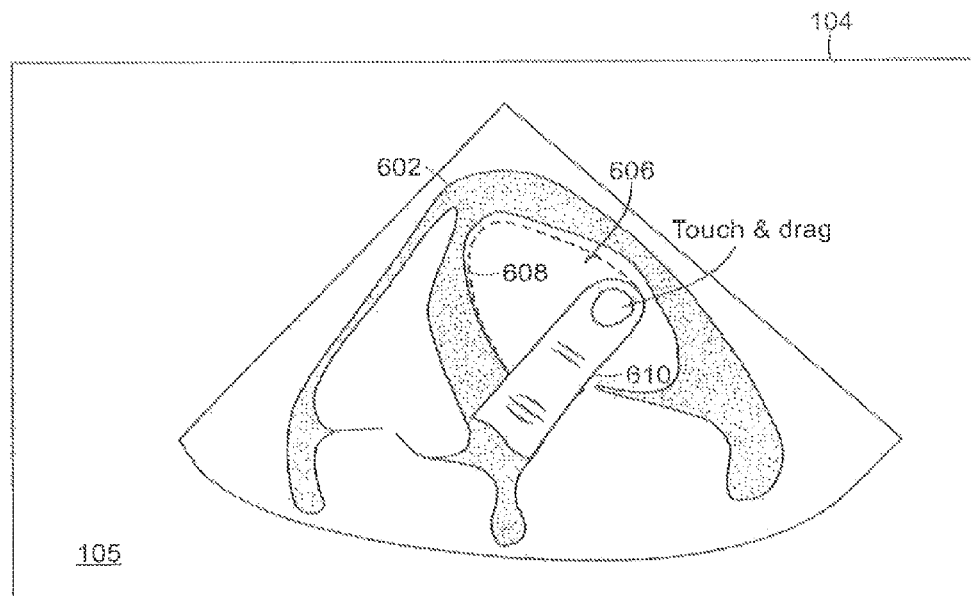
Figure 6E:
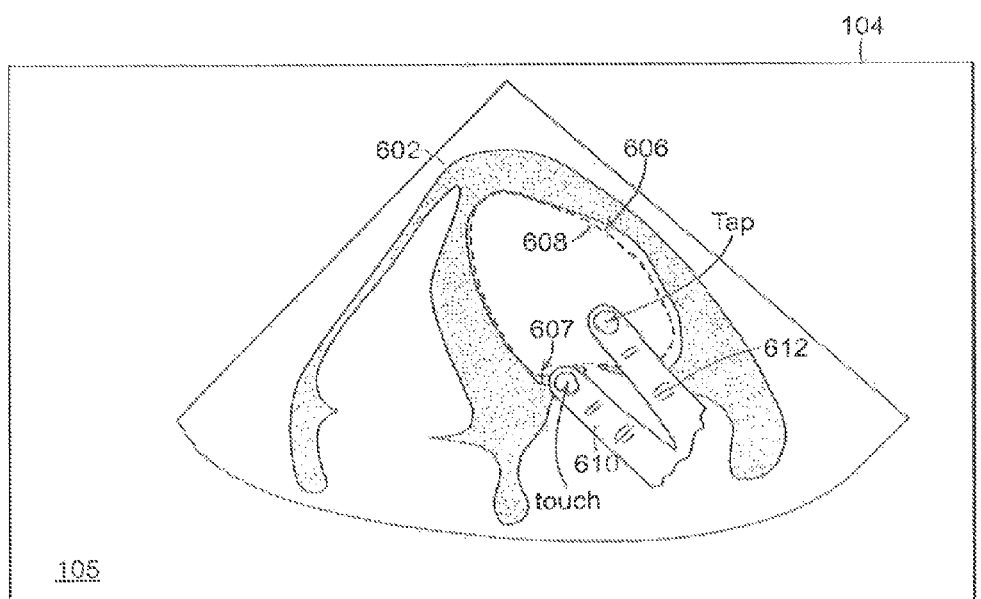

Once the cursor 607 is at the desired location on the touch screen display 104, as determined by the location of the finger 610, the user can fix the cursor 607 at that location by employing a tap gesture (see, e.g., the tap gesture 302; see FIG. 3) using another finger, such as the finger 612. To perform a manual tracing of the endocardial border 604 (see FIG. 6B), the user can employ a press and drag gesture (see, e.g., the press and drag gesture 322; FIG. 3) using the finger 610, as illustrated in FIGS. 6C and 6D. Such a manual tracing of the endocardial border 604 can be highlighted on the touch screen display 104 in any suitable fashion, such as by a dashed line 608 (see FIGS. 6C-6E). The manual tracing of the endocardial border 604 can continue until the finger 610 arrives at any suitable location on the touch screen display 104, or until the finger 610 returns to the location of the cursor 607, as illustrated in FIG. 6E. Once the finger 610 is at the location of the cursor 607, or at any other suitable location, the user can complete the manual tracing operation by employing a tap gesture (see, e.g., the tap gesture 302; see FIG. 3) using the finger 612. It is noted that such a manual tracing operation can be employed to trace any other suitable feature(s) and/or waveform(s), such as a pulsed wave Doppler (PWD) waveform. In one embodiment, the medical ultrasound imaging equipment 100 can be configured to perform any suitable calculation(s) and/or measurement(s) relating to such feature(s) and/or waveform(s), based at least in part on a manual tracing(s) of the respective feature(s)/waveform(s).

Figure 7C:
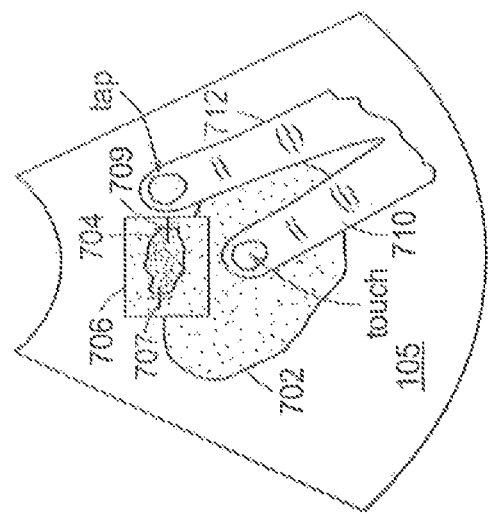
FIGS. 7A-7C illustrates an exemplary measurement of the size of the cystic lesion on the liver within the virtual window of FIGS. 5C and 5D.
Figure 7B:
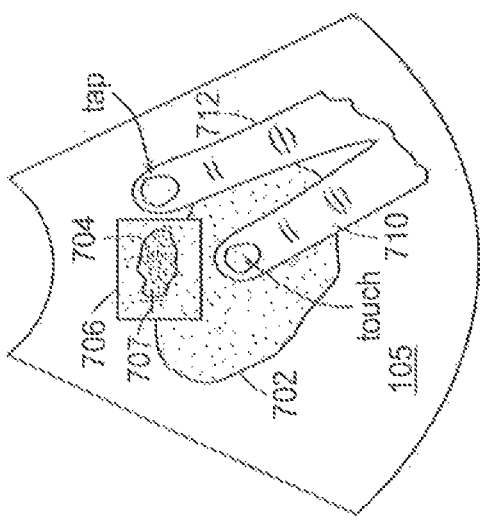
Figure 7A:
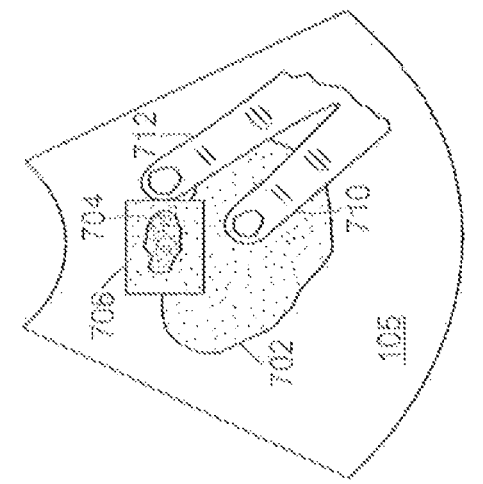

As described above, the user can perform measurements and/or tracings of objects on a magnified portion of an original ultrasound image of a displayed object within a virtual window on the touch screen display 104. FIGS. 7A-7C depict an original ultrasound image of an exemplary object, namely, a liver 702 with a cystic lesion 704, displayed on the touch screen display 104 of the medical ultrasound imaging equipment 100 (see FIG. 1). FIGS. 7A-7C further depict a virtual window 706 that provides a view of a magnified portion of the ultrasound image of the cystic lesion 704, which is covered by one of the user's fingers, such as a finger 710, pressed against the surface 105 of the touch screen display 104. Using his or her fingers (see, e.g., fingers 710, 712; FIGS. 7A-7C), the user can perform a size measurement of the cystic lesion 704 within the virtual window 706 by employing one or more multi-finger gestures on the surface 105 of the touch screen display 104.

For example, using his or her fingers (see, e.g., the fingers 710, 712; FIGS. 7A-7C), the user can obtain a first cursor 707 (see FIGS. 7B, 7C) by employing a double tap gesture (see, e.g., the double tap gesture 310; FIG. 3) on the surface 105, and can move the first cursor 707 by employing a drag gesture (see, e.g., the drag gesture 318; FIG. 3) using one finger, such as the finger 710, thereby moving the first cursor 707 to a desired location. Once the first cursor 707 is at the desired location, as determined by the location of the finger 710, the user can fix the first cursor 707 at that location by employing a tap gesture (see, e.g., the tap gesture 302; see FIG. 3) using another finger, such as the finger 712. Similarly, the user can obtain a second cursor 709 (see FIG. 7C) by employing a double tap gesture (see, e.g., the double tap gesture 310; FIG. 3) on the surface 105, and can move the second cursor 709 by employing a drag gesture (see, e.g., the drag gesture 318; FIG. 3) using the finger 710, thereby moving the second cursor 709 to a desired location. Once the second cursor 709 is at the desired location, as determined by the location of the finger 710, the user can fix the second cursor 709 at that location by employing a tap gesture (see, e.g., the tap gesture 302; see FIG. 3) using the finger 712. In one embodiment, the medical ultrasound imaging equipment 100 can be configured to perform any suitable size calculation(s) and/or measurement(s) relating to the cystic lesion 704, based at least in part on the locations of the first and second cursors 707, 709.

Figure 8A:
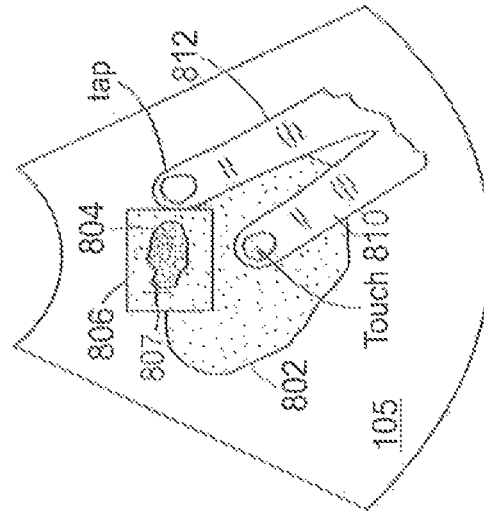
FIGS. 8A-8C illustrates an exemplary caliper measurement of the cystic lesion on the liver within the virtual window of FIGS. 5C and 5D.
Figure 8B:
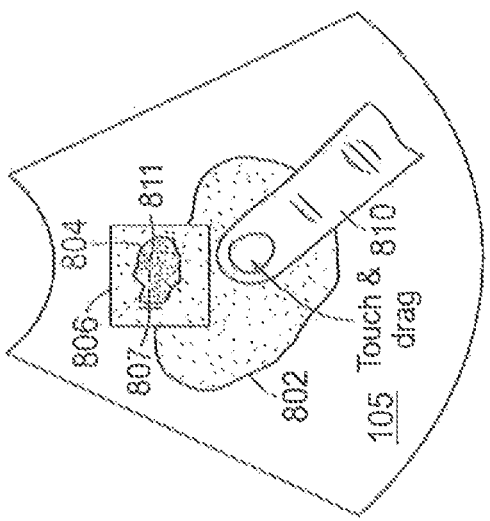
Figure 8C:
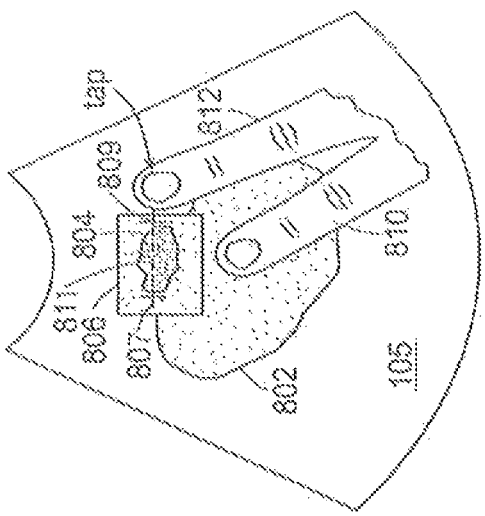

FIGS. 8A-8C depict an original ultrasound image of an exemplary object, namely, a liver 802 with a cystic lesion 804, displayed on the touch screen display 104 of the medical ultrasound imaging equipment 100 (see FIG. 1). FIGS. 8a-8c further depict a virtual window 806 that provides a view of a magnified portion of the ultrasound image of the cystic lesion 804, which is covered by one of the user's fingers, such as a finger 810, pressed against the surface 105 of the touch screen display 104. Using his or her fingers (see, e.g., fingers 810, 812; FIGS. 8A-8C), the user can perform a caliper measurement of the cystic lesion 804 within the virtual window 806 by employing one or more multi-finger gestures on the surface 105 of the touch screen display 104.

For example, using his or her fingers (see, e.g., the fingers 810, 812; FIGS. 8A-8C), the user can obtain a first cursor 807 (see FIGS. 8B, 8C) by employing a double tap gesture (see, e.g., the double tap gesture 310; FIG. 3) on the surface 105, and can move the cursor 807 by employing a drag gesture (see, e.g., the drag gesture 318; FIG. 3) using one finger, such as the finger 810, thereby moving the cursor 807 to a desired location. Once the cursor 807 is at the desired location, as determined by the location of the finger 810, the user can fix the cursor 807 at that location by employing a tap gesture (see, e.g., the tap gesture 302; see FIG. 3) using another finger, such as the finger 812. The user can then employ a press and drag gesture (see, e.g., the press and drag gesture 322; FIG. 3) to obtain a connecting line 811 (see FIGS. 8B, 8C), and to extend the connecting line 811 from the first cursor 807 across the cystic lesion 804 to a desired location on another side of the cystic lesion 804. Once the connecting line 811 is extended across the cystic lesion 804 to the desired location on the other side of the cystic lesion 804, the user can employ a tap gesture (see, e.g., the tap gesture 302; see FIG. 3) using the finger 812 to obtain and fix a second cursor 809 (see FIG. 8C) at that desired location. In one embodiment, the medical ultrasound imaging equipment 100 can be configured to perform any suitable caliper calculation(s) and/or measurement(s) relating to the cystic lesion 804, based at least in part on the connecting line 811 extending between the locations of the first and second cursors 807, 809.

Figure 9A:
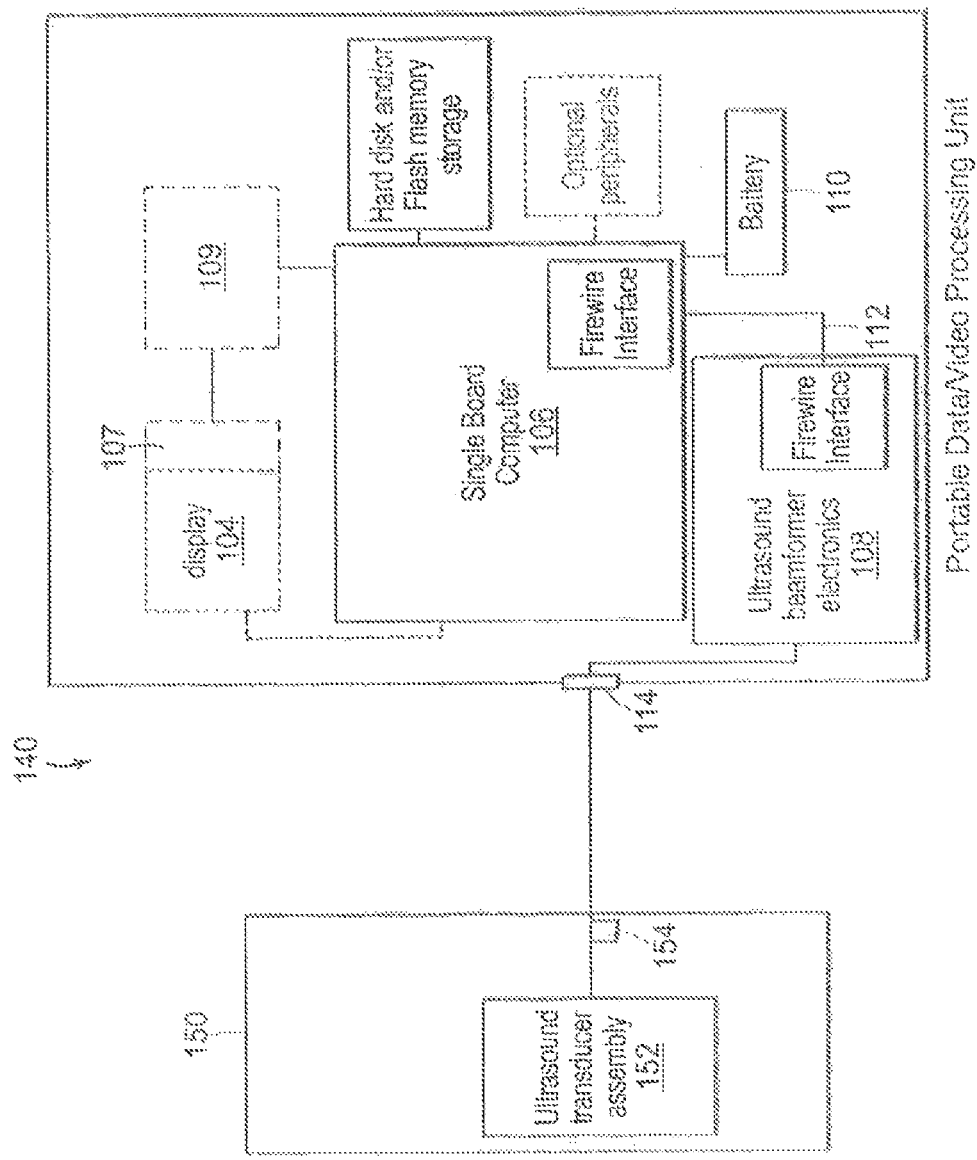
FIG. 9A illustrates one of a plurality of transducer arrays attached to the processor housing.

FIG. 9A shows a system 140 in which a transducer housing 150 with an array of transducer elements 152 can be attached at connector 114 to housing 102. Each probe 150 can have a probe identification circuit 154 that uniquely identifies the probe that is attached. When the user inserts a different probe with a different array, the system identifies the probe operating parameters. Note that preferred embodiments can include a display 104 having a touch sensor 107 which can be connected to a touch processor 109 that analyzes touchscreen data from the sensor 107 and transmits commands to both image processing operations and to a beamformer control processor (1116, 1124). In a preferred embodiment, the touch processor can include a computer readable medium that stores instructions to operate an ultrasound touchscreen engine that is operable to control display and imaging operations described herein.

Figure 9B:
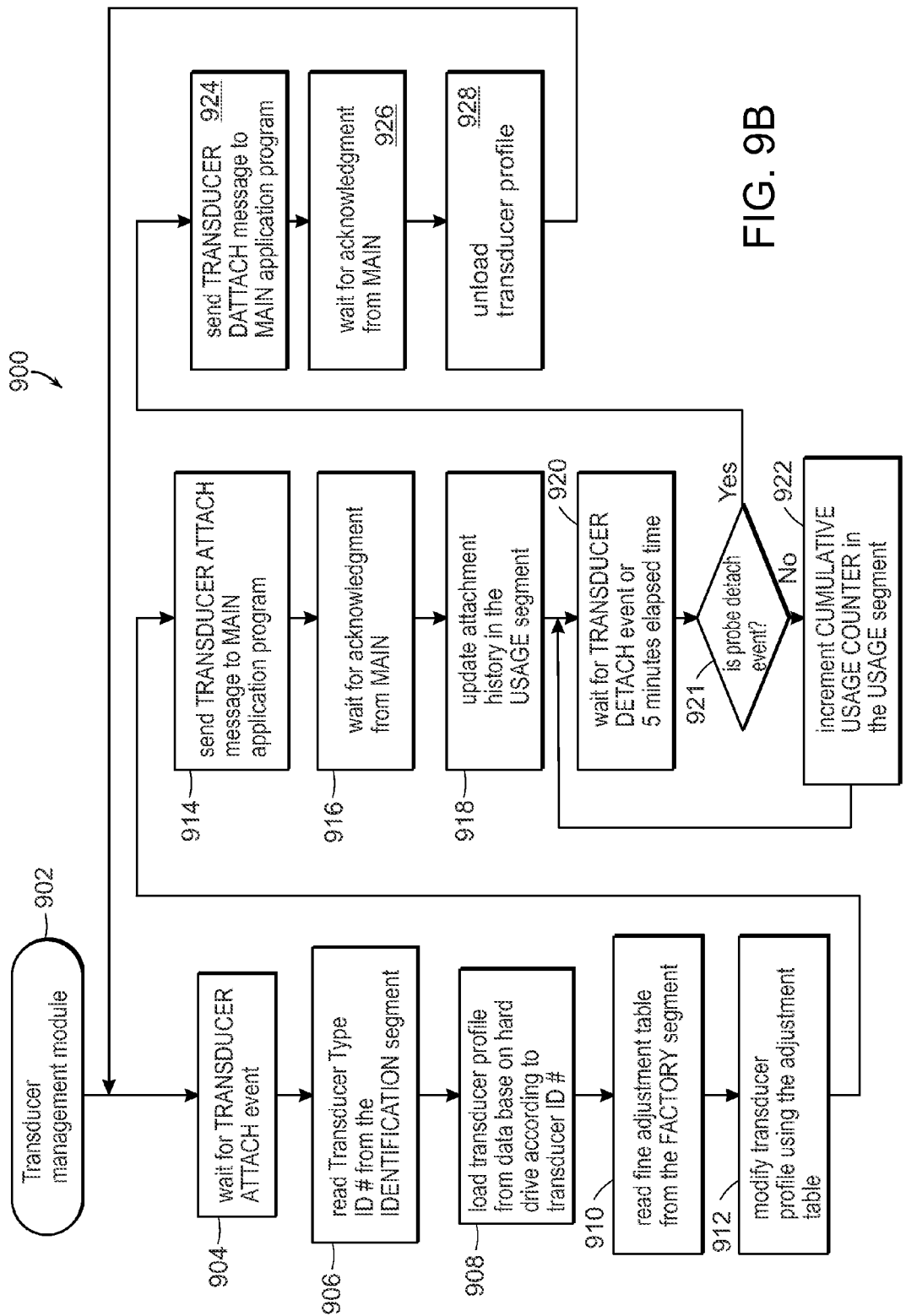
FIG. 9B shows a transducer attach sequence in accordance with exemplary embodiments.

FIG. 9B shows a software flowchart 900 of a typical transducer management module 902 within the ultrasound application program. When a TRANSDUCER ATTACH 904 event is detected, the Transducer Management Software Module 902 first reads the Transducer type ID 906 and hardware revision information from the IDENTIFICATION Segment. The information is used to fetch the particular set of transducer profile data 908 from the hard disk and load it into the memory of the application program. The software then reads the adjustment data from the FACTORY Segment 910 and applies the adjustments to the profile data just loaded into memory 912. The software module then sends a TRANSDUCER ATTACH Message 914 to the main ultrasound application program, which uses the transducer profile already loaded. After acknowledgment 916, an ultrasound imaging sequence is performed and the USAGE segment is updated 918. The Transducer Management Software Module then waits for either a TRANSDUCER DETACH event 920, or the elapse of 5 minutes. If a TRANSDUCER DETACH event is detected 921, a message 924 is sent and acknowledged 926, the transducer profile data set is removed 928 from memory and the module goes back to wait for another TRANSDUCER ATTACH event. If a 5 minutes time period expires without detecting a TRANSDUCER DETACH event, the software module increments a Cumulative Usage Counter in the USAGE Segment 922, and waits for another 5 minutes period or a TRANSDUCER DETACH event. The cumulative usage is recorded in memory for maintenance and replacement records.

There are many types of ultrasound transducers. They differ by geometry, number of elements, and frequency response. For example, a linear array with center frequency of 10 to 15 MHz is better suited for breast imaging, and a curved array with center frequency of 3 to 5 MHz is better suited for abdominal imaging.

It is often necessary to use different types of transducers for the same or different ultrasound scanning sessions. For ultrasound systems with only one transducer connection, the operator will change the transducer prior to the start of a new scanning session.

In some applications, it is necessary to switch among different types of transducers during one ultrasound scanning session. In this case, it is more convenient to have multiple transducers connected to the same ultrasound system, and the operator can quickly switch among these connected transducers by hitting a button on the operator console, without having to physically detach and re-attach the transducers, which takes a longer time. Preferred embodiments of the invention can include a multiplexor within the tablet housing that can select between a plurality of probe connector ports within the tablet housing, or alternatively, the tablet housing can be connected to an external multiplexor that can be mounted on a cart as described herein.

Figure 9C:
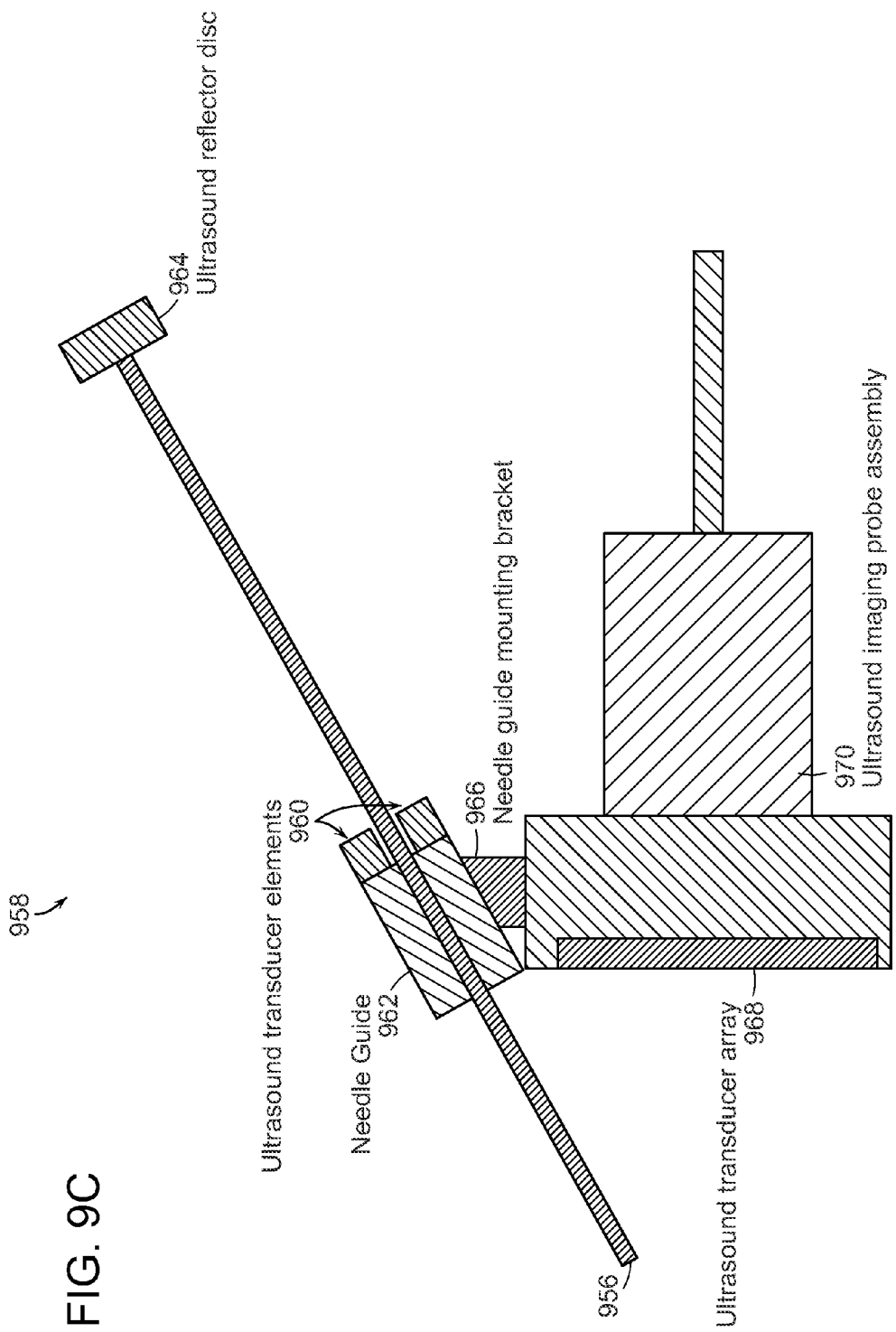
FIG. 9C shows a perspective view of a needle sensing positioning system with exemplary embodiments.

FIG. 9C is a perspective view of an exemplary needle sensing positioning system using ultrasound transducers without the requirement of any active electronics in the sensor assembly. The sensor transducer may include a passive ultrasound transducer element. The elements may be used in a similar way as a typical transducer probe, utilizing the ultrasound engine electronics. The system 958 includes the addition of ultrasound transducer elements 960, added to a needle guide 962, that is represented in FIG. 9C but that may be any suitable form factor. The ultrasound transducer element 960, and needle guide 962, may be mounted using a needle guide mounting bracket 966, to an ultrasound transducer probe acoustic handle or an ultrasound imagining probe assembly 970. The needle with a disc mounted on the exposed end, the ultrasound reflector disc 964, is reflective to ultrasonic waves.

The ultrasound transducer element 960, on the needle guide 962, may be connected to the ultrasound engine. The connection may be made through a separate cable to a dedicated probe connector on the engine, similar to a sharing the pencil CW probe connector. In an alternate embodiment, a small short cable may be plugged into the larger image transducer probe handle or a split cable connecting to the same probe connector at the engine. In another alternate embodiment the connection may be made via an electrical connector between the image probe handle and the needle guide without a cable in between. In an alternate embodiment the ultrasound transducer elements on the needle guide may be connected to the ultrasound engine by enclosing the needle guide and transducer elements in the same mechanical enclosure of the imagining probe handle.

Figure 9D:
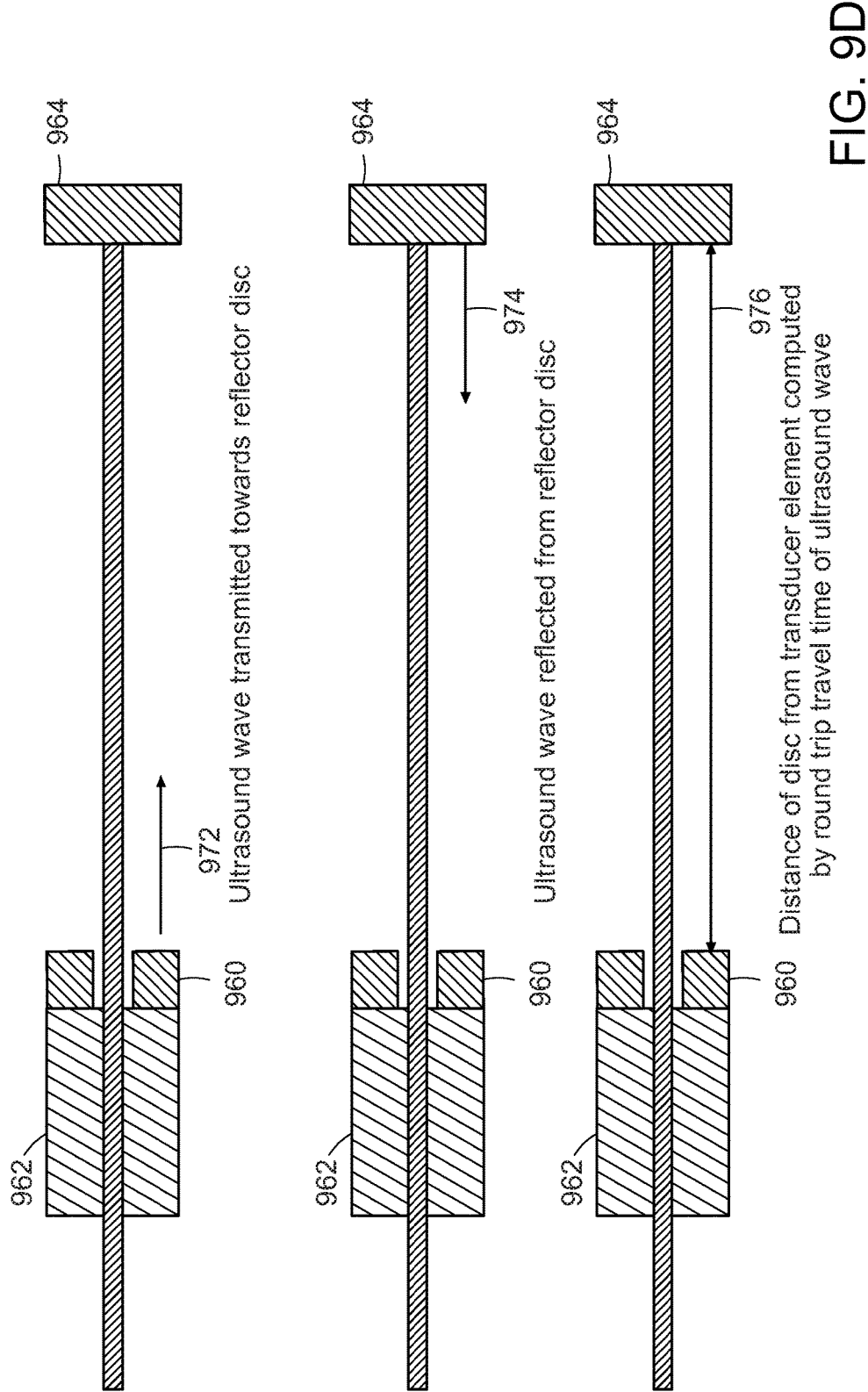
FIG. 9D shows a perspective view of a needle guide with exemplary embodiments.

FIG. 9D is a perspective view of a needle guide 962, positioned with transducer elements 960 and the ultrasound reflector disc 964. The position of the reflector disc 964 is located by transmitting ultrasonic wave 972, from the transducer element 960 on the needle guide 962. The ultrasound wave 972 travels through the air towards reflector disc 964 and is reflected by the reflector disc 964. The reflected ultrasound wave 974, reaches the transducer element 960 on the needle guide 962. The distance 976, between the reflector disc 964, and the transducer element 960 is calculated from the time elapsed and the speed of sound in the air.

Figure 9E:
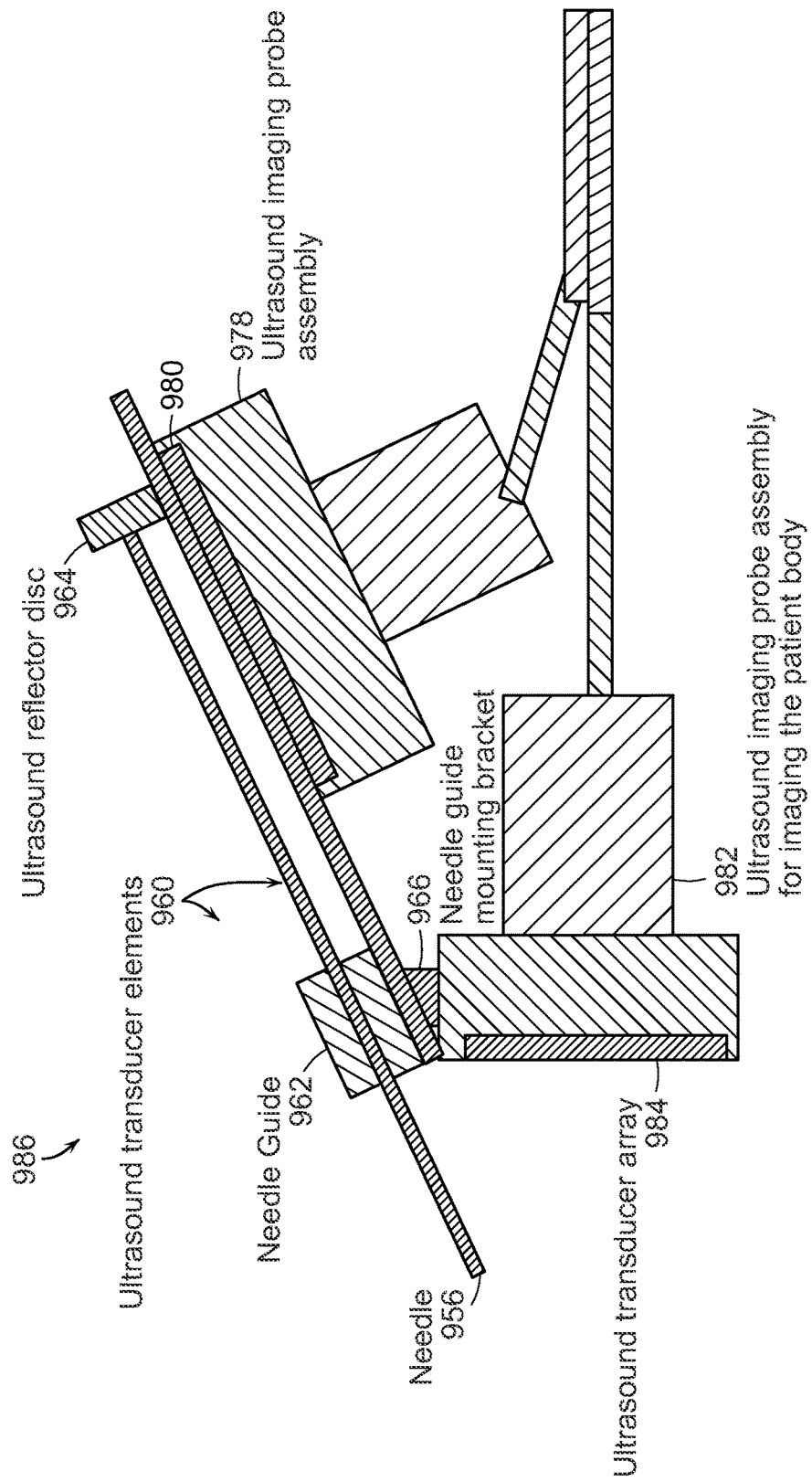
FIG. 9E shows a perspective view of a needle sensing positioning system with exemplary embodiments.

FIG. 9E is a perspective view of an alternate embodiment of the exemplary needle sensing positioning system using ultrasound transducers without the requirement of any active electronics in the sensor assembly. The sensor transducer may include a passive ultrasound transducer element. The elements may be used in a similar way as a typical transducer probe, utilizing the ultrasound engine electronics.

The system 986 includes needle guide 962 that may be mounted to a needle guide mounting bracket 966 that may be coupled to an ultrasound imaging probe assembly for imaging the patient's body 982, or alternative suitable form factors. The ultrasound reflector disc 964 may be mounted at the exposed end of the needle 956. In this embodiment a linear ultrasound acoustic array 978, is mounted parallel to the direction of movement of the needle 956. The linear ultrasound acoustic array 978 includes an ultrasound transducer array 980 positioned parallel to the needle 956. In this embodiment an ultrasound imagining probe assembly 982, is positioned for imagining the patient body. The ultrasound imaging probe assembly for imaging the patient body 982 is configured with an ultrasound transducer array 984.

In this embodiment, the position of the ultrasound reflector disc 964 can be detected by using the ultrasound transducer array 980 coupled to an ultrasound imaging probe assembly for imaging 978. The position of the reflector disc 964 is located by transmitting ultrasonic wave 972, from the transducer element 980 on the ultrasound imaging probe assembly for imaging 978. The ultrasound wave 972 travels through the air towards reflector disc 964 and is reflected by the reflector disc 964. The reflected ultrasound wave 974, reaches the transducer element 980 on the ultrasound imaging probe assembly for imaging 978. The distance 976, between the reflector disc 964, and the transducer element 980 is calculated from the time elapsed and the speed of sound in the air. In an alternate embodiment an alternate algorithm may be used to sequentially scan the polarity of elements in the transducer array and analyze the reflections produced per transducer array element. In an alternate embodiment a plurality of scans may occur prior to forming an ultrasound image.

Figure 10A:
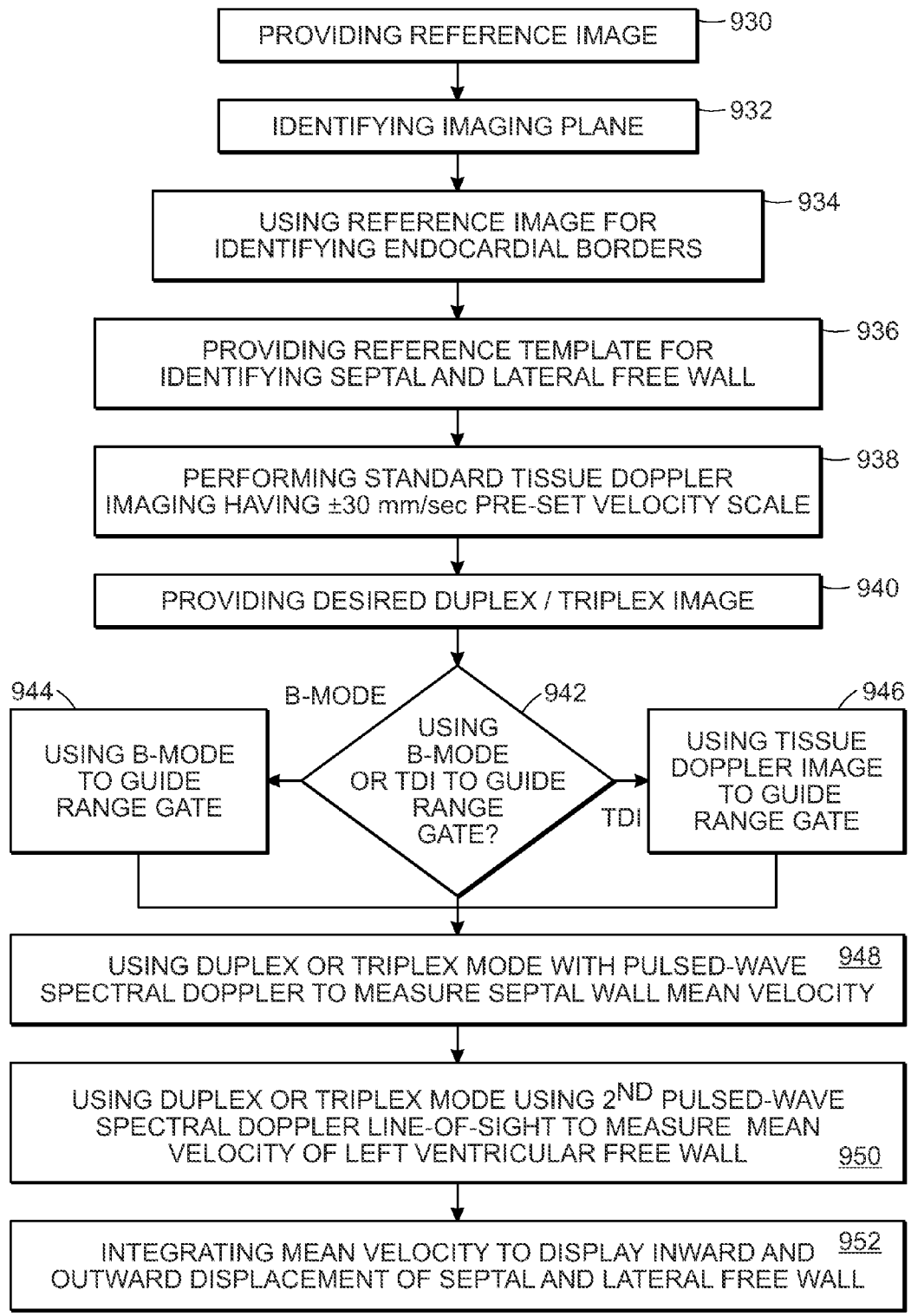
FIG. 10A shows a method of measuring heart wall motion.

FIG. 10A illustrates an exemplary method for monitoring the synchrony of a heart in accordance with exemplary embodiments. In the method, a reference template is loaded into memory and used to guide a user in identifying an imaging plane (per step 930). Next a user identifies a desired imaging plane (per step 932). Typically an apical 4-chamber view of the heart is used; however, other views may be used without departing from the spirit of the invention.

At times, identification of endocardial borders may be difficult, and when such difficulties are encountered tissue Doppler imaging of the same view may be employed (per step 934). A reference template for identifying the septal and lateral free wall is provided (per step 936). Next, standard tissue Doppler imaging (TDI) with pre-set velocity scales of, say, ±30 cm/sec may be used (per step 938).

Then, a reference of the desired triplex image may be provided (per step 940). Either B-mode or TDI may be used to guide the range gate (per step 942). B-mode can be used for guiding the range gate (per step 944) or TDI for guiding the range gate (per step 946). Using TDI or B-mode for guiding the range gate also allows the use of a direction correction angle for allowing the Spectral Doppler to display the radial mean velocity of the septal wall. A first pulsed-wave spectral Doppler is then used to measure the septal wall mean velocity using duplex or triplex mode (per step 948). The software used to process the data and calculate dysychrony can utilize a location (e.g. a center point) to automatically set an angle between dated locations on a heart wall to assist in simplifying the setting of parameters.

A second range-gate position is also guided using a duplex image or a TDI (per step 950), and a directional correction angle may be used if desired. After step 950, the mean velocity of the septal wall and lateral free wall are being tracked by the system. Time integration of the Spectral Doppler mean velocities 952 at regions of interest (e.g., the septum wall and the left ventricular free wall) then provides the displacement of the septal and left free wall, respectively.

The above method steps may be utilized in conjunction with a high pass filtering means, analog or digital, known in the relevant arts for removing any baseline disturbance present in collected signals. In addition, the disclosed method employs multiple simultaneous PW Spectral Doppler lines for tracking movement of the interventricular septum and the left ventricular fee wall. In additional, a multiple gate structure may be employed along each spectral line, thus allowing quantitative measurement of regional wall motion. Averaging over multiple gates may allow measurement of global wall movement.

Figure 10B:
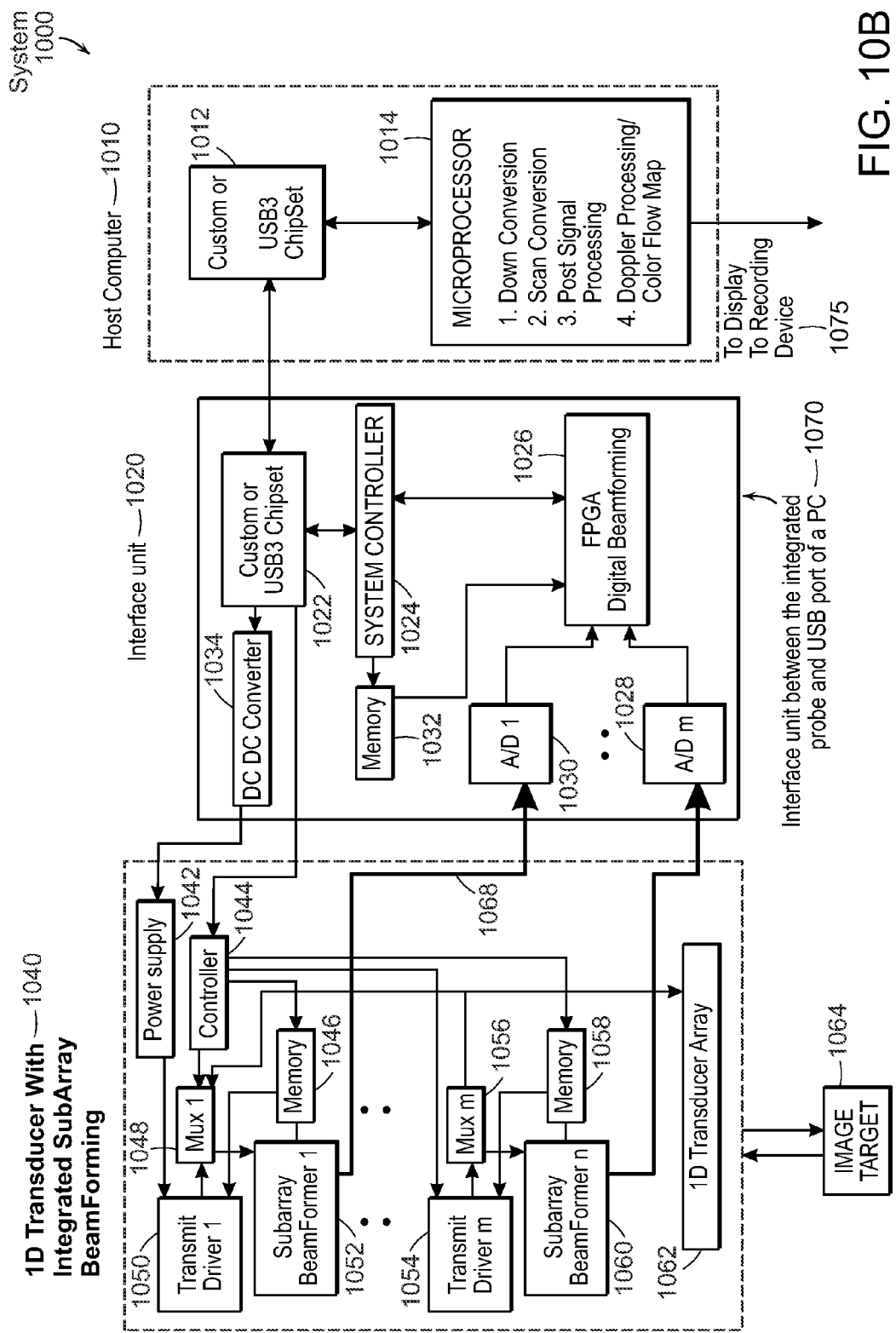
FIG. 10B shows a schematic block diagram for an integrated ultrasound probe with exemplary embodiments.

FIG. 10B is a detailed schematic block diagram for an exemplary embodiment of the integrated ultrasound probe 1040 can be connected to any PC 1010 through an Interface unit 1020. The ultra sound probe 1040 is configured to transmit ultrasound waves to and reduce reflected ultrasound waves from on ore more image targets 1064. The transducer 1040 can be coupled to the interface unit 1020 using one or more cables 1066, 1068. The interface unit 1020 can be positioned between the integrated ultrasound probe 1040 and the host computer 1010. The two stage beam forming system 1040 and 1020 can be connected to any PC through a USB connection 1022, 1012.

The ultrasound probe 1040, can include sub-arrays/apertures 1052 consisting of neighboring elements with an aperture smaller than that of the whole array. Returned echoes are received by the 1D transducer array 1062 and transmitted to the controller 1044. The controller initiates formation of a coarse beam by transmitting the signals to memory 1058, 1046. The memory 1058, 1046 transmits a signal to a transmit Driver 1 1050, and Transmit Driver m 1054. Transmit Driver 1 1050 and Transmit Driver m 1054 then send the signal to mux1 1048 and mux m 1056, respectively. The signal is transmitted to sub-array beamformer 1 1052 and sub-array beamformer n 1060.

The outputs of each coarse beam forming operation can include further processing through a second stage beam forming in the interface unit 1020 to convert the beam forming output to digital representation. The coarse beam forming operations can be coherently summed to form a fine beam output for the array. The signals can be transmitted from the ultrasound probe 1040 sub-array beam former 1 1052 and sub-array beam former n 1060 to the A/D convertors 1030 and 1028 within the interface unit 1020. Within the interface unit 1020 there are A/D converters 1028, 1030 for converting the first stage beam forming output to digital representation. The digital conversion can be received from the A/D convertors 1030, 1028 by a customer ASIC such as a FPGA 1026 to complete the second stage beam forming. The FPGA Digital beam forming 1026 can transmit information to the system controller 1024. The system controller can transmit information to a memory 1032 which may send a signal back to the FPGA Digital Beam forming 1026. Alternatively, the system controller 1024 may transmit information to the custom USB3 Chipset 1022. The USB3 Chipset 1022 may then transmit information to a DC-DC convertor 1034. In turn, the DC-DC convertor 1034 may transmit power from the interface unit 1020 to the ultrasound probe 1040. Within the ultrasound probe 1040 a power supply 1042 may receive the power signal and interface with the transmit driver 1 1050 to provide the power to the front end integration probe.

The Interface unit 1020 custom or USB3 Chipset 1022 may be used to provide a communication link between the interface unit 10220 and the host computer 1010. The custom or USB3 Chipset 1022 transmits a signal to the host computer's 1010 custom or USB3 Chipset 1012. The custom or the USB3 Chipset 1012 then interfaces with the microprocessor 1014. The microprocessor 1014 then may display information or send information to a device 1075.

In an alternate embodiment, a narrow band beamformer can be used. For example, an individual analog phase shifter is applied to each of the received echoes. The phase shifted outputs within each sub-array are then summed to form a coarse beam. The A/D converts can be used to digitize each of the coarse beams; a digital beam former is then used to form the fine beam.

In another embodiment, forming a 64 element linear array may use eight adjacent elements to form a coarse beam output. Such arrangement may utilize eight output analog cables connecting the outputs of the integrated probe to the interface units. The coarse beams may be sent through the cable to the corresponding A/D convertors located in the interface unit. The digital delay is used to form a fine beam output. Eight A/D convertors may be required to form the digital representation.

In another embodiment, forming a 128 element array may use sixteen sub-array beam forming circuits. Each circuit may form a coarse beam from an adjacent eight element array provided in the first stage output to the interface unit. Such arrangement may utilize sixteen output analog cables connecting the outputs of the integrated probe to the interface units to digitize the output. A PC microprocessor or a DSP may be used to perform the down conversion, basebanding, scan conversion and post image processing functions. The microprocessor or DSP can also be used to perform all the Doppler processing functions.

Figure 10C:
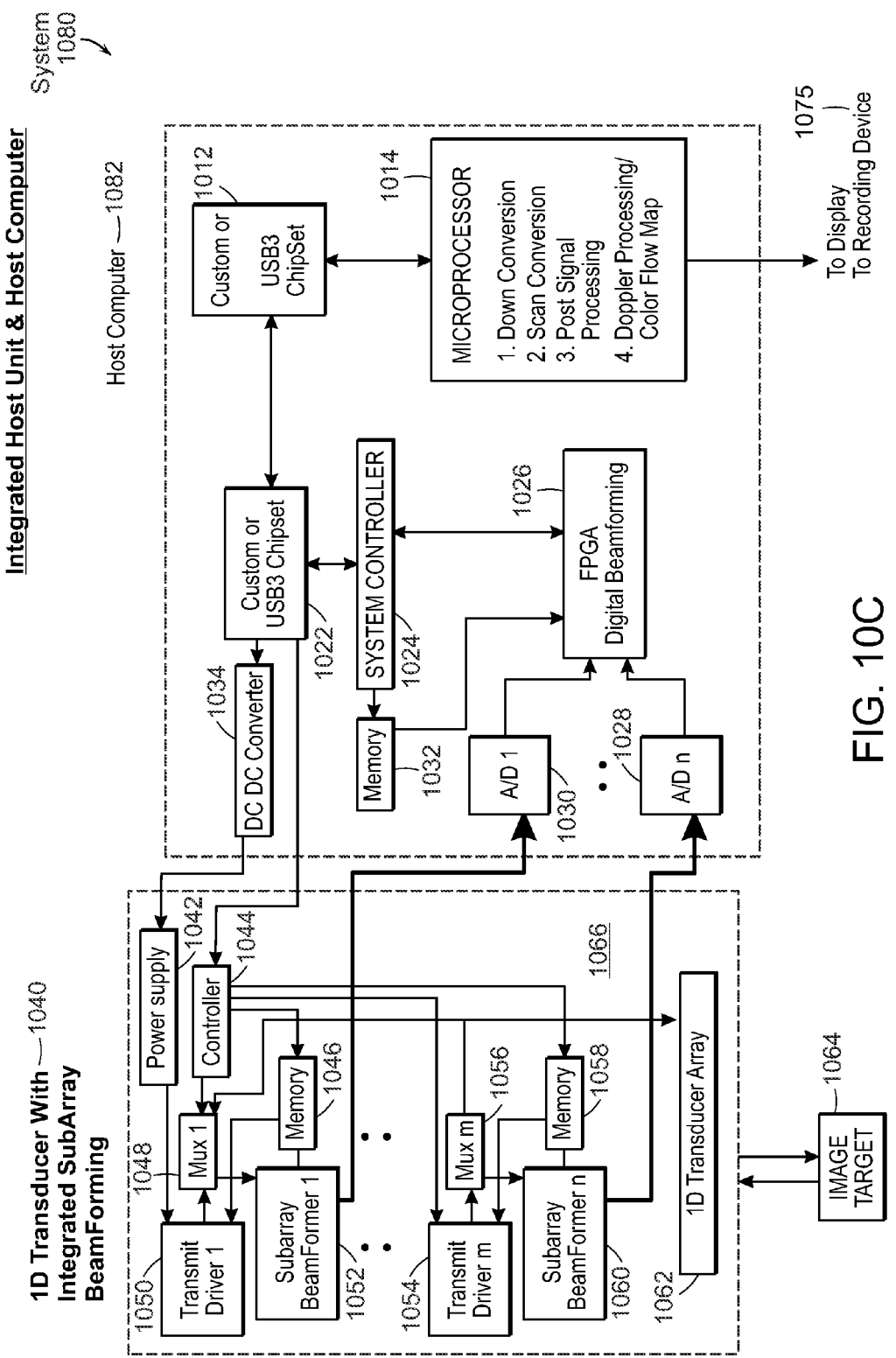
FIG. 10C shows a schematic block diagram for an integrated ultrasound probe with exemplary embodiments.

FIG. 10C is a detailed schematic block diagram for an exemplary embodiment of the integrated ultrasound probe 1040 with the first sub array beamforming circuit, and the second stage beamforming circuits are integrated inside the host computer 1082. The back end computer with the second stage beamforming circuit may be a PDA, tablet or mobile device housing. The ultra sound probe 1040 is configured to transmit ultrasound waves to and reduce reflected ultrasound waves from on ore more image targets 1064. The transducer 1040 is coupled to the host computer 1082 using one or more cables 1066, 1068. Note that A/D circuit elements can also be placed in the transducer probe housing.

The ultrasound probe 1040 includes subarray/apertures 1052 consisting of neighboring elements with an aperture smaller than that of the whole array. Returned echoes are received by the 1D transducer array 1062 and transmitted to the controller 1044. The controller initiates formation of a coarse beam by transmitting the signals to memory 1058, 1046. The memory 1058, 1046 transmits a signal to a transmit Driver 1 1050, and Transmit Driver m 1054. Transmit Driver 1 1050 and Transmit Driver m 1054 then send the signal to mux 1 1048 and mux m 1056, respectively. The signal is transmitted to subarray beamformer 1 1052 and subarray beamformer n 1060.

The outputs of each coarse beam forming operation then go through a second stage beam forming in the interface unit 1020 to convert the beam forming output to digital representation. The coarse beamforming operations are coherently summed to form a fine beam output for the array. The signals are transmitted from the ultrasound probe 1040 subarray beamformer 1 1052 and subarray beamformer n 1060 to the A/D convertors 1030 and 1028 within the host computer 1082. Within the host computer 1082 there are A/D converters 1028, 1030 for converting the first stage beamforming output to digital representation. The digital conversion is received from the A/D convertors 1030, 1028 by a customer ASIC such as a FPGA 1026 to complete the second stage beamforming. The FPGA Digital beamforming 1026 transmits information to the system controller 1024. The system controller transmits information to a memory 1032 which may send a signal back to the FPGA Digital Beam forming 1026. Alternatively, the system controller 1024 may transmit information to the custom USB3 Chipset 1022. The USB3 Chipset 1022 may then transmit information to a DC-DC convertor 1034. In turn, the DC-DC convertor 1034 may transmit power from the interface unit 1020 to the ultrasound probe 1040. Within the ultrasound probe 1040 a power supply 1042 may receive the power signal and interface with the transmit driver 1 1050 to provide the power to the front end integration probe. The power supply can include a battery to enable wireless operation of the transducer assembly. A wireless transceiver can be integrated into controller circuit or a separate communications circuit to enable wireless transfer of image data and control signals.

The host computer's 1082 custom or USB3 Chipset 1022 may be used to provide a communication link between the custom or USB3 Chipset 1012 to transmits a signal to the microprocessor 1014. The microprocessor 1014 then may display information or send information to a device 1075.

Figure 2A:
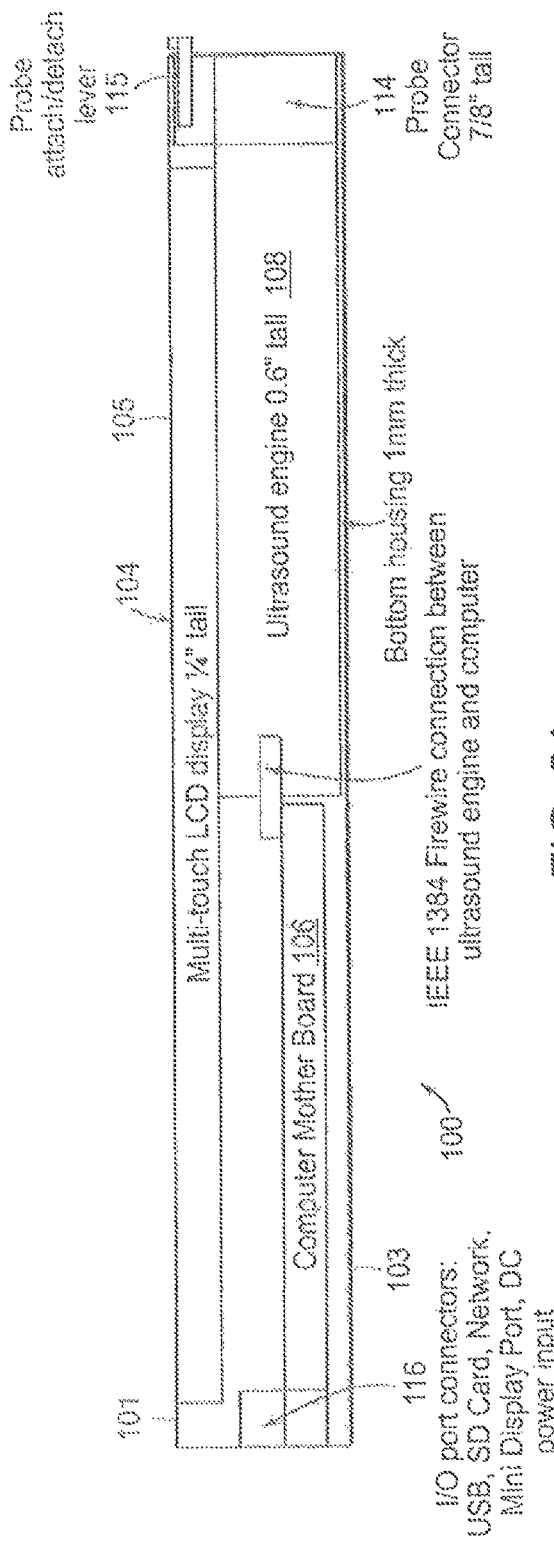
FIGS. 2A and 2B are side views of the medical ultrasound imaging system in accordance with preferred embodiments of the invention.
Figure 2B:
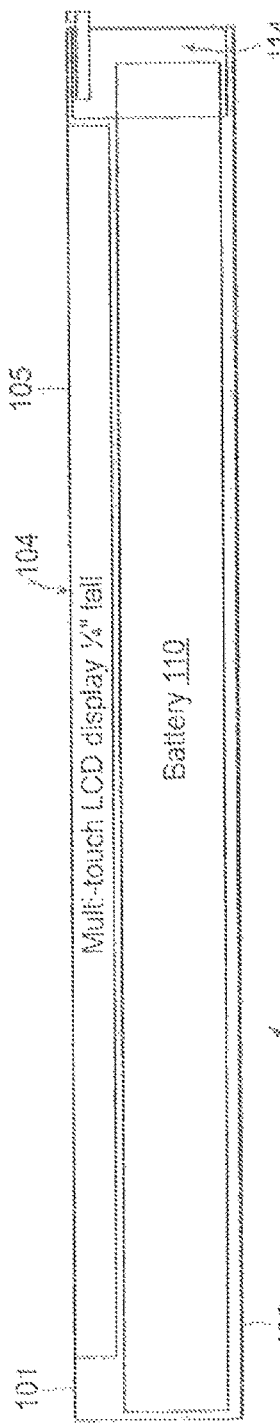
Figure 11:
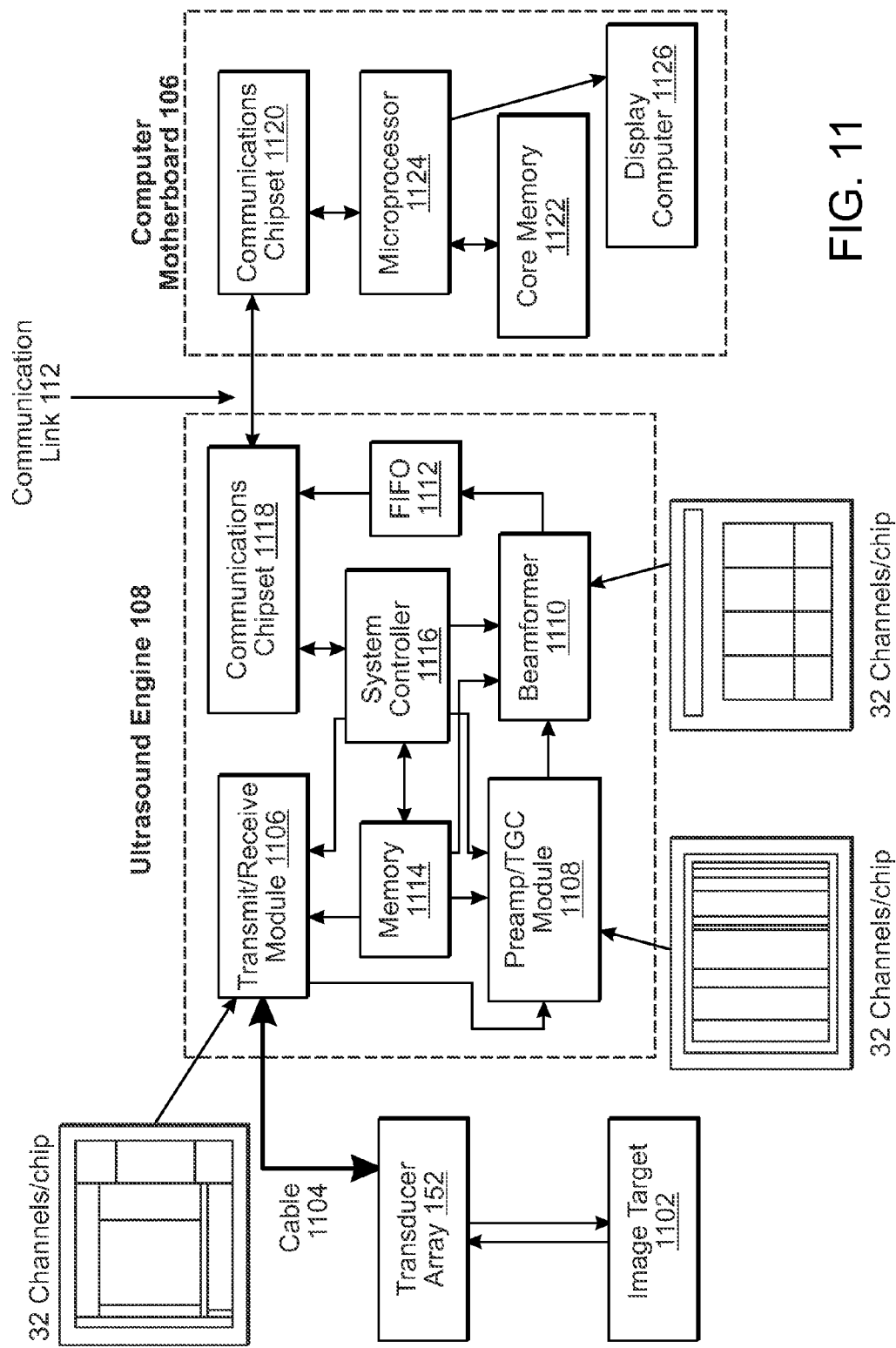
FIG. 11 is a detailed schematic block diagram of an exemplary embodiment of an ultrasound engine (i.e., the front-end ultrasound specific circuitry) and an exemplary embodiment of a computer motherboard (i.e., the host computer) of the exemplary ultrasound device.

FIG. 11 is a detailed schematic block diagram of an exemplary embodiment of the ultrasound engine 108 (i.e., the front-end ultrasound specific circuitry) and an exemplary embodiment of the computer motherboard 106 (i.e., the host computer) of the ultrasound device illustrated in FIGS. 1 and 2A. The components of the ultrasound engine 108 and/or the computer motherboard 106 may be implemented in application-specific integrated circuits (ASICs). Exemplary ASICs have a high channel count and can pack 32 or more channels per chip in some exemplary embodiments. One of ordinary skill in the art will recognize that the ultrasound engine 108 and the computer motherboard 106 may include more or fewer modules than those shown. For example, the ultrasound engine 108 and the computer motherboard 106 may include the modules shown in FIG. 17.

A transducer array 152 is configured to transmit ultrasound waves to and receive reflected ultrasound waves from one or more image targets 1102. The transducer array 152 is coupled to the ultrasound engine 108 using one or more cables 1104.

The ultrasound engine 108 includes a high-voltage transmit/receive (TR) module 1106 for applying drive signals to the transducer array 152 and for receiving return echo signals from the transducer array 152. The ultrasound engine 108 includes a pre-amp/time gain compensation (TGC) module 1108 for amplifying the return echo signals and applying suitable TGC functions to the signals. The ultrasound engine 108 includes a sampled-data beamformer 1110 that the delay coefficients used in each channel after the return echo signals have been amplified and processed by the pre-amp/TGC module 1108.

In some exemplary embodiments, the high-voltage TR module 1106, the pre-amp/TGC module 1108, and the sample-interpolate receive beamformer 1110 may each be a silicon chip having 8 to 64 channels per chip, but exemplary embodiments are not limited to this range. In certain embodiments, the high-voltage TR module 1106, the pre-amp/TGC module 1108, and the sample-interpolate receive beamformer 1110 may each be a silicon chip having 8, 16, 32, 64 channels, and the like. As illustrated in FIG. 11, an exemplary TR module 1106, an exemplary pre-amp/TGC module 1108 and an exemplary beamformer 1110 may each take the form of a silicon chip including 32 channels.

The ultrasound engine 108 includes a first-in first-out (FIFO) buffer module 1112 which is used for buffering the processed data output by the beamformer 1110. The ultrasound engine 108 also includes a memory 1114 for storing program instructions and data, and a system controller 1116 for controlling the operations of the ultrasound engine modules.

The ultrasound engine 108 interfaces with the computer motherboard 106 over a communications link 112 which can follow a standard high-speed communications protocol, such as the Fire Wire (IEEE 1394 Standards Serial Interface) or fast (e.g., 200-400 Mbits/second or faster) Universal Serial Bus (USB 2.0 USB 3.0), protocol. The standard communication link to the computer motherboard operates at least at 400 Mbits/second or higher, preferably at 800 Mbits/second or higher. Alternatively, the link 112 can be a wireless connection such as an infrared (IR) link. The ultrasound engine 108 includes a communications chipset 1118 (e.g., a Fire Wire chipset) to establish and maintain the communications link 112.

Similarly, the computer motherboard 106 also includes a communications chipset 1120 (e.g., a Fire Wire chipset) to establish and maintain the communications link 112. The computer motherboard 106 includes a core computer-readable memory 1122 for storing data and/or computer-executable instructions for performing ultrasound imaging operations. The memory 1122 forms the main memory for the computer and, in an exemplary embodiment, may store about 4 GB of DDR3 memory. The computer motherboard 106 also includes a microprocessor 1124 for executing computer-executable instructions stored on the core computer-readable memory 1122 for performing ultrasound imaging processing operations. An exemplary microprocessor 1124 may be an off-the-shelf commercial computer processor, such as an Intel Core-i5 processor. Another exemplary microprocessor 1124 may be a digital signal processor (DSP) based processor, such as one or more DaVinci™ processors from Texas Instruments. The computer motherboard 106 also includes a display controller 1126 for controlling a display device that may be used to display ultrasound data, scans and maps.

Exemplary operations performed by the microprocessor 1124 include, but are not limited to, down conversion (for generating I, Q samples from received ultrasound data), scan conversion (for converting ultrasound data into a display format of a display device), Doppler processing (for determining and/or imaging movement and/or flow information from the ultrasound data), Color Flow processing (for generating, using autocorrelation in one embodiment, a color-coded map of Doppler shifts superimposed on a B-mode ultrasound image), Power Doppler processing (for determining power Doppler data and/or generating a power Doppler map), Spectral Doppler processing (for determining spectral Doppler data and/or generating a spectral Doppler map), and post signal processing. These operations are described in further detail in WO 03/079038 A2, filed Mar. 11, 2003, titled "Ultrasound Probe with Integrated Electronics," the entire contents of which are expressly incorporated herein by reference.

To achieve a smaller and lighter portable ultrasound devices, the ultrasound engine 108 includes reduction in overall packaging size and footprint of a circuit board providing the ultrasound engine 108. To this end, exemplary embodiments provide a small and light portable ultrasound device that minimizes overall packaging size and footprint while providing a high channel count. In some embodiments, a high channel count circuit board of an exemplary ultrasound engine may include one or more multi-chip modules in which each chip provides multiple channels, for example, 32 channels. The term "multi-chip module," as used herein, refers to an electronic package in which multiple integrated circuits (IC) are packaged into a unifying substrate, facilitating their use as a single component, i.e., as a larger IC. A multi-chip module may be used in an exemplary circuit board to enable two or more active IC components integrated on a High Density Interconnection (HDI) substrate to reduce the overall packaging size. In an exemplary embodiment, a multi-chip module may be assembled by vertically stacking a transmit/receive (TR) silicon chip, an amplifier silicon chip and a beamformer silicon chip of an ultrasound engine. A single circuit board of the ultrasound engine may include one or more of these multi-chip modules to provide a high channel count, while minimizing the overall packaging size and footprint of the circuit board.

Figure 12:
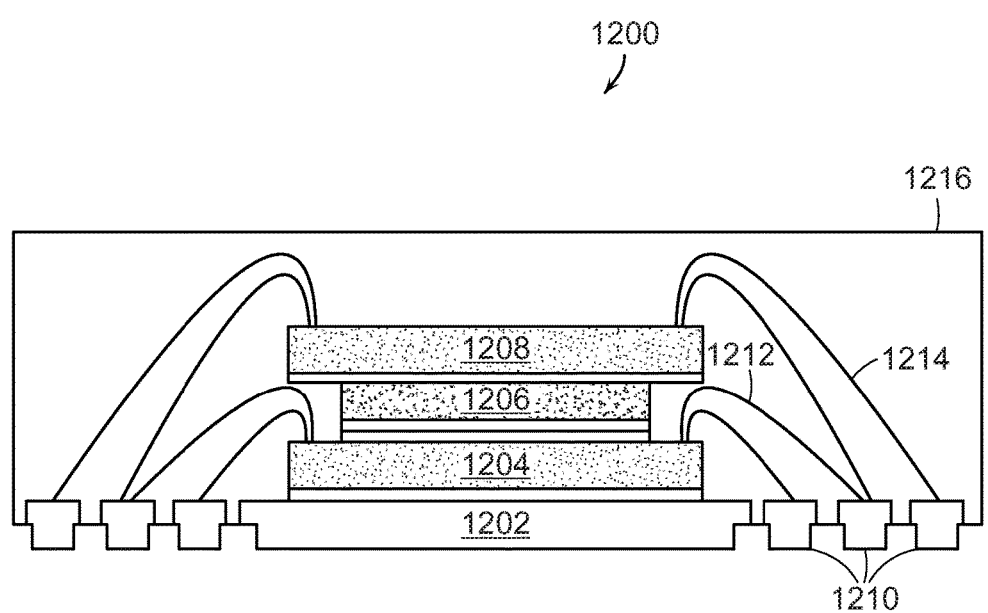
FIG. 12 depicts a schematic side view of a circuit board including a multi-chip module assembled in a vertically stacked configuration.

FIG. 12 depicts a schematic side view of a portion of a circuit board 1200 including a multi-chip module assembled in a vertically stacked configuration. Two or more layers of active electronic integrated circuit components are integrated vertically into a single circuit. The IC layers are oriented in spaced planes that extend substantially parallel to one another in a vertically stacked configuration. In FIG. 12, the circuit board includes an HDI substrate 1202 for supporting the multi-chip module. A first integrated circuit chip 1204 including, for example, a first beamformer device is coupled to the substrate 1202 using any suitable coupling mechanism, for example, epoxy application and curing. A first spacer layer 1206 is coupled to the surface of the first integrated circuit chip 1204 opposite to the substrate 1202 using, for example, epoxy application and curing. A second integrated circuit chip 1208 having, for example, a second beamforer device is coupled to the surface of the first spacer layer 1206 opposite to the first integrated circuit chip 1204 using, for example, epoxy application and curing. A metal frame 1210 is provided for mechanical and/or electrical connection among the integrated circuit chips. An exemplary metal frame 1210 may take the form of a leadframe. The first integrated circuit chip 1204 may be coupled to the metal frame 1210 using wiring 1212. The second integrated circuit chip 1208 may be coupled to the same metal frame 1210 using wiring 1214. A packaging 1216 is provided to encapsulate the multi-chip module assembly and to maintain the multiple integrated circuit chips in substantially parallel arrangement with respect to one another.

As illustrated in FIG. 12, the vertical three-dimensional stacking of the first integrated circuit chip 1204, the first spacer layer 1206 and the second integrated circuit chip 1208 provides high-density functionality on the circuit board while minimizing overall packaging size and footprint (as compared to an ultrasound engine circuit board that does not employ a vertically stacked multi-chip module). One of ordinary skill in the art will recognize that an exemplary multi-chip module is not limited to two stacked integrated circuit chips. Exemplary numbers of chips vertically integrated in a multi-chip module may include, but are not limited to, two, three, four, five, six, seven, eight, and the like.

In one embodiment of an ultrasound engine circuit board, a single multi-chip module as illustrated in FIG. 12 is provided. In other embodiments, a plurality of multi-chip modules also illustrated in FIG. 12. In an exemplary embodiment, a plurality of multi-chip modules (for example, two multi-chip modules) may be stacked vertically on top of one another on a circuit board of an ultrasound engine to further minimize the packaging size and footprint of the circuit board.

In addition to the need for reducing the footprint, there is also a need for decreasing the overall package height in multi-chip modules. Exemplary embodiments may employ wafer thinning to sub-hundreds micron to reduce the package height in multi-chip modules.

Any suitable technique can be used to assemble a multi-chip module on a substrate. Exemplary assembly techniques include, but are not limited to, laminated MCM (MCM-L) in which the substrate is a multi-layer laminated printed circuit board, deposited MCM (MCM-D) in which the multi-chip modules are deposited on the base substrate using thin film technology, and ceramic substrate MCM (MCM-C) in which several conductive layers are deposited on a ceramic substrate and embedded in glass layers that layers are co-fired at high temperatures (HTCC) or low temperatures (LTCC).

Figure 13:
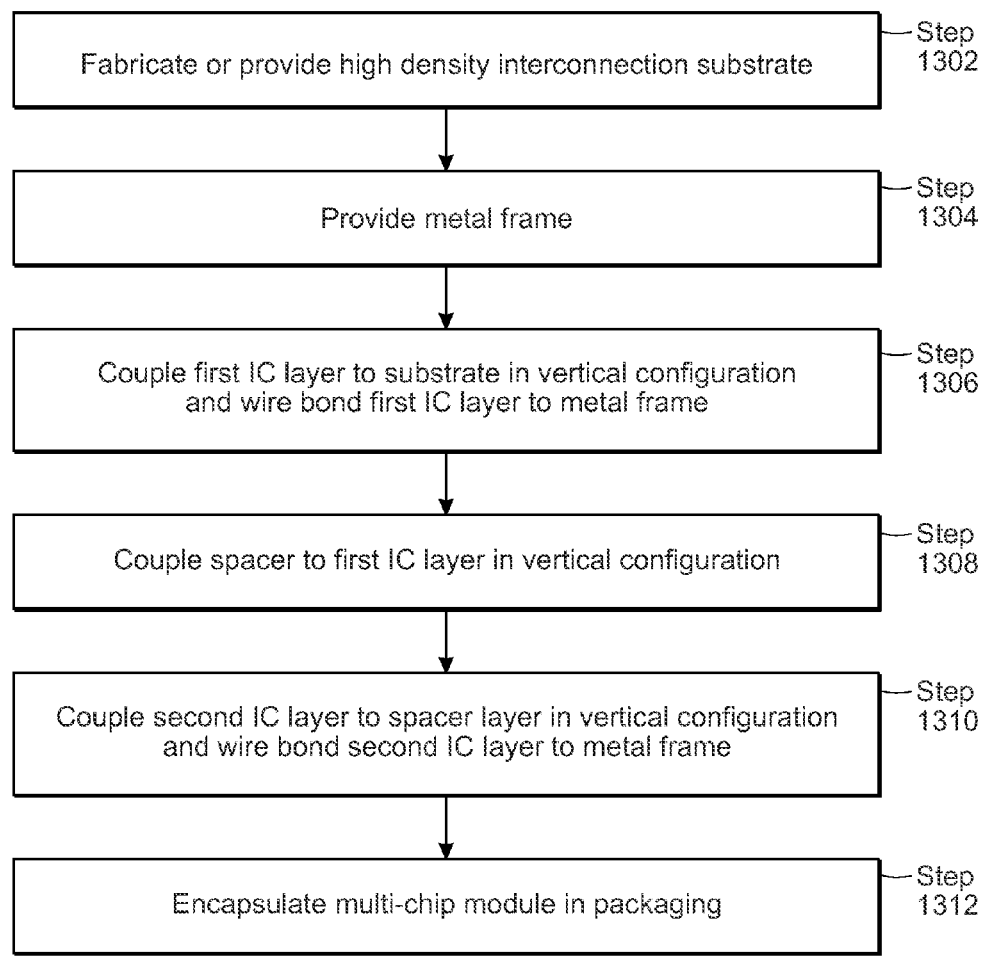
FIG. 13 is a flowchart of an exemplary method for fabricating a circuit board including a multi-chip module assembled in a vertically stacked configuration.

FIG. 13 is a flowchart of an exemplary method for fabricating a circuit board including a multi-chip module assembled in a vertically stacked configuration. In step 1302, a HDI substrate is fabricated or provided. In step 1304, a metal frame (e.g., leadframe) is provided. In step 1306, a first IC layer is coupled or bonded to the substrate using, for example, epoxy application and curing. The first IC layer is wire bonded to the metal frame. In step 1308, a spacer layer is coupled to the first IC layer using, for example, epoxy application and curing, so that the layers are stacked vertically and extend substantially parallel to each other. In step 1310, a second IC layer is coupled to the spacer layer using, for example, epoxy application and curing, so that all of the layers are stacked vertically and extend substantially parallel to one another. The second IC layer is wire bonded to the metal frame. In step 1312, a packaging is used to encapsulate the multi-chip module assembly.

Exemplary chip layers in a multi-chip module may be coupled to each other using any suitable technique. For example, in the embodiment illustrated in FIG. 12, spacer layers may be provided between chip layers to spacedly separate the chip layers. Passive silicon layers, die attach paste layers and/or die attach film layers may be used as the spacer layers. Exemplary spacer techniques that may be used in fabricating a multi-chip module is further described in Toh C H et al., "Die Attach Adhesives for 3D Same-Sized Dies Stacked Packages," the 58th Electronic Components and Technology Conference (ECTC2008), pp. 1538-43, Florida, US (27-30 May 2008), the entire contents of which are expressly incorporated herein by reference.

Important requirements for the die attach (DA) paste or film is excellent adhesion to the passivation materials of adjacent dies. Also, a uniform bond-link thickness (BLT) is required for a large die application. In addition, high cohesive strength at high temperatures and low moisture absorption are preferred for reliability.

Figure 14A:
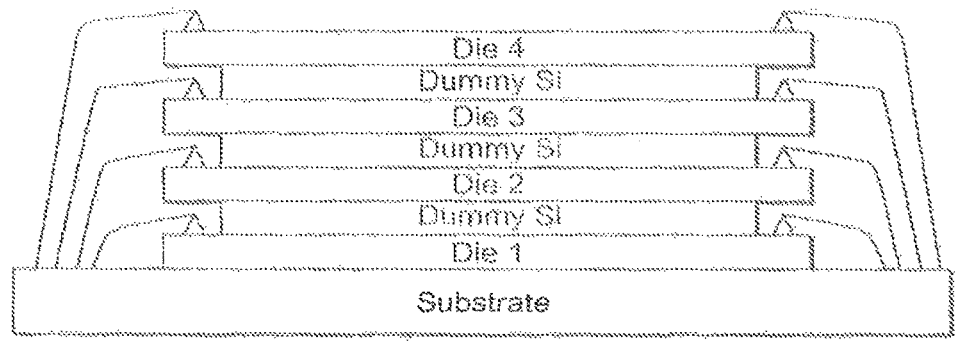
FIG. 14A is a schematic side view of a multi-chip module including four vertically stacked dies in which the dies are spacedly separated from one another by passive silicon layers with a 2-in-1 dicing die attach film (D-DAF)
Figure 14B:
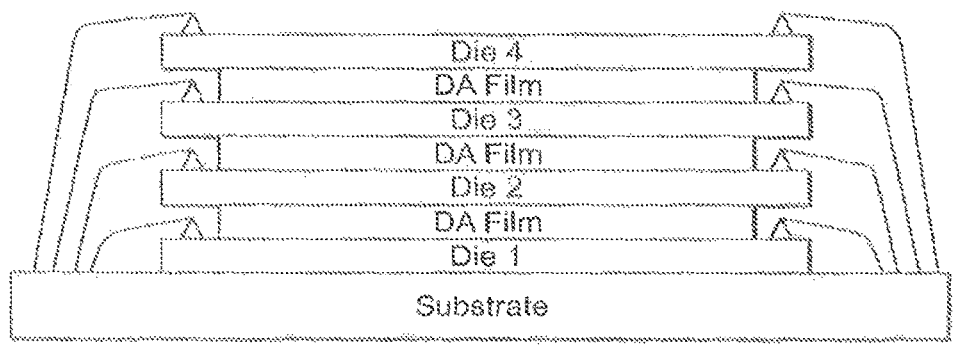
FIG. 14B is a schematic side view of a multi-chip module including four vertically stacked dies in which the dies are spacedly separated from one another by DA film-based adhesives acting as die-to-die spacers.
Figure 14C:
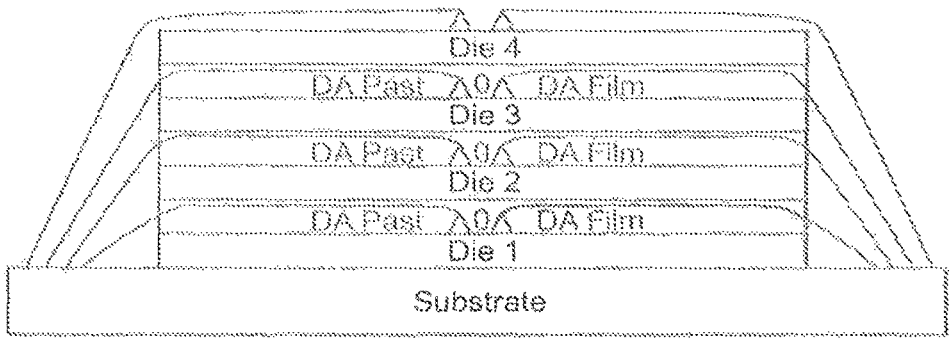
FIG. 14C is a schematic side view of a multi-chip module including four vertically stacked dies in which the dies are spacedly separated from one another by DA paste or film-based adhesives acting as die-to-die spacers.

FIGS. 14A-14C are schematic side views of exemplary multi-chip modules, including vertically stacked dies, that may be used in accordance with exemplary embodiments. Both peripheral and center pads wire bond (WB) packages are illustrated and may be used in wire bonding exemplary chip layers in a multi-chip module. FIG. 14A is a schematic side view of a multi-chip module including four vertically stacked dies in which the dies are spacedly separated from one another by passive silicon layers with a 2-in-1 dicing die attach film (D-DAF). FIG. 14B is a schematic side view of a multi-chip module including four vertically stacked dies in which the dies are spacedly separated from one another by DA film-based adhesives acting as die-to-die spacers. FIG. 14C is a schematic side view of a multi-chip module including four vertically stacked dies in which the dies are spacedly separated from one another by DA paste or film-based adhesives acting as die-to-die spacers. The DA paste or film-based adhesives may have wire penetrating capability in some exemplary embodiments. In the exemplary multi-chip module of FIG. 14C, film-over wire (FOW) is used to allow long wire bonding and center bond pads stacked die packages. FOW employs a die-attach film with wire penetrating capability that allows the same or similar-sized wire-bonded dies to be stacked directly on top of one another without passive silicon spacers. This solves the problem of stacking same or similar-sized dies directly on top of each other, which otherwise poses a challenge as there is no or insufficient clearance for the bond wires of the lower dies.

The DA material illustrated in FIGS. 14B and 14C preferably maintain a bond-line thickness (BLT) with little to no voiding and bleed out through the assembly process. Upon assembly, the DA materials sandwiched between the dies maintain an excellent adhesion to the dies. The material properties of the DA materials are tailored to maintain high cohesive strength for high temperature reliability stressing without bulk fracture. The material properties of the DA materials are tailored to also minimize or preferably eliminate moisture accumulation that may cause package reliability failures (e.g., popcorning whereby interfacial or bulk fractures occur as a result of pressure build-up from moisture in the package).

Figure 15:
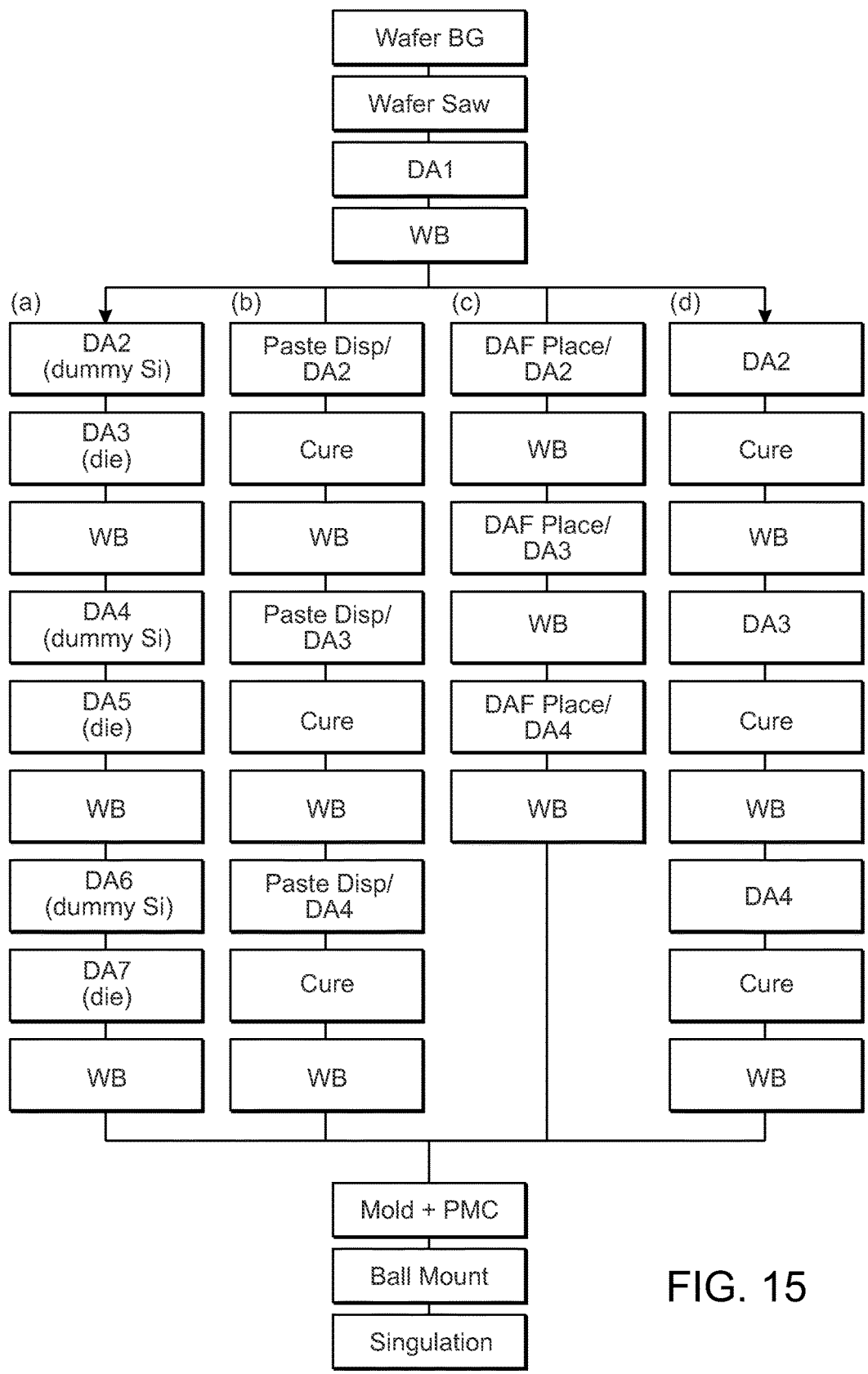
FIG. 15 is a flowchart of another exemplary method of die-to-die stacking using (a) passive silicon layers with a 2-in-1 dicing die attach film (D-DAF), (b) DA paste, (c) thick DA-film, and (d) film-over wire (FOW) including a 2-in-1 D-DAF.

FIG. 15 is a flowchart of certain exemplary methods of die-to-die stacking using (a) passive silicon layers with a 2-in-1 dicing die attach film (D-DAF), (b) DA paste, (c) thick DA-film, and (d) film-over wire (FOW) that employs a die-attach film with wire penetrating capability that allows the same or similar-sized wire-bonded dies to be stacked directly on top of one another without passive silicon spacers. Each method performs backgrinding of wafers to reduce the wafer thickness to enable stacking and high density packaging of integrated circuits. The wafers are sawed to separate the individual dies. A first die is bonded to a substrate of a multi-chip module using, for example, epoxy application and curing in an oven. Wire bonding is used to couple the first die to a metal frame.

In method (A), a first passive silicon layer is bonded to the first die in a stacked manner using a dicing die-attach film (D-DAF). A second die is bonded to the first passive layer in a stacked manner using D-DAF. Wire bonding is used to couple the second die to the metal frame. A second passive silicon layer is bonded to the second die in a stacked manner using D-DAF. A third die is bonded to the second passive layer in a stacked manner using D-DAF. Wire bonding is used to couple the third die to the metal frame. A third passive silicon layer is bonded to the third die in a stacked manner using D-DAF. A fourth die is bonded to the third passive layer in a stacked manner using D-DAF. Wire bonding is used to couple the fourth die to the metal frame.

In method (B), die attach (DA) paste dispensing and curing is repeated for multi-thin die stack application. DA paste is dispensed onto a first die, and a second die is provided on the DA paste and cured to the first die. Wire bonding is used to couple the second die to the metal frame. DA paste is dispensed onto the second die, and a third die is provided on the DA paste and cured to the second die. Wire bonding is used to couple the third die to the metal frame. DA paste is dispensed onto the third die, and a fourth die is provided on the DA paste and cured to the third die. Wire bonding is used to couple the fourth die to the metal frame.

In method (C), die attach films (DAF) are cut and pressed to a bottom die and a top die is then placed and thermal compressed onto the DAF. For example, a DAF is pressed to the first die and a second die is thermal compressed onto the DAF. Wire bonding is used to couple the second die to the metal frame. Similarly, a DAF is pressed to the second die and a third die is thermal compressed onto the DAF. Wire bonding is used to couple the third die to the metal frame. A DAF is pressed to the third die and a fourth die is thermal compressed onto the DAF. Wire bonding is used to couple the fourth die to the metal frame.

In method (D), film-over wire (FOW) employs a die-attach film with wire penetrating capability that allows the same or similar-sized wire-bonded dies to be stacked directly on top of one another without passive silicon spacers. A second die is bonded and cured to the first die in a stacked manner. Film-over wire bonding is used to couple the second die to the metal frame. A third die is bonded and cured to the first die in a stacked manner. Film-over wire bonding is used to couple the third die to the metal frame. A fourth die is bonded and cured to the first die in a stacked manner. Film-over wire bonding is used to couple the fourth die to the metal frame.

After the above-described steps are completed, in each method (a)-(d), wafer molding and post-mold curing (PMC) are performed. Subsequently, ball mount and singulation are performed.

Further details on the above-described die attachment techniques are provided in TOH C H et al., "Die Attach Adhesives for 3D Same-Sized Dies Stacked Packages," the 58th Electronic Components and Technology Conference (ECTC2008), pp. 1538-43, Florida, US (27-30 May 2008), the entire contents of which are expressly incorporated herein by reference.

Figure 16:
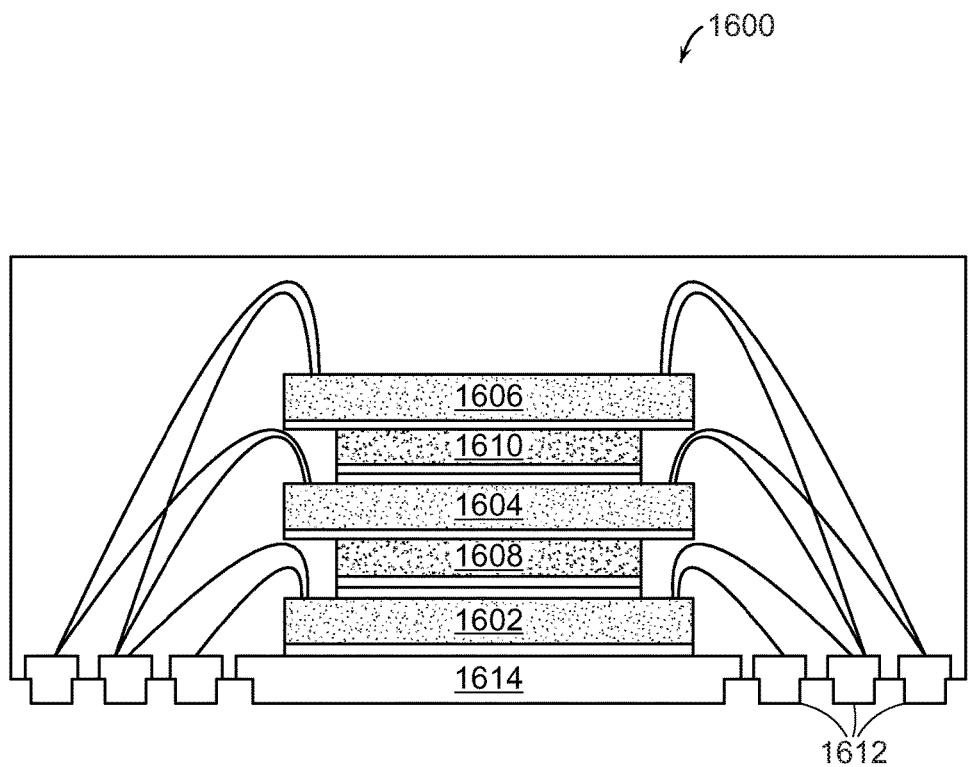
FIG. 16 is a schematic side view of a multi-chip module including an ultrasound transmit/receive IC chip, an amplifier IC chip and an ultrasound beamformer IC chip vertically integrated in a vertically stacked configuration.

FIG. 16 is a schematic side view of a multi-chip module 1600 including a TR chip 1602, an amplifier chip 1604 and a beamformer chip 1606 vertically integrated in a vertically stacked configuration on a substrate 1614. Any suitable technique illustrated in FIGS. 12-15 may be used to fabricate the multi-chip module. One of ordinary skill in the art will recognize that the particular order in which the chips are stacked may be different in other embodiments. First and second spacer layers 1608, 1610 are provided to spacedly separate the chips 1602, 1604, 1606. Each chip is coupled to a metal frame (e.g., a leadframe) 1612. In certain exemplary embodiments, heat transfer and heat sink mechanisms may be provided in the multi-chip module to sustain high temperature reliability stressing without bulk failure. Other components of FIG. 16 are described with reference to FIGS. 12 and 14.

In this exemplary embodiment, each multi-chip module may handle the complete transmit, receive, TGC amplification and beam forming operations for a large number of channels, for example, 32 channels. By vertically integrating the three silicon chips into a single multi-chip module, the space and footprint required for the printed circuit board is further reduced. A plurality of multi-chip modules may be provided on a single ultrasound engine circuit board to further increase the number of channels while minimizing the packaging size and footprint. For example, a 128 channel ultrasound engine circuit board 108 can be fabricated within exemplary planar dimensions of about 10 cm× about 10 cm, which is a significant improvement of the space requirements of conventional ultrasound circuits. A single circuit board of an ultrasound engine including one or more multi-chip modules may have 16 to 128 channels in preferred embodiments. In certain embodiments, a single circuit board of an ultrasound engine including one or more multi-chip modules may have 16, 32, 64, 128 channels, and the like.

Figure 17:
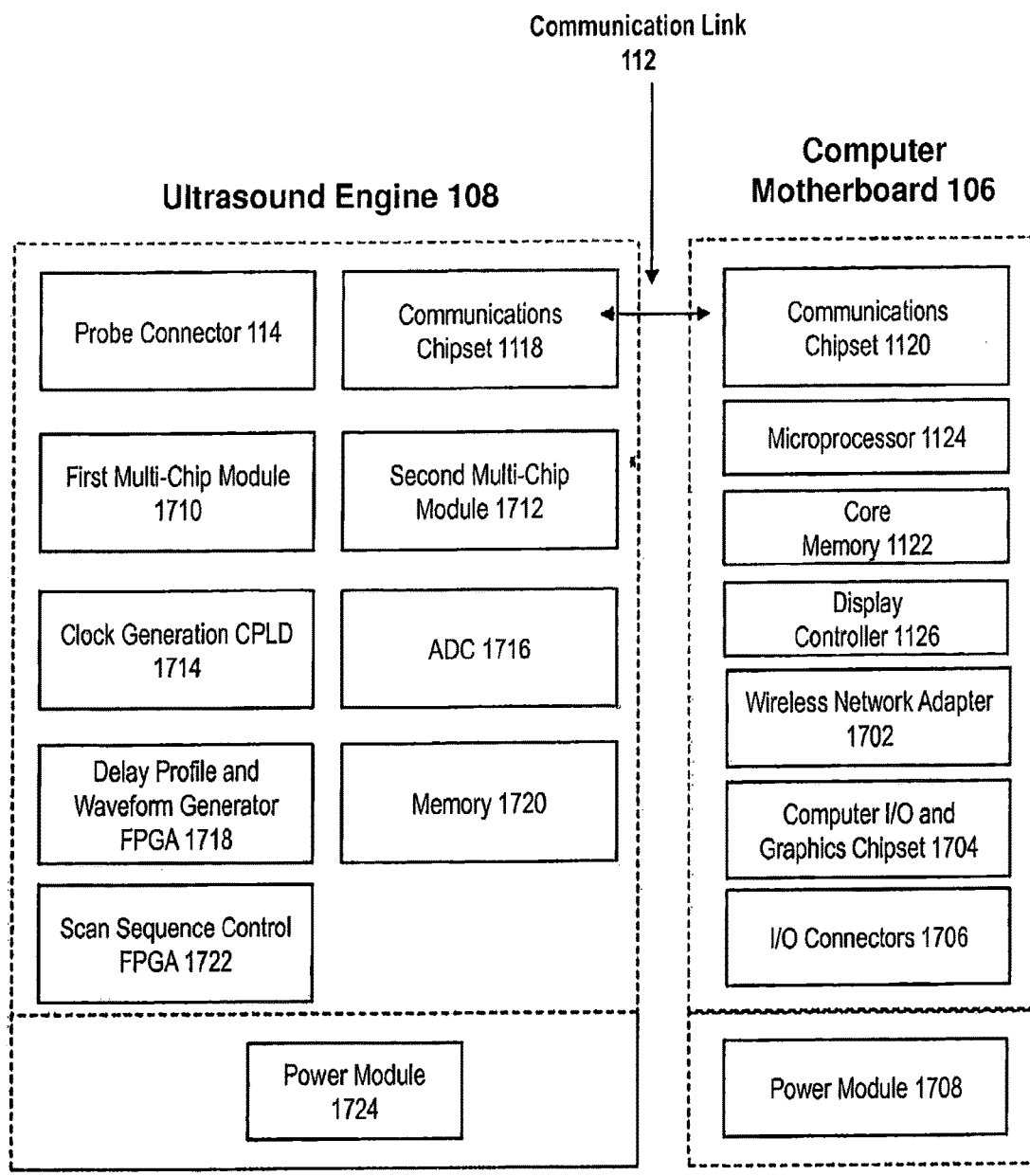
FIG. 17 is a detailed schematic block diagram of an exemplary embodiment of an ultrasound engine (i.e., the front-end ultrasound specific circuitry) and an exemplary embodiment of a computer motherboard (i.e., the host computer) provided as a single board complete ultrasound system.

FIG. 17 is a detailed schematic block diagram of an exemplary embodiment of the ultrasound engine 108 (i.e., the front-end ultrasound specific circuitry) and an exemplary embodiment of the computer motherboard 106 (i.e., the host computer) provided as a single board complete ultrasound system. An exemplary single board ultrasound system as illustrated in FIG. 17 may have exemplary planar dimensions of about 25 cm× about 18 cm, although other dimensions are possible. The single board complete ultrasound system of FIG. 17 may be implemented in the ultrasound device illustrated in FIGS. 1, 2A, 2B, and 9A, and may be used to perform the operations depicted in FIGS. 3-8, 9B, and 10.

The ultrasound engine 108 includes a probe connector 114 to facilitate the connection of at least one ultrasound probe/transducer. In the ultrasound engine 108, a TR module, an amplifier module and a beamformer module may be vertically stacked to form a multi-chip module as shown in FIG. 16, thereby minimizing the overall packaging size and footprint of the ultrasound engine 108. The ultrasound engine 108 may include a first multi-chip module 1710 and a second multi-chip module 1712, each including a TR chip, an ultrasound pulser and receiver, an amplifier chip including a time-gain control amplifier, and a sample-data beamformer chip vertically integrated in a stacked configuration as shown in FIG. 16. The first and second multi-chip modules 1710, 1712 may be stacked vertically on top of each other to further minimize the area required on the circuit board. Alternatively, the first and second multi-chip modules 1710, 1712 may be disposed horizontally on the circuit board. In an exemplary embodiment, the TR chip, the amplifier chip and the beamformer chip is each a 32-channel chip, and each multi-chip module 1710, 1712 has 32 channels. One of ordinary skill in the art will recognize that exemplary ultrasound engines 108 may include, but are not limited to, one, two, three, four, five, six, seven, eight multi-chip modules. Note that in a preferred embodiment the system can be configured with a first beamformer in the transducer housing and a second beamformer in the tablet housing.

The ASICs and the multi-chip module configuration enable a 128-channel complete ultrasound system to be implemented on a small single board in a size of a tablet computer format. An exemplary 128-channel ultrasound engine 108, for example, can be accommodated within exemplary planar dimensions of about 10 cm×about 10 cm, which is a significant improvement of the space requirements of conventional ultrasound circuits. An exemplary 128-channel ultrasound engine 108 can also be accommodated within an exemplary area of about 100 $cm^2$.

The ultrasound engine 108 also includes a clock generation complex programmable logic device (CPLD) 1714 for generating timing clocks for performing an ultrasound scan using the transducer array. The ultrasound engine 108 includes an analog-to-digital converter (ADC) 1716 for converting analog ultrasound signals received from the transducer array to digital RF formed beams. The ultrasound engine 108 also includes one or more delay profile and waveform generator field programmable gate arrays (FPGA) 1718 for managing the receive delay profiles and generating the transmit waveforms. The ultrasound engine 108 includes a memory 1720 for storing the delay profiles for ultrasound scanning. An exemplary memory 1720 may be a single DDR3 memory chip. The ultrasound engine 108 includes a scan sequence control field programmable gate array (FPGA) 1722 configured to manage the ultrasound scan sequence, transmit/receiving timing, storing and fetching of profiles to/from the memory 1720, and buffering and moving of digital RF data streams to the computer motherboard 106 via a high-speed serial interface 112. The high-speed serial interface 112 may include Fire Wire or other serial or parallel bus interface between the computer motherboard 106 and the ultrasound engine 108. The ultrasound engine 108 includes a communications chipset 1118 (e.g., a Fire Wire chipset) to establish and maintain the communications link 112.

A power module 1724 is provided to supply power to the ultrasound engine 108, manage a battery charging environment and perform power management operations. The power module 1724 may generate regulated, low noise power for the ultrasound circuitry and may generate high voltages for the ultrasound transmit pulser in the TR module.

The computer motherboard 106 includes a core computer-readable memory 1122 for storing data and/or computer-executable instructions for performing ultrasound imaging operations. The memory 1122 forms the main memory for the computer and, in an exemplary embodiment, may store about 4 Gb of DDR3 memory. The memory 1122 may include a solid state hard drive (SSD) for storing an operating system, computer-executable instructions, programs and image data. An exemplary SSD may have a capacity of about 128 GB.

The computer motherboard 106 also includes a microprocessor 1124 for executing computer-executable instructions stored on the core computer-readable memory 1122 for performing ultrasound imaging processing operations. Exemplary operations include, but are not limited to, down conversion, scan conversion, Doppler processing, Color Flow processing, Power Doppler processing, Spectral Doppler processing, and post signal processing. An exemplary microprocessor 1124 may be an off-the-shelf commercial computer processor, such as an Intel Core-i5 processor. Another exemplary microprocessor 1124 may be a digital signal processor (DSP) based processor, such as DaVinci™ processors from Texas Instruments.

The computer motherboard 106 includes an input/output (I/O) and graphics chipset 1704 which includes a co-processor configured to control I/O and graphic peripherals such as USB ports, video display ports and the like. The computer motherboard 106 includes a wireless network adapter 1702 configured to provide a wireless network connection. An exemplary adapter 1702 supports 802.11g and 802.11n standards. The computer motherboard 106 includes a display controller 1126 configured to interface the computer motherboard 106 to the display 104. The computer motherboard 106 includes a communications chipset 1120 (e.g., a Fire Wire chipset or interface) configured to provide a fast data communication between the computer motherboard 106 and the ultrasound engine 108. An exemplary communications chipset 1120 may be an IEEE 1394b 800 Mbit/sec interface. Other serial or parallel interfaces 1706 may alternatively be provided, such as USB3, Thunder-Bolt, PCIe, and the like. A power module 1708 is provided to supply power to the computer motherboard 106, manage a battery charging environment and perform power management operations.

An exemplary computer motherboard 106 may be accommodated within exemplary planar dimensions of about 12 cm×about 10 cm. An exemplary computer motherboard 106 can be accommodated within an exemplary area of about 120 $cm^2$.

Figure 18:
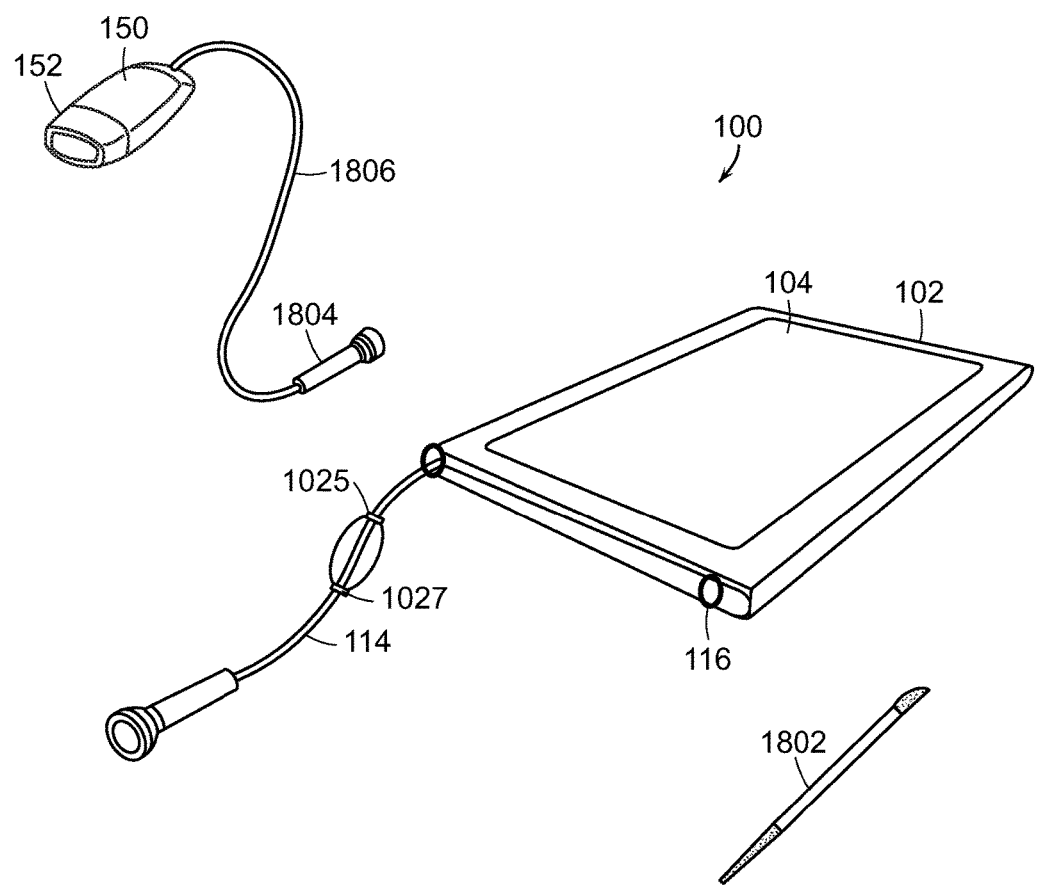
FIG. 18 is a perspective view of an exemplary portable ultrasound system provided in accordance with exemplary embodiments.

FIG. 18 is a perspective view of an exemplary portable ultrasound system 100 provided in accordance with exemplary embodiments. The system 100 includes a housing 102 that is in a tablet form factor as illustrated in FIG. 18, but that may be in any other suitable form factor. An exemplary housing 102 may have a thickness below 2 cm and preferably between 0.5 and 1.5 cm. A front panel of the housing 102 includes a multi-touch LCD touch screen display 104 that is configured to recognize and distinguish one or more multiple and/or simultaneous touches on a surface of the touch screen display 104. The surface of the display 104 may be touched using one or more of a user's fingers, a user's hand or an optional stylus 1802. The housing 102 includes one or more I/O port connectors 116 which may include, but are not limited to, one or more USB connectors, one or more SD cards, one or more network mini display ports, and a DC power input. The embodiment of housing 102 in FIG. 18 can also be configured within a palm-carried form factor having dimensions of 150 mm×100 mm×15 mm (a volume of 225000 $mm^3$) or less. The housing 102 can have a weight of less than 200 g. Optionally, cabling between the transducer array and the display housing can include interface circuitry 1020 as described herein. The interface circuitry 1020 can include, for example, beamforming circuitry and/or A/D circuitry in a pod that dangles from the tablet. Separate connectors 1025, 1027 can be used to connect the dangling pod to the transducer probe cable. The connector 1027 can include probe identification circuitry as described herein. The unit 102 can include a camera, a microphone and a speaker as well as wireless telephone circuitry for voice and data communications as well as voice activated software that can be used to control the ultrasound imaging operations described herein.

The housing 102 includes or is coupled to a probe connector 114 to facilitate connection of at least one ultrasound probe/transducer 150. The ultrasound probe 150 includes a transducer housing including one or more transducer arrays 152. The ultrasound probe 150 is couplable to the probe connector 114 using a housing connector 1804 provided along a flexible cable 1806. One of ordinary skill in the art will recognize that the ultrasound probe 150 may be coupled to the housing 102 using any other suitable mechanism, for example, an interface housing that includes circuitry for performing ultrasound-specific operations like beamforming. Other exemplary embodiments of ultrasound systems are described in further detail in WO 03/079038 A2, filed Mar. 11, 2003, titled "Ultrasound Probe with Integrated Electronics," the entire contents of which is expressly incorporated herein by reference. Preferred embodiments can employ a wireless connection between the hand-held transducer probe 150 and the display housing. Beamformer electronics can be incorporated into probe housing 150 to provide beamforming of subarrays in a 1D or 2D transducer array as described herein. The display housing can be sized to be held in the palm of the user's hand and can include wireless network connectivity to public access networks such as the internet.

Figure 19:
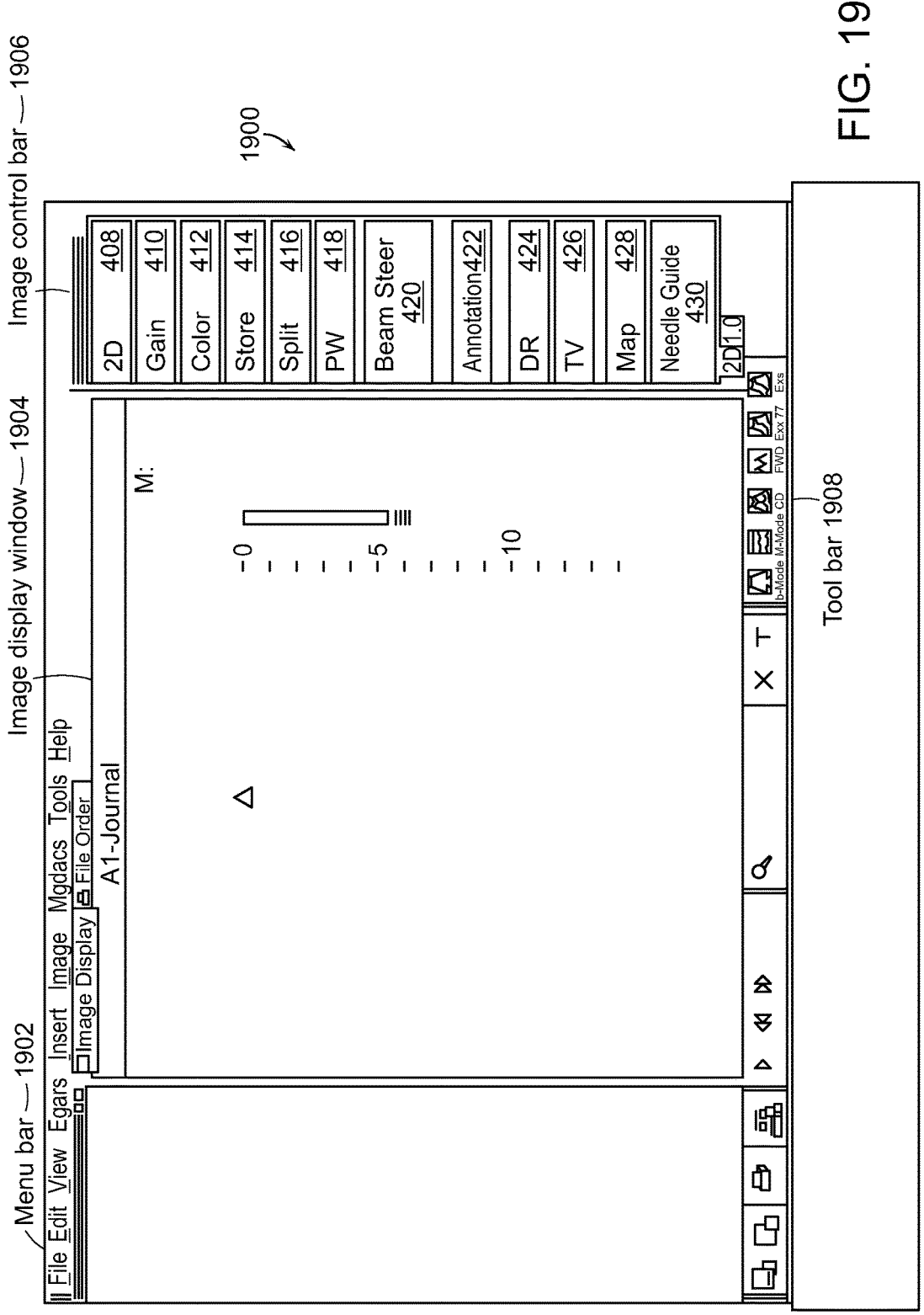
FIG. 19 illustrates an exemplary view of a main graphical user interface (GUI) rendered on a touch screen display of the exemplary portable ultrasound system of FIG. 18.

FIG. 19 illustrates an exemplary view of a main graphical user interface (GUI) 1900 rendered on the touch screen display 104 of the portable ultrasound system 100 of FIG. 18. The main GUI 1900 may be displayed when the ultrasound system 100 is started. To assist a user in navigating the main GUI 1900, the GUI may be considered as including four exemplary work areas: a menu bar 1902, an image display window 1904, an image control bar 1906, and a tool bar 1908. Additional GUI components may be provided on the main GUI 1900 to, for example, enable a user to close, resize and exit the GUI and/or windows in the GUI.

The menu bar 1902 enables a user to select ultrasound data, images and/or videos for display in the image display window 1904. The menu bar 1902 may include, for example, GUI components for selecting one or more files in a patient folder directory and an image folder directory. The image display window 1904 displays ultrasound data, images and/or videos and may, optionally, provide patient information. The tool bar 1908 provides functionalities associated with an image or video display including, but not limited to, a save button for saving the current image and/or video to a file, a save Loop button that saves a maximum allowed number of previous frames as a Cine loop, a print button for printing the current image, a freeze image button for freezing an image, a playback toolbar for controlling aspects of playback of a Cine loop, and the like. Exemplary GUI functionalities that may be provided in the main GUI 1900 are described in further detail in WO 03/079038 A2, filed Mar. 11, 2003, titled "Ultrasound Probe with Integrated Electronics," the entire contents of which are expressly incorporated herein by reference.

The image control bar 1906 includes touch controls that may be operated by touch and touch gestures applied by a user directly to the surface of the display 104. Exemplary touch controls may include, but are not limited to, a 2D touch control 408, a gain touch control 410, a color touch control 412, a storage touch control 414, a split touch control 416, a PW imaging touch control 418, a beamsteering touch control 20, an annotation touch control 422, a dynamic range operations touch control 424, a Teravision™ touch control 426, a map operations touch control 428, and a needle guide touch control 428. These exemplary touch controls are described in further detail in connection with FIGS. 4a-4c.

Figure 20:
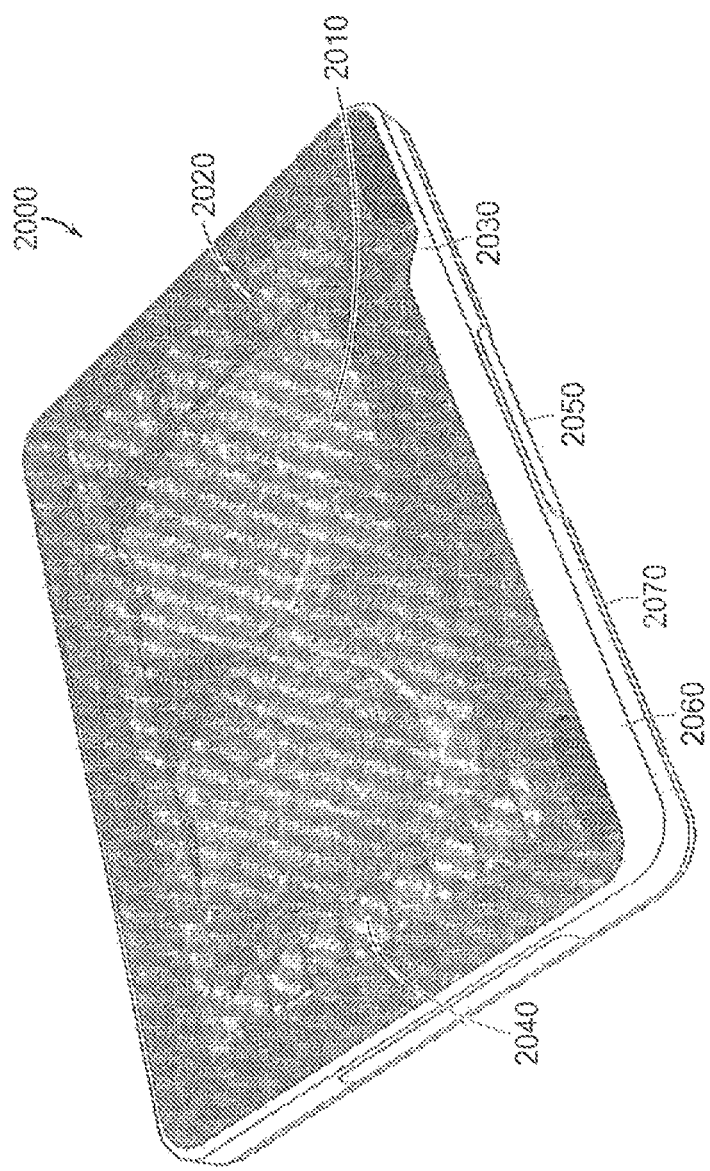
FIG. 20 is a top view of the medical ultrasound imaging system in accordance with another preferred embodiment of the invention.

FIG. 20 depicts an illustrative embodiment of exemplary medical ultrasound imaging equipment 2000, implemented in the form factor of a tablet in accordance with the invention. The table may have the dimensions of 12.5"× 1.25"×8.75" or 31.7 cm×3.175 cm×22.22 cm but it may also be in any other suitable form factor having a volume of less than 2500 cm$^3$ and a weight of less than 8 lbs. As shown in FIG. 20, the medical ultrasound imaging equipment 2000, includes a housing 2030, a touch screen display 2010, wherein ultrasound images 2010, and ultra sound data 2040, can be displayed and ultrasound controls 2020, are configured to be controlled by a touchscreen display 2010. The housing 2030, may have a front panel 2060 and a rear panel 2070. The touchscreen display 2010, forms the front panel 2060, and includes a multi-touch LCD touch screen that can recognize and distinguish one or more multiple and or simultaneous touches of the user on the touchscreen display 2010. The touchscreen display 2010 may have a capacitive multi-touch and AVAH LCD screen. For example, the capacitive multi-touch and AVAH LCD screen may enable a user to view the image from multi angles without losing resolution. In another embodiment, the user may utilize a stylus for data input on the touch screen. The tablet can include an integrated foldable stand that permits a user to swivel the stand from a storage position that conforms to the tablet form factor so that the device can lay flat on the rear panel, or alternatively, the user can swivel the stand to enable the tablet to stand at an upright position at one of a plurality of oblique angles relative to a support surface.

Capacitive touchscreen module comprises an insulator for example glass, coated with a transparent conductor, such as indium tin oxide. The manufacturing process may include a bonding process among glass, x-sensor film, y-sensor film and a liquid crystal material. The tablet is configured to allow a user to perform multi-touch gestures such as pinching and stretching while wearing a dry or a wet glove. The surface of the screen registers the electrical conductor making contact with the screen. The contact distorts the screens electrostatic field resulting in measurable changes in capacitance. A processor then interprets the change in the electrostatic field. Increasing levels of responsiveness are enabled by reducing the layers and by producing touch screens with "in-cell" technology. "In-cell" technology eliminates layers by placing the capacitors inside the display. Applying "in-cell" technology reduces the visible distance between the user's finger and the touchscreen target, thereby creating a more directive contact with the content displayed and enabling taps and gestures to have an increase in responsiveness.

Figure 21:
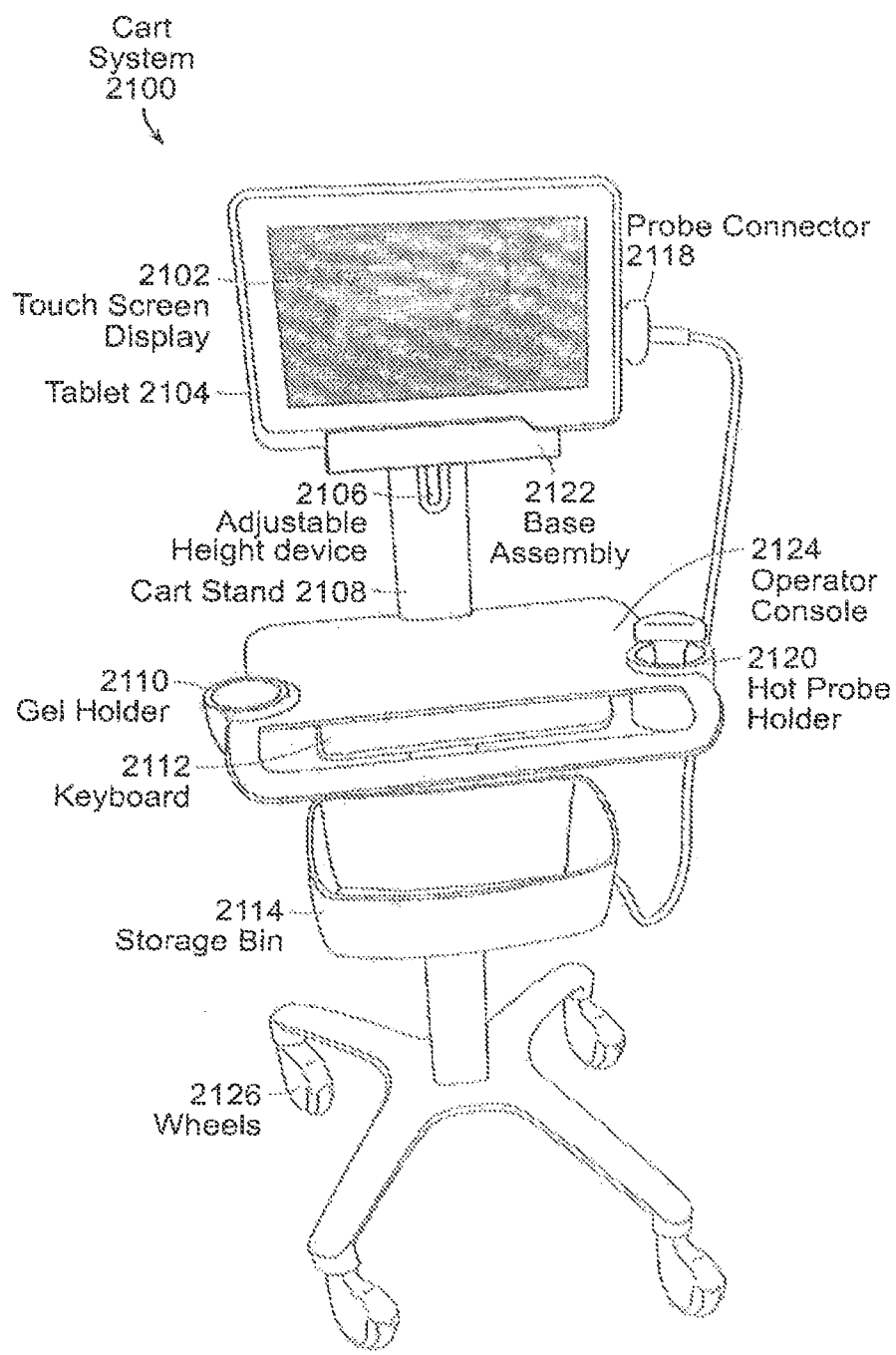
FIG. 21 illustrates a preferred cart system for a tablet ultrasound system in accordance with preferred embodiment 9 of the invention.

FIG. 21 illustrates a preferred cart system for a modular ultrasound imaging system in accordance with the invention. The cart system 2100 uses a base assembly 2122 including a docking bay that receives the tablet. The cart configuration 2100 is configured to dock tablet 2104, including a touch screen display 2102, to a cart 2108, which can include a full operator console 2124. After the tablet 2104, is docked to the cart stand 2108, the system forms a full feature roll about system. The full feature roll about system may include, an adjustable height device 2106, a gel holder 2110, and a storage bin 2114, a plurality of wheels 2116, a hot probe holder 2120, and the operator console 2124. The control devices may include a keyboard 2112 on the operator console 2124 that may also have other peripherals added such as a printer or a video interface or other control devices.

Figure 22:
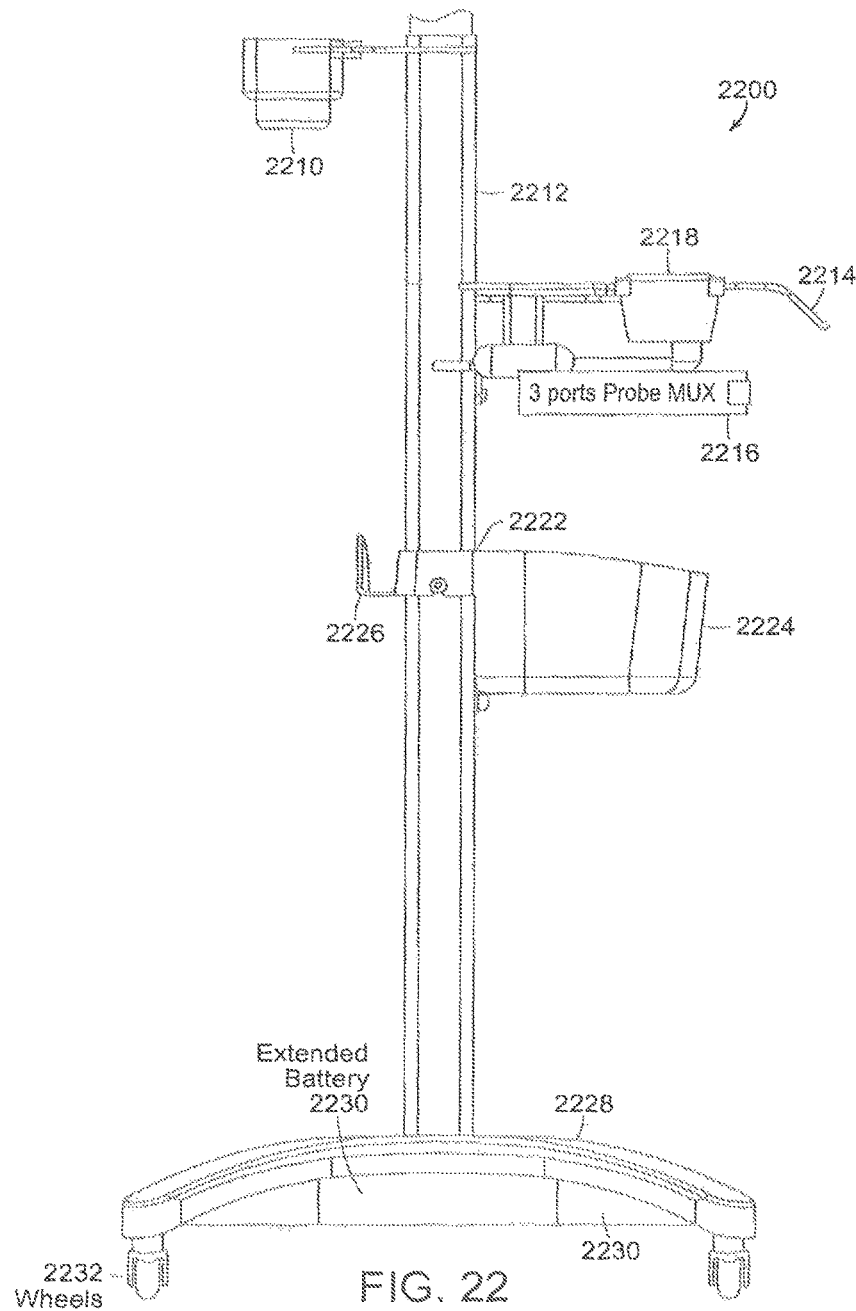
FIG. 22 illustrates preferred cart system for a modular ultrasound imaging system in accordance with preferred embodiments of the invention.

FIG. 22 illustrate a preferred cart system, for use in embodiments with a modular ultrasound imaging system in accordance with the invention. The cart system 2200 may be configured with a vertical support member 2212, coupled to a horizontal support member 2028. An auxiliary device connector 2018, having a position for auxiliary device attachment 2014, may be configured to connect to the vertical support member 2212. A 3 port Probe MUX connection device 2016 may also be configured to connect to the tablet. A storage bin 2224 can be configured to attach by a storage bin attachment mechanism 2222, to vertical support member 2212. The cart system may also include a cord management system 2226, configured to attach to the vertical support member. The cart assembly 2200 includes the support beam 2212 mounted on a base 2228 having wheels 2232 and a battery 2230 that provides power for extended operation of the tablet. The assembly can also include an accessory holder 2224 mounted with height adjustment device 2226. Holders 2210, 2218 can be mounted on beam 2212 or on console panel 2214. The multiport probe multiplex device 2216 connects to the tablet to provide simultaneous connection of several transducer probes which the user can select in sequence with the displayed virtual switch. A moving touch gesture, such as a three finger flick on the displayed image or touching of a displayed virtual button or icon can switch between connected probes.

Figure 23:
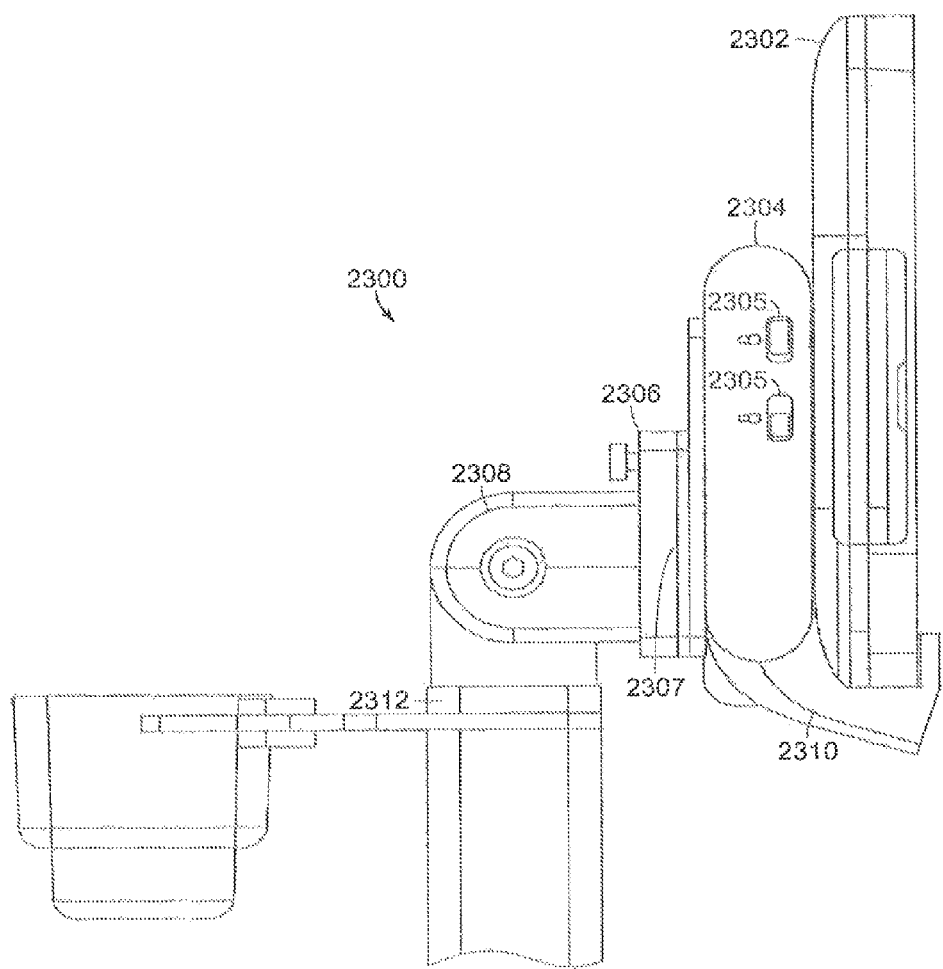
FIG. 23 illustrates preferred cart system for a modular ultrasound imaging system in accordance with preferred embodiments of the invention.

FIG. 23 illustrates preferred cart mount system for a modular ultrasound imaging system in accordance with the invention. Arrangement 2300 depicts the tablet 2302, coupled to the docking station 2304. The docking station 2304 is affixed to the attachment mechanism 2306. The attachment mechanism 2306 may include a hinged member 2308, allowing for the user display to tilted into a user desired position. The attachment mechanism 2306 is attached to the vertical member 2312. A tablet 2302 as described herein can be mounted on the base docking unit 2304 which is mounted to a mount assembly 2306 on top of beam 2212. The base unit 2304 includes cradle 2310, electrical connectors 2305 and a port 2307 to connect to the system 2302 to battery 2230 and multiplexor device 2216.

Figure 24:
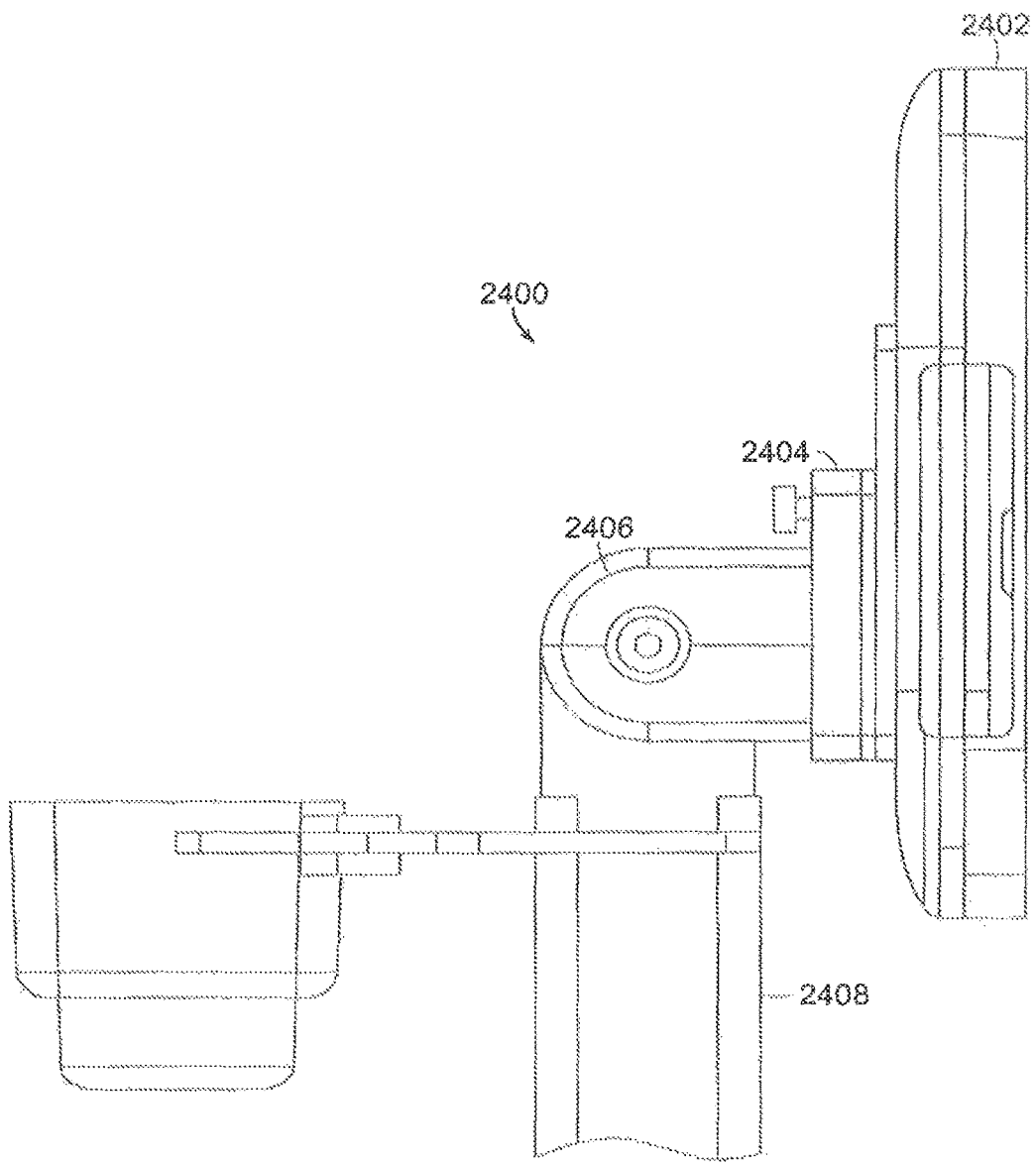
FIG. 24 illustrates preferred cart system for a modular ultrasound imaging system in accordance with preferred embodiments of the invention.

FIG. 24 illustrates preferred cart system 2400 modular ultrasound imaging system in accordance with the invention in which tablet 2402 is connected on mounting assembly 2406 with connector 2404. Arrangement 2400 depicts the tablet 2402, coupled to the vertical support member 2408, via attachment mechanism 2404 without the docking element 2304. Attachment mechanism 2404 may include a hinged member 2406 for display adjustment.

Figure 25:
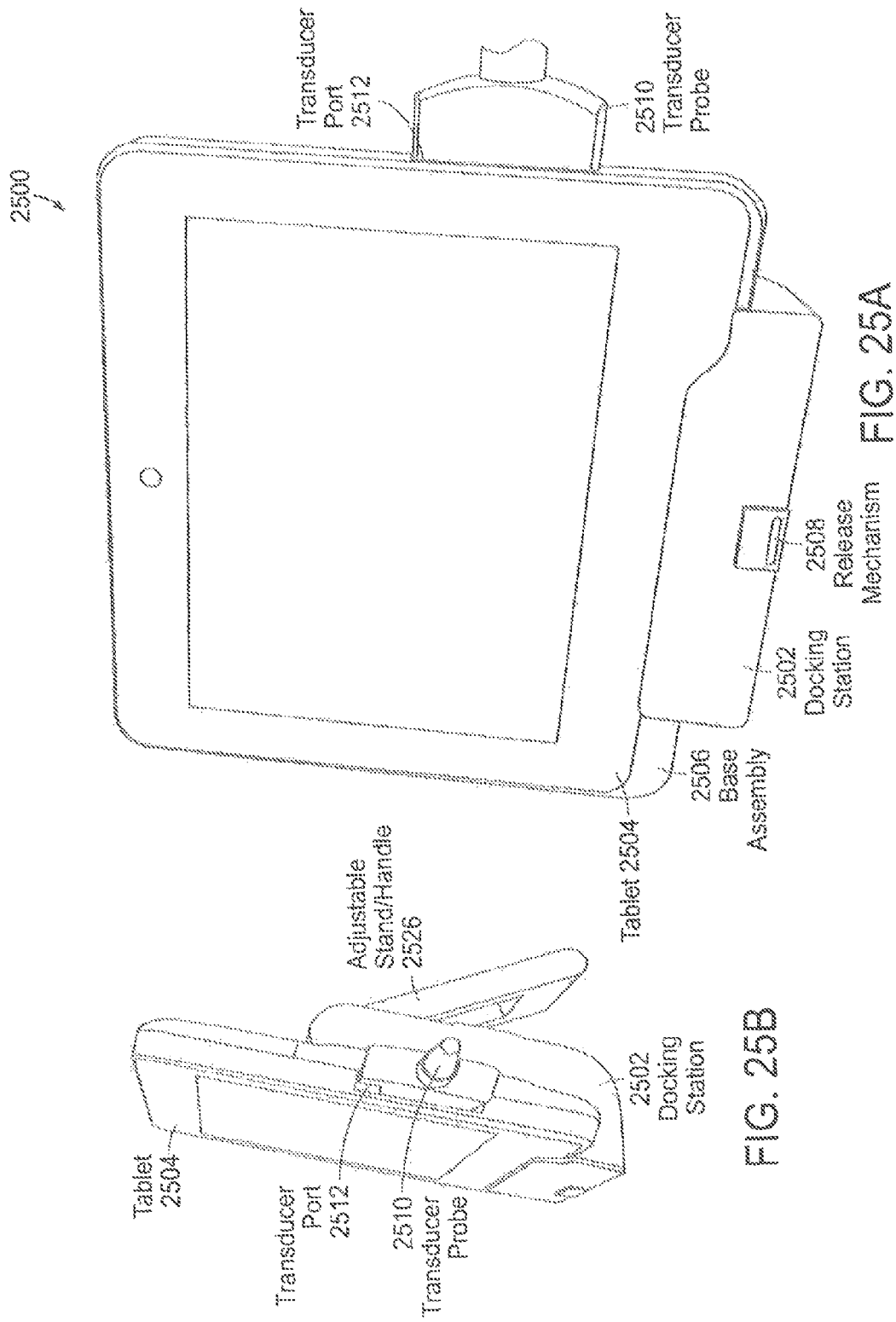
FIGS. 25A-25B illustrate a multifunction docking base for tablet ultrasound device.

FIGS. 25A and 25B illustrate a multi-function docking station. FIG. 25A illustrates docking station 2502, and tablet 2504, having a base assembly 2506, that mates to the docking station 2502. The tablet 2504, and the docking station 2502, may be electrically connected. The tablet 2504 may be released from docking station 2502, by engaging the release mechanism 2508. The docking station 2502 may contain a transducer port 2512, for connection of a transducer probe 2510. The docking station 2502 can contain 3 USB 3.0 ports, a LAN port, a headphone jack and a power connector for charging. FIG. 25B illustrates a side view of the tablet 2504, and docking station 2502, having a stand in accordance with the preferred embodiments of the present invention. The docking station may include an adjustable stand/handle 2526. The adjustable stand/handle 2526 may be tilted for multiple viewing angles. The adjustable stand/handle 2526 may be flipped up for transport purposes. The side view also illustrates a transducer port 2512, and a transducer probe connector 2510.

Figure 26:
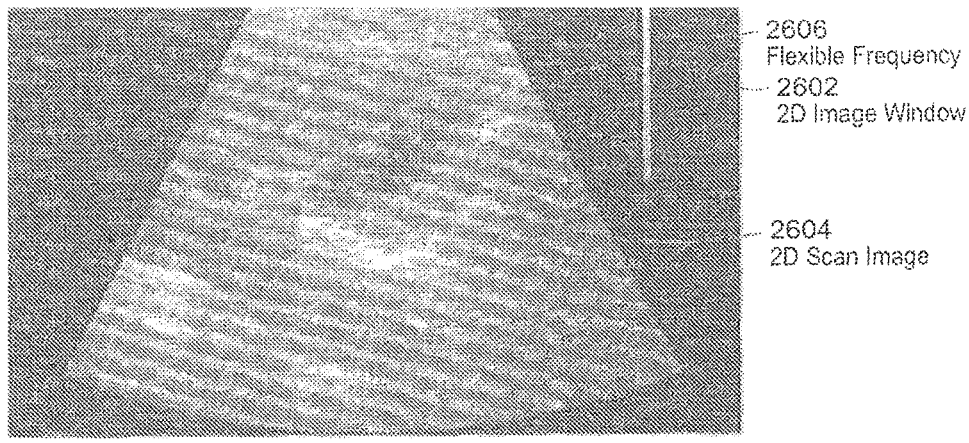
FIG. 26 illustrates a 2D imaging mode of operation with a modular ultrasound imaging system in accordance with the invention.

FIG. 26 illustrates a 2D imaging mode of operation with a modular ultrasound imaging system in accordance with the invention. The touch screen of table 2504 may display images obtained by 2-dimensional transducer probe using a 256 digital beamformer channels. The 2-dimensional image window 2602 depicts a 2-dimensional image scan 2604. The 2-dimensional image may be obtained using flexible frequency scans 2606, wherein the control parameters are represented on the tablet.

Figure 27:
FIG. 27 illustrates a motion mode of operation with a modular ultrasound imaging system in accordance with the invention.

FIG. 27 illustrates a motion mode of operation with a modular ultrasound imaging system in accordance with the invention. The touch screen display of tablet 2700, may display images obtained by a motion mode of operation. The touch screen display of tablet 2700, may simultaneously display 2-dimensional 2706, and motion mode imaging 2708. The touch screen display of tablet 2700, may display a 2-dimensional image window 2704, with a 2-dimensional image 2706. Flexible frequency controls 2702 displayed with the graphical user interface can be used to adjust the frequency from 2 MHz to 12 MHz.

Figure 28:
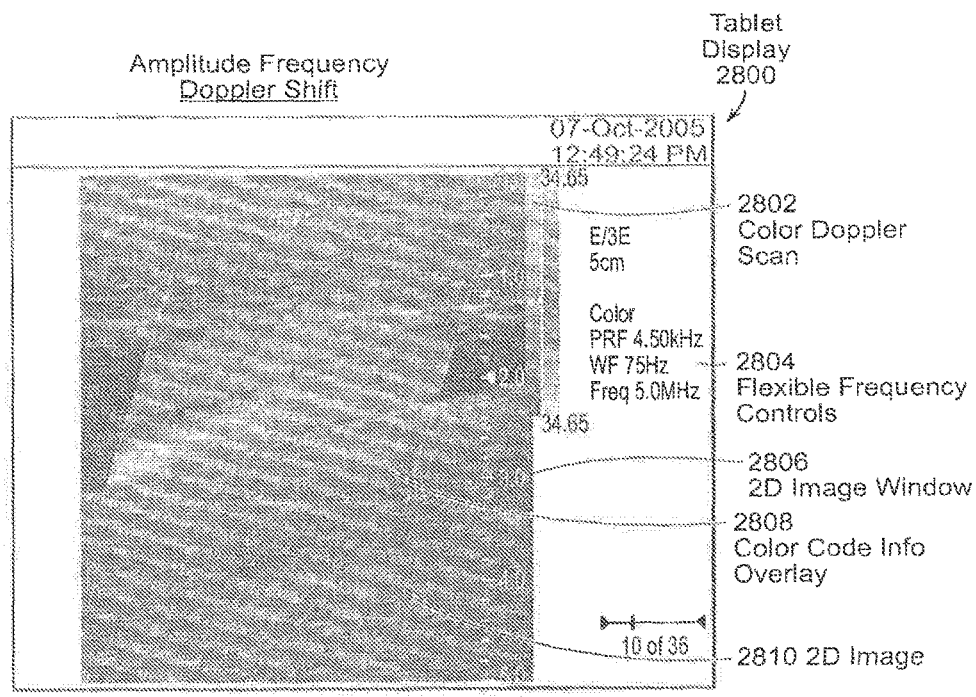
FIG. 28 illustrates a color Doppler mode of operation with a modular ultrasound imaging system in accordance with the invention.

FIG. 28 illustrates a color Doppler mode of operation with a modular ultrasound imaging system in accordance with the invention. The touch screen display of tablet 2800 displays images obtained by color Doppler mode of operation. A 2-dimensional image window 2806 is used as the base display. The color coded information 2808, is overlaid on the 2-dimensional image 2810. Ultrasound-based imaging of red blood cells are derived from the received echo of the transmitted signal. The primary characteristics of the echo signal are the frequency and the amplitude. Amplitude depends on the amount of moving blood within the volume sampled by the ultrasound beam. A high frame rate or high resolution can be adjusted with the display to control the quality of the scan. Higher frequencies may be generated by rapid flow and can be displayed in lighter colors, while lower frequencies are displayed in darker colors. Flexible frequency controls 2804, and color Doppler scan information 2802, may be displayed on the tablet display 2800.

Figure 29:
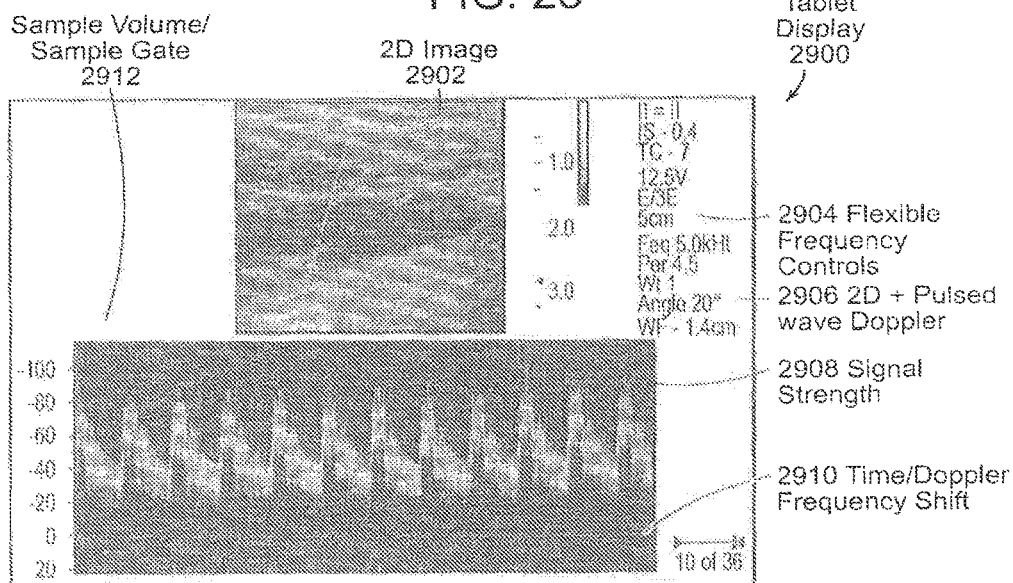
FIG. 29 illustrates a pulsed-wave Doppler mode of operation with a modular ultrasound imaging system in accordance with the invention.

FIG. 29 illustrates a Pulsed wave Doppler mode of operation with a modular ultrasound imaging system in accordance with the invention. The touch screen display of tablet 2900, may display images obtained by pulsed wave Doppler mode of operation. Pulsed wave Doppler scans produce a series of pulses used to analyse the motion of blood flow in a small region along a desired ultrasound cursor called the sample volume or sample gate 2012. The tablet display 2900 may depict a 2-dimensional image 2902, wherein the sample volume/sample gate 2012 is overlaid. The tablet display 2900 may use a mixed mode of operation 2906, to depict a 2-dimensional image 2902, and a time/doppler frequency shift 2910. The time/doppler frequency shift 2910 can be converted into velocity and flow if an appropriate angle between the beam and blood flow is known. Shades of gray 2908, in the time/doppler frequency shift 2910, may represent the strength of signal. The thickness of the spectral signal may be indicative of laminar or turbulent flow. The tablet display 2900 can depict adjustable frequency controls 2904.

Figure 30:
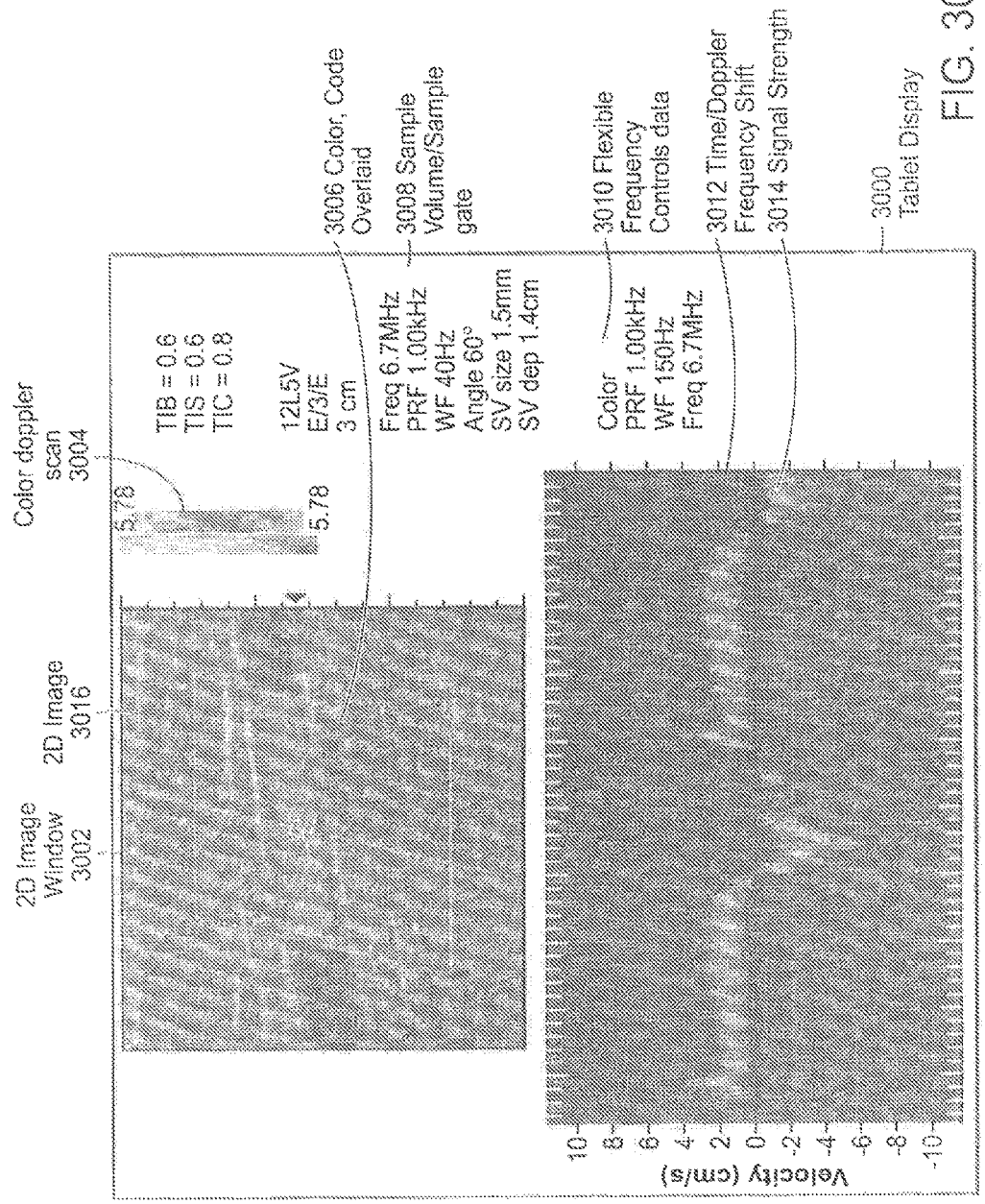
FIG. 30 illustrates a Triplex scan mode of operation with a modular ultrasound imaging system in accordance with the invention.

FIG. 30 illustrates a triplex scan mode of operation with a modular ultrasound imaging system in accordance with the invention. The tablet display 3000 may include a 2-dimensional window 3002, capable of displaying 2-dimensional images alone or in combination with the color Doppler or directional Doppler features. The touch screen display of tablet 3000, may display images obtained by color Doppler mode of operation. A 2-dimensional image window 3002 is used as the base display. The color coded information 3004, is overlaid 3006, on the 2-dimensional image 3016. The pulsed wave Doppler feature may be used alone or in combination with 2-dimensional imaging or the color Doppler imaging. The tablet display 3000 may include a pulsed wave Doppler scan represented by a sample volume/sample gate 3008, overlaid over 2 dimensional images 3016, or the color code overlaid 3006, either alone or in combination. The tablet display 3000 may depict a split screen representing the time/doppler frequency shift 3012. The time/doppler frequency shift 3012 can be converted into velocity and flow if an appropriate angle between the insolating beam and blood flow is known. Shades of gray 3014, in the time/doppler frequency shift 3012, may represent the strength of signal. The thickness of the spectral signal may be indicative of laminar or turbulent flow. The tablet display 3000 also may depict flexible frequency controls 3010.

Figure 31:
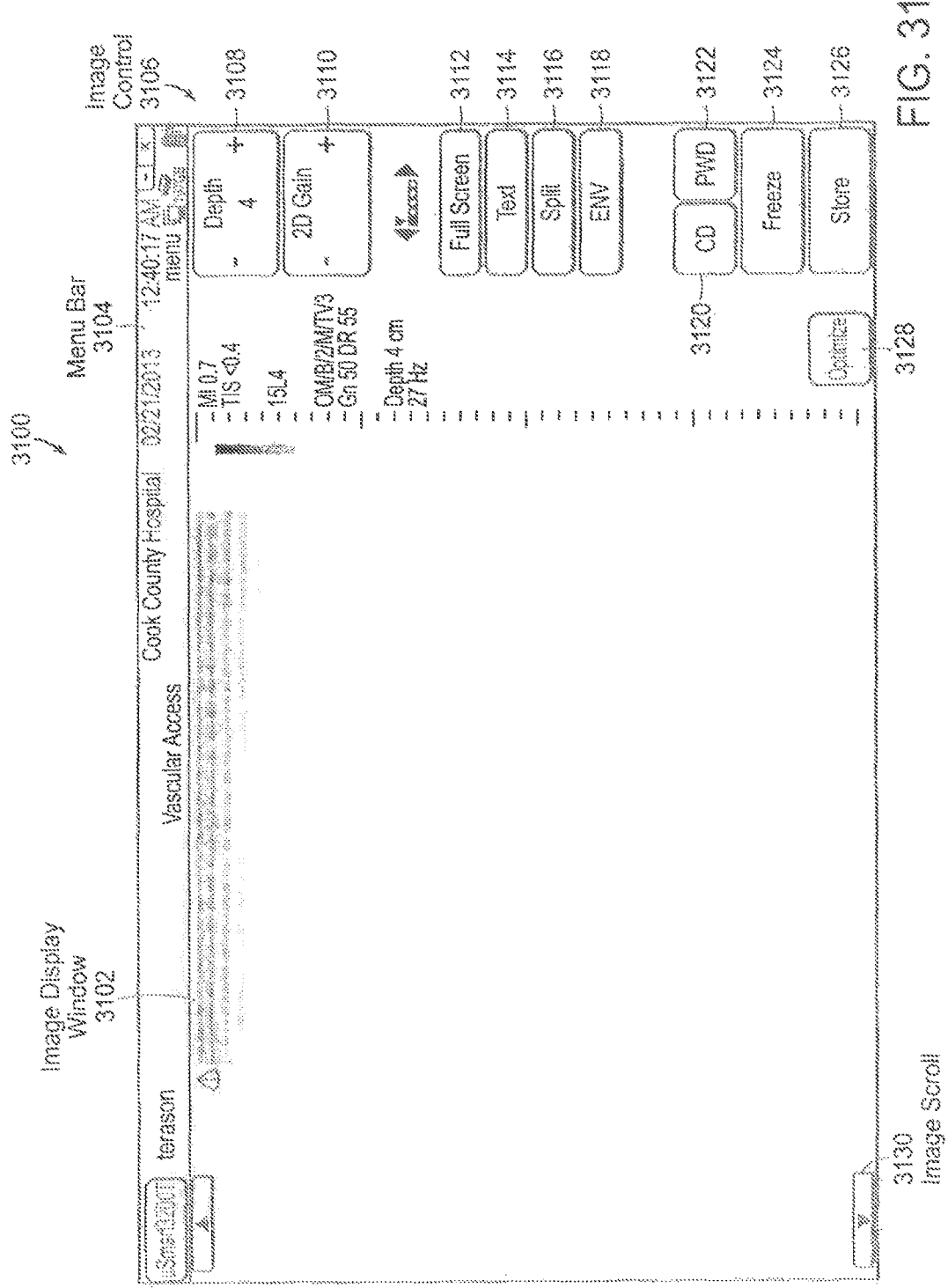
FIG. 31 illustrates a GUI Home Screen interface for a user mode of operation with a modular ultrasound imaging system in accordance with the invention.

FIG. 31 illustrates a GUI home screen interface 3100, for a user mode of operation, with a modular ultrasound imaging system in accordance with the invention. The screen interface for a user mode of operation 3100 may be displayed when the ultrasound system is started. To assist a user in navigating the GUI home screen 3100, the home screen may be considered as including three exemplary work areas: a menu bar 3104, an image display window 3102, and an image control bar 3106. Additional GUI components may be provided on the main GUI home screen 3100, to enable a user to close, resize and exit the GUI home screen and/or windows in the GUI home screen.

The menu bar 3104 enables users to select ultrasound data, images and/or video for display in the image display window 3102. The menu bar may include components for selecting one or more files in a patient folder directly and an image folder directory.

The image control bar 3106 includes touch controls that may be operated by touch and touch gestures applied by the user directly to the surface of the display. Exemplary touch controls may include, but are not limited to a depth control touch controls 3108, a 2-dimensional gain touch control 3110, a full screen touch control 3112, a text touch control 3114, a split screen touch control 3116, a ENV touch control 3118, a CD touch control 3120, a PWD touch control 3122, a freeze touch control 3124, a store touch control 3126, and a optimize touch control 3128.

Figure 32:
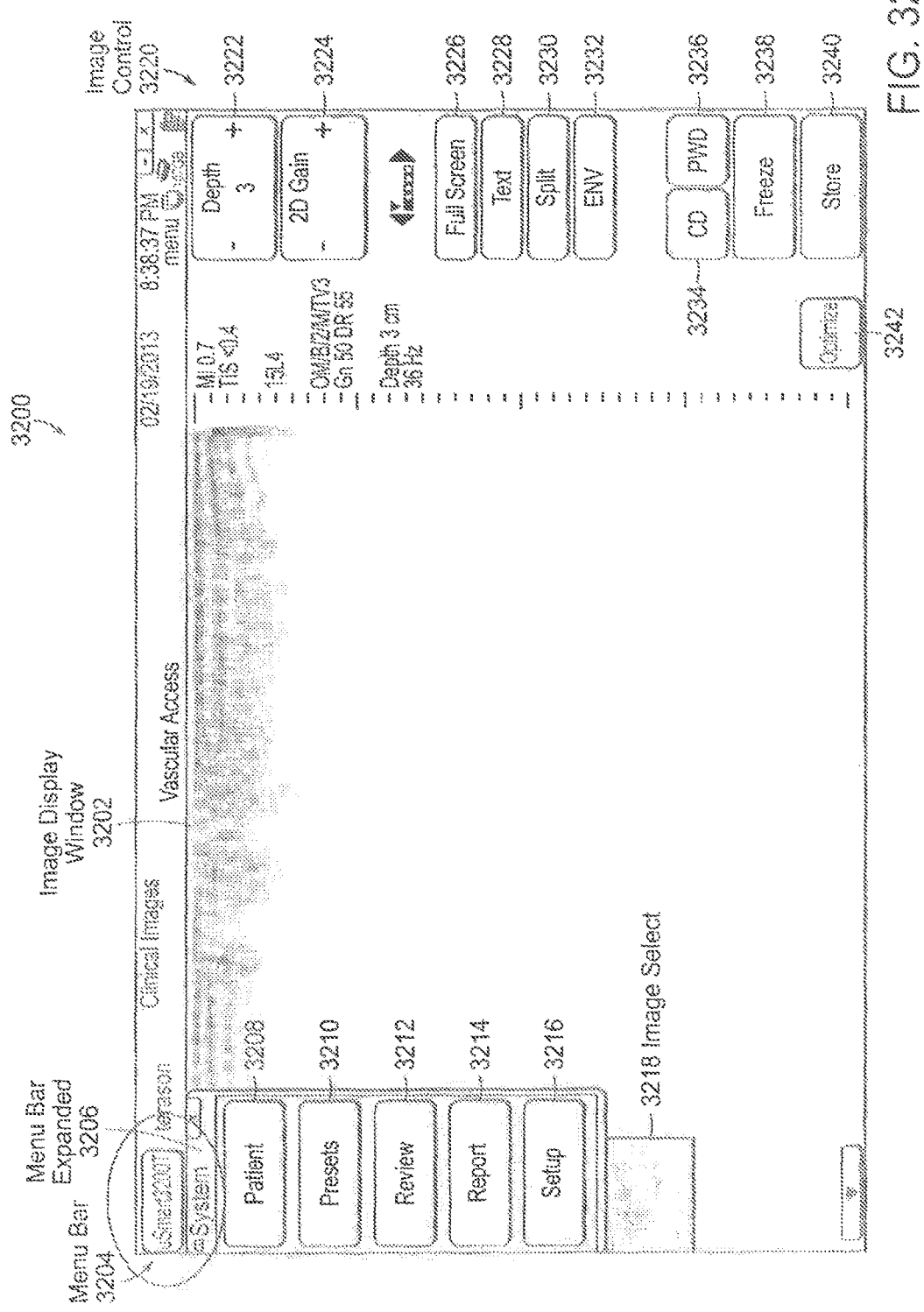
FIG. 32 illustrates a GUI Menu Screen Interface for a user mode of operation with a modular ultrasound imaging system in accordance with the invention.

FIG. 32 illustrates a GUI menu screen interface 3200, for a user mode of operation, with a modular ultrasound imaging system in accordance with the invention. The screen interface for a user mode of operation 3200 may be displayed when the menu selection mode is triggered from the menu bar 3204 thereby initiating operation of the ultrasound system. To assist a user in navigating the GUI home screen 3100, the home screen may be considered as including three exemplary work areas: a menu bar 3204, an image display window 3202, and an image control bar 3220. Additional GUI components may be provided on the main GUI menu screen 3200 to enable a user to close, resize and exit the GUI menu screen and/or windows in the GUI menu screen, for example.

The menu bar 3204 enables users to select ultra sound data, images and/or video for display in the image display window 3202. The menu bar 3204 may include touch control components for selecting one or more files in a patient folder directory and an image folder directory. Depicted in an expanded format, the menu bar may include exemplary touch control such as, a patient touch control 3208, a pre-sets touch control 3210, a review touch control 3212, a report touch control 3214, and a setup touch control 3216.

The image control bar 3220 includes touch controls that may be operated by touch and touch gestures applied by the user directly to the surface of the display. Exemplary touch controls may include, but are not limited to depth control touch controls 3222, a 2-dimensional gain touch control 3224, a full screen touch control 3226, a text touch control 3228, a split screen touch control 3230, a needle visualization ENV touch control 3232, a CD touch control 3234, a PWD touch control 3236, a freeze touch control 3238, a store touch control 3240, and a optimize touch control 3242.

Figure 33:
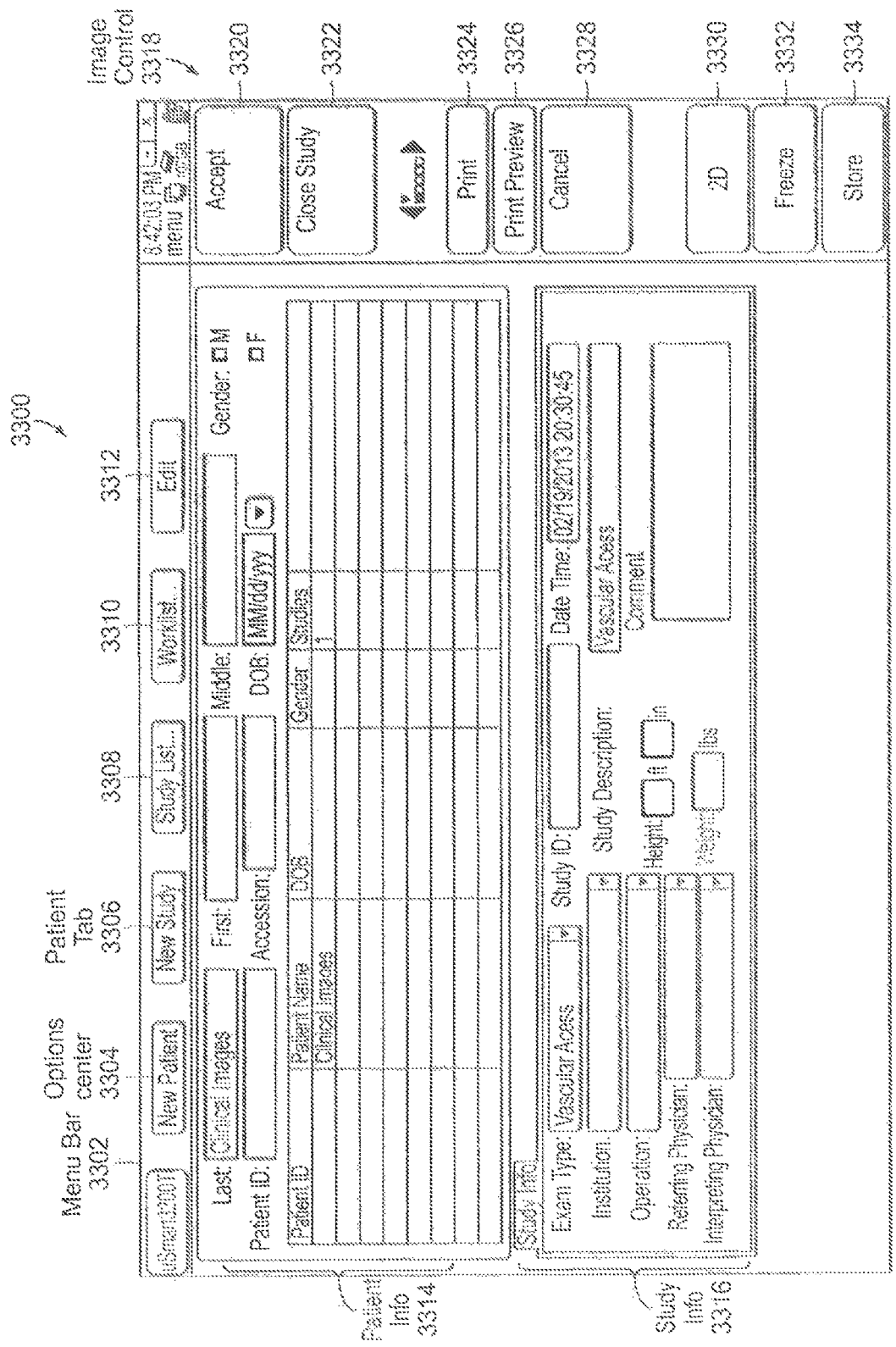
FIG. 33 illustrates a GUI Patient Data Screen Interface for a user mode of operation with a modular ultrasound imaging system in accordance with the invention.

FIG. 33 illustrates a GUI patient data screen interface 3300, for a user mode of operation, with a modular ultrasound imaging system in accordance with the invention. The screen interface for a user mode of operation 3300, may be displayed when the patient selection mode is triggered from the menu bar 3302, when the ultrasound system is started. To assist a user in navigating the GUI patient data screen 3300, the patient data screen may be considered as including five exemplary work areas: a new patient touch screen control 3304, a new study touch screen control 3306, a study list touch screen control 3308, a work list touch screen control 3310, and an edit touch screen control 3312. Within each touch screen control, further information entry fields are available 3314, 3316. For example, patient information section 3314, and study information section 3316, may be used to record data.

Within the patient data screen 3300, the image control bar 3318, includes touch controls that may be operated by touch and touch gestures applied by the user directly to the surface of the display. Exemplary touch controls may include, but are not limited to accept study touch control 3320, close study touch control 3322, print touch control 3324, print preview touch control 3326, cancel touch control 3328, a 2-dimensional touch control 3330, freeze touch control 3332, and a store touch control 3334.

Figure 34:
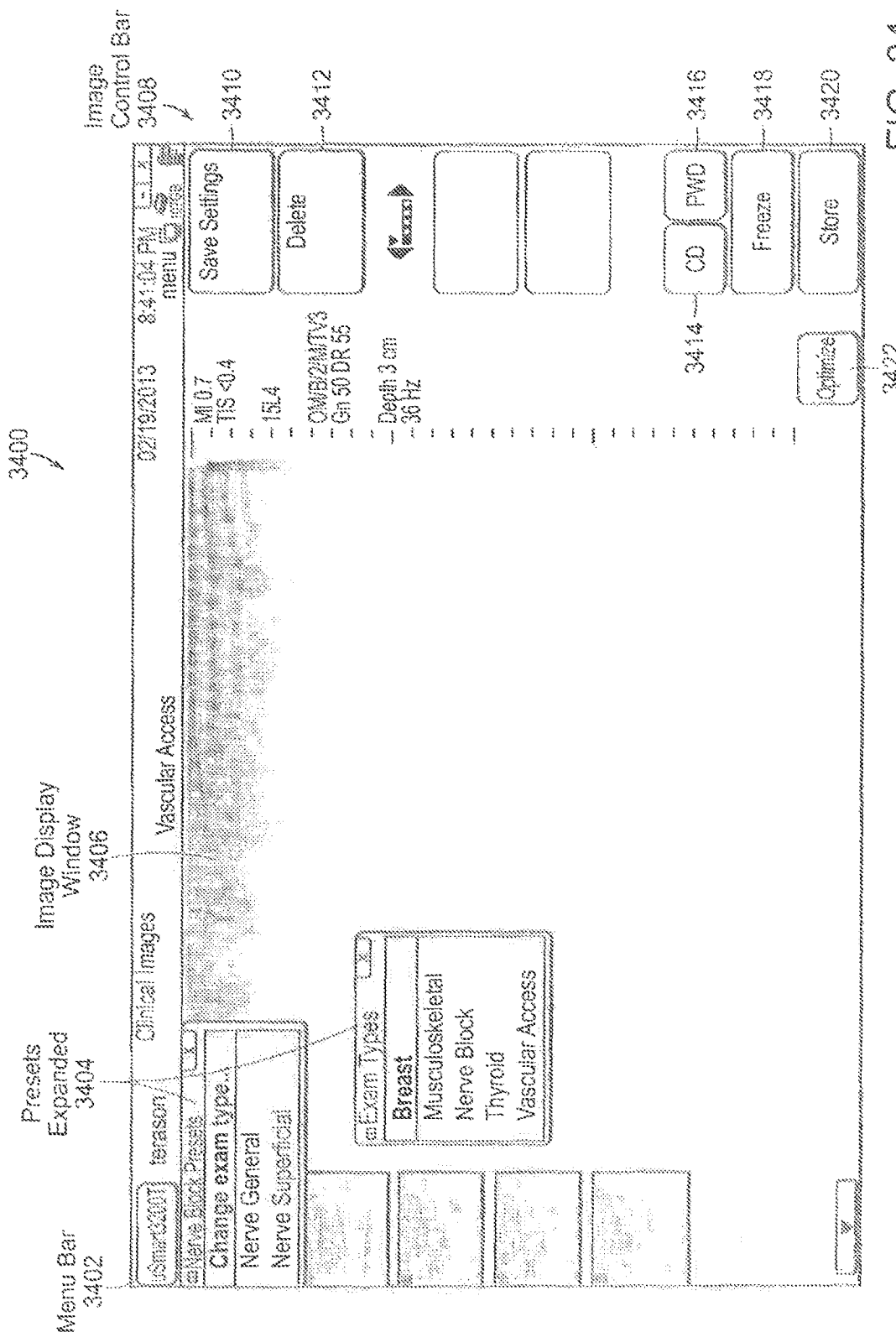
FIG. 34 illustrates a GUI Pre-sets Screen Interface for a user mode of operation with a modular ultrasound imaging system in accordance with the invention.

FIG. 34 illustrates a GUI patient data screen interface 3400, for a user mode of operation with a modular ultrasound imaging system in accordance with the invention. The screen interface for a user mode of operation 3400, may be displayed when the pre-sets selection mode 3404, is triggered from the menu bar 3402, when the ultrasound system is started.

Within the pre-sets screen 3400, the image control bar 3408, includes touch controls that may be operated by touch and touch gestures applied by the user directly to the surface of the display. Exemplary touch controls may include, but are not limited to a save settings touch control 3410, a delete touch control 3412, CD touch control 3414, PWD touch control 3416, a freeze touch control 3418, a store touch control 3420, and a optimize touch control 3422.

Figure 35:
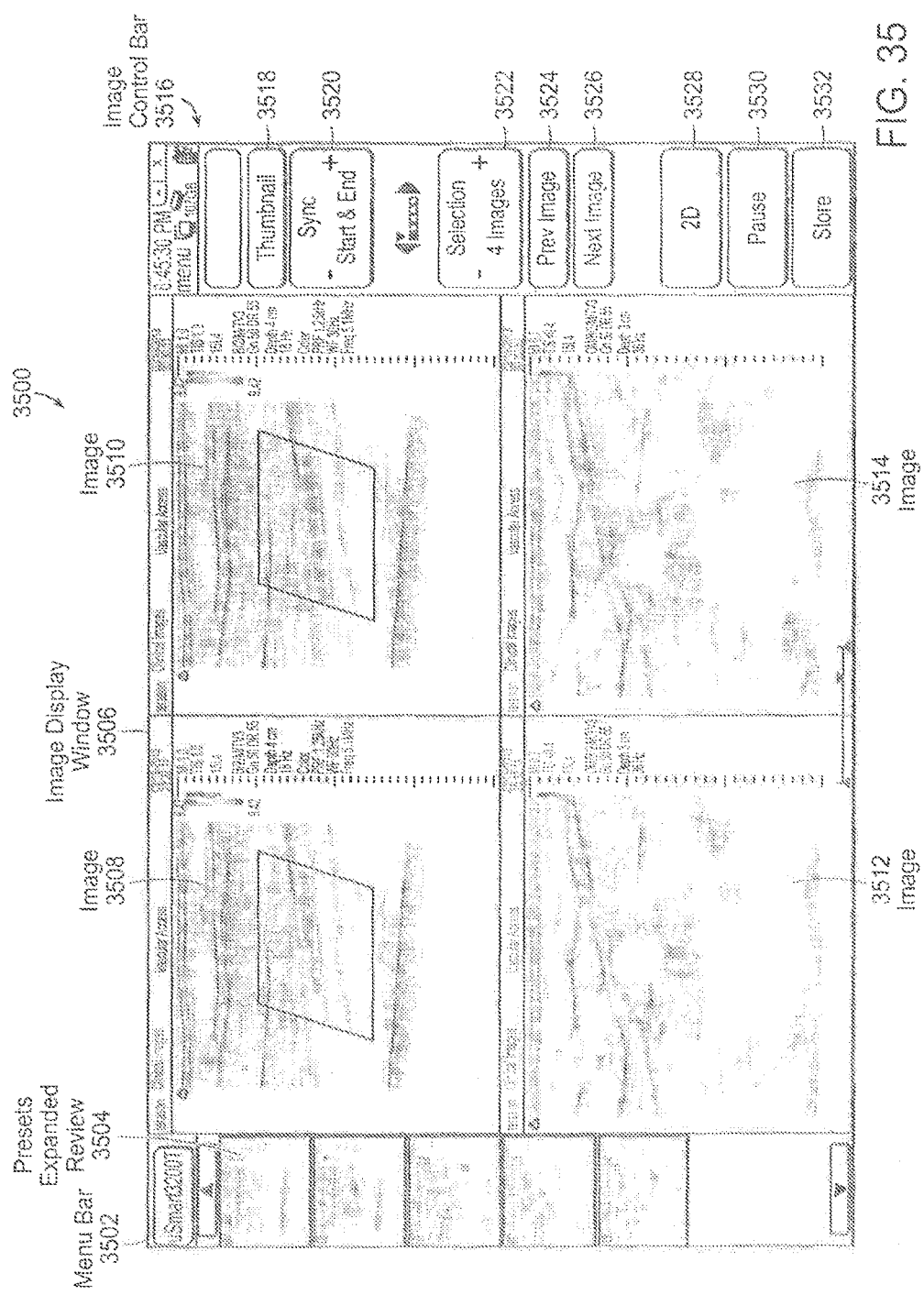
FIG. 35 illustrates a GUI Review Screen Interface for a user mode of operation with a modular ultrasound imaging system in accordance with the invention.

FIG. 35 illustrates a GUI review screen interface 3500, for a user mode of operation, with a modular ultrasound imaging system in accordance with the invention. The screen interface for a user mode of operation 3500, may be displayed when the pre-sets expanded review 3504, selection mode 3404, is triggered from the menu bar 3502, when the ultrasound system is started.

Within the review screen 3500, the image control bar 3516, includes touch controls that may be operated by touch and touch gestures applied by the user directly to the surface of the display. Exemplary touch controls may include, but are not limited to a thumbnail settings touch control 3518, sync touch control 3520, selection touch control 3522, a previous image touch control 3524, a next image touch control 3526, a 2-dimensional image touch control 3528, a pause image touch control 3530, and a store image touch control 3532.

A image display window 3506, may allow the user to review images in a plurality of formats. Image display window 3506, may allow a user to view images 3508, 3510, 3512, 3514, in combination or subset or allow any image 3508, 3510, 3512, 3514, to be viewed individually. The image display window 3506, may be configured to display up to four images 3508, 3510, 3512, 3514, to be viewed simultaneously.

Figure 36:
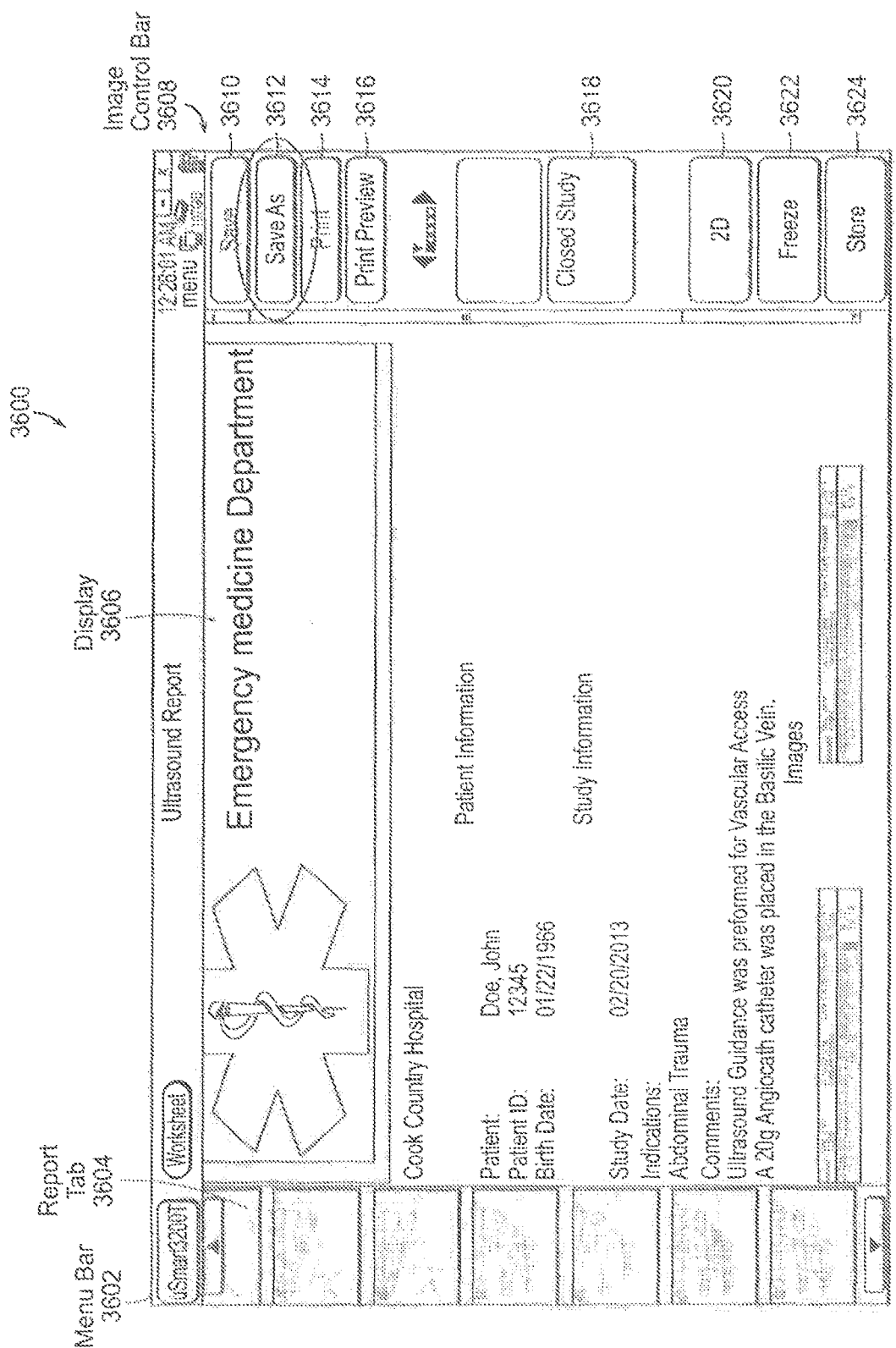
FIG. 36 illustrates a GUI Report Screen Interface for a user mode of operation with a modular ultrasound imaging system in accordance with the invention.

FIG. 36 illustrates a GUI Report Screen Interface for a user mode of operation with a modular ultrasound imaging system in accordance with the invention. The screen interface for a user mode of operation 3600, may be displayed when the report expanded review 3604, is triggered from the menu bar 3602, when the ultrasound system is started. The display screen 3606, contains the ultrasound report information 3626. The user may use the worksheet section within the ultrasound report 3626, to enter in comments, patient information and study information.

Within the report screen 3600, the image control bar 3608, includes touch controls that may be operated by touch and touch gestures applied by the user directly to the surface of the display. Exemplary touch controls may include, but are not limited to a save touch control 3610, a save as touch control 3612, a print touch control 3614, a print preview touch control 3616, a close study touch control 3618, a 2-dimensional image touch control 3620, a freeze image touch control 3622, and a store image touch control 3624.

Figure 37A:
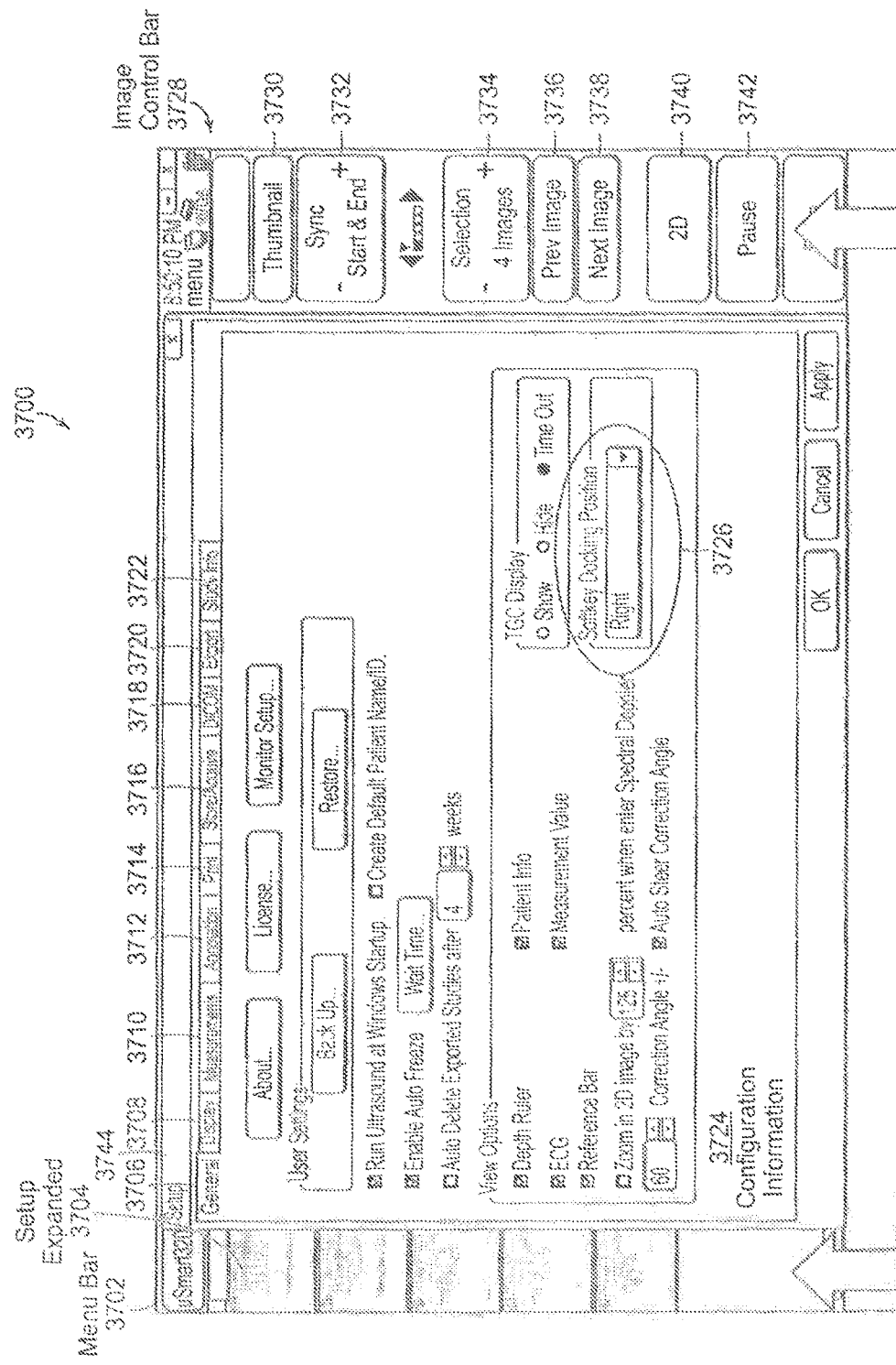
FIGS. 37A-37C illustrates a GUI Setup Display Screen Interface for a user mode of operation with a modular ultrasound imaging system in accordance with the invention.

FIG. 37 illustrates a GUI Setup Screen Interface for a user mode of operation with a modular ultrasound imaging system in accordance with the invention. The screen interface for a user mode of operation 3700, may be displayed when the report expanded review 3704, is triggered from the menu bar 3702, when the ultrasound system is started.

Figure 37B:
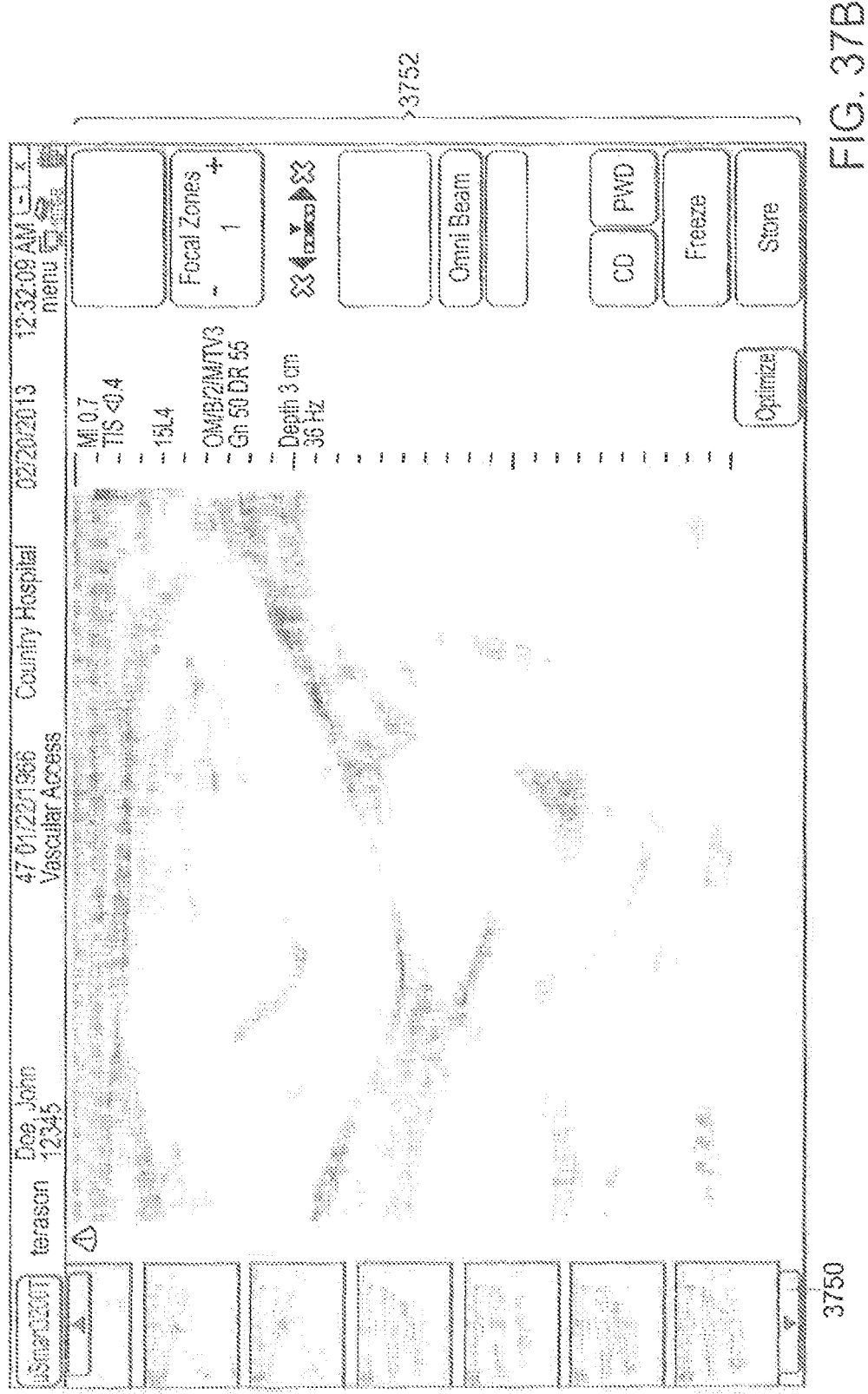
Figure 37C:
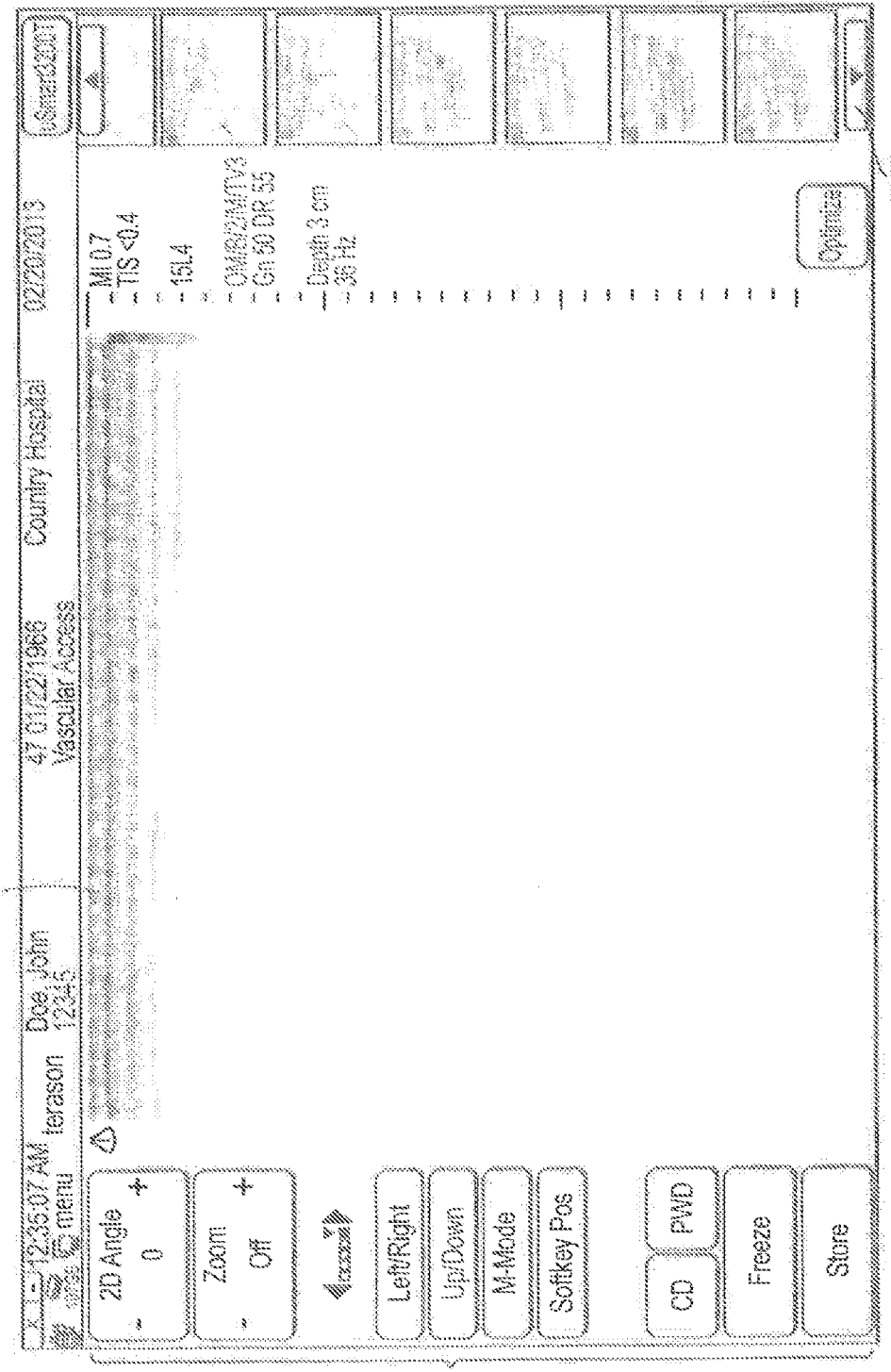

Within the setup expanded screen 3704, the setup control bar 3744, includes touch controls that may be operated by touch and touch gestures, applied by the user directly to the surface of the display. Exemplary touch controls may include, but are not limited to a general touch control 3706, a display touch control 3708, a measurements touch control 3710, annotation touch control 3712, a print touch control 3714, a store/acquire touch control 3716, a DICOM touch control 3718, an export touch control 3720, and a study information image touch control 3722. The touch controls may contain a display screen that allow the user to enter configuration information. For example, the general touch control 3706, contains a configuration screen 3724, wherein the user may enter configuration information. Additionally, the general touch control 3706, contains a section allowing user configuration of the soft key docking position 3726. FIG. 37B depicts the soft key controls 3752, with a right side alignment. FIG. 37B further illustrates that activation of the soft key control arrow 3750, will change the key alignment to the opposite side, in this case, left side alignment. FIG. 37C depicts left side alignment of the soft key controls 3762, the user may activate an orientation change by using the soft key control arrow 3760, to change the position to right side alignment.

Within the review screen 3700, the image control bar 3728, includes touch controls that may be operated by touch and touch gestures applied by the user directly to the surface of the display. Exemplary touch controls may include but are not limited to, a thumbnail settings touch control 3730, sync touch control 3732, selection touch control 3734, a previous image touch control 3736, a next image touch control 3738, a 2-dimensional image touch control 3740, and a pause image touch control 3742.

Figure 38:
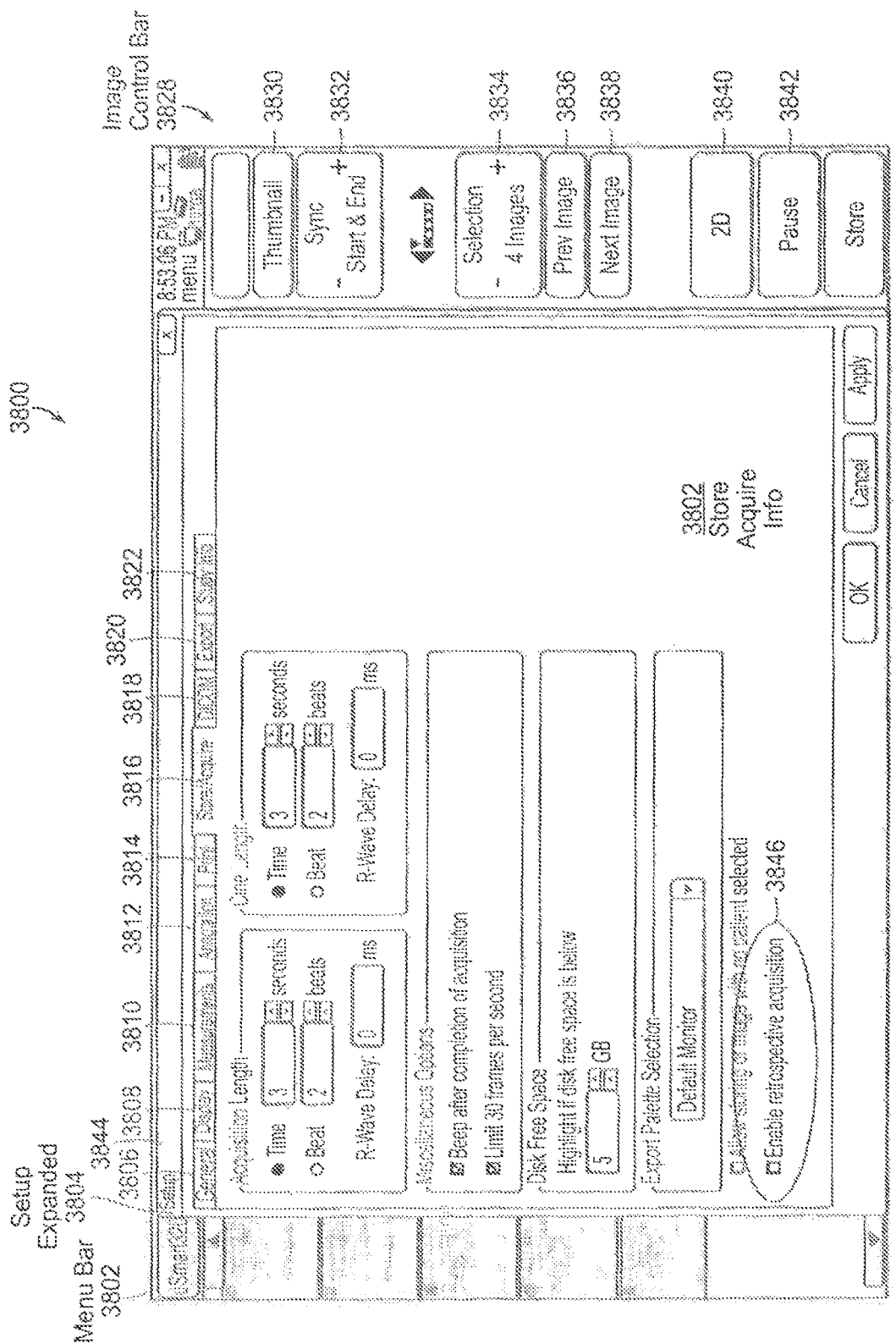
FIG. 38 illustrates a GUI Setup Store/Acquire Screen Interface for a user mode of operation with a modular ultrasound imaging system in accordance with the invention.

FIG. 38 illustrates a GUI Setup Screen Interface for a user mode of operation with a modular ultrasound imaging system in accordance with the invention. The screen interface for a user mode of operation 3800, may be displayed when the report expanded review 3804, is triggered from the menu bar 3802, when the ultrasound system is started.

Within the setup expanded screen 3804, the setup control bar 3844, includes touch controls that may be operated by touch and touch gestures applied by the user directly to the surface of the display. Exemplary touch controls may include, but are not limited to a plurality of icons such as a general touch control 3806, a display touch control 3808, a measurements touch control 3810, annotation touch control 3812, a print touch control 3814, a store/acquire touch control 3816, a DICOM touch control 3818, an export touch control 3820, and a study information image touch control 3822. The touch controls can contain a display screen that allow the user to enter store/acquire information. For example, the store/acquire touch control 3816, contains a configuration screen 3802, wherein the user may enter configuration information. The user can actuate a virtual keyboard allowing the user to enter alphanumeric characters in different touch activated fields. Additionally, the store/acquire touch control 3802, contains a section allowing user enablement of retrospective acquisition 3804. When the user enables the store function, the system is defaulted to store prospective cine loops. If the user enables the enable retrospective capture, the store function may collect the cine loop retrospectively.

Within the setup screen 3800, the image control bar 3828, includes touch controls that may be operated by touch and touch gestures applied by the user directly to the surface of the display. Exemplary touch controls may include, but are not limited to a thumbnail settings touch control 3830, synchronize touch control 3832, selection touch control 3834, a previous image touch control 3836, a next image touch control 3838, a 2-dimensional image touch control 3840, and a pause image touch control 3842.

Figure 39A:
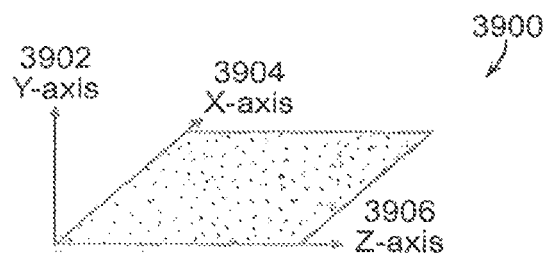
FIGS. 39A-39C illustrate XY bi-plane probe comprising a two one-dimensional, ID multi-element arrays in accordance with a preferred embodiment of the invention.
Figure 39B:
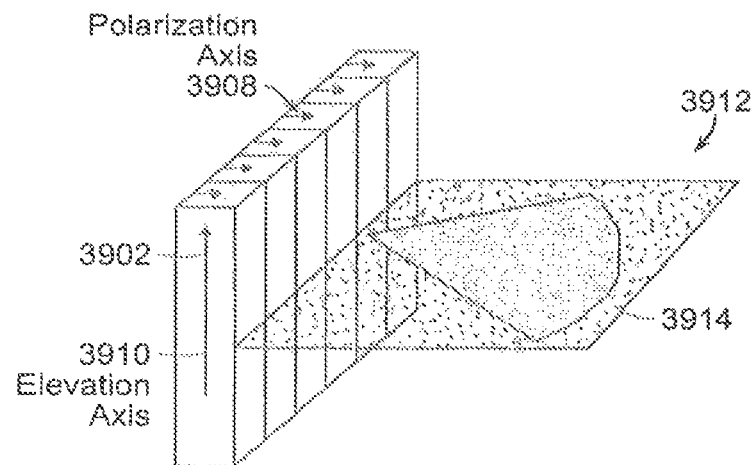

FIGS. 39A and 39B illustrate an XY bi-plane probe consisting of two one dimensional, multi-element arrays. The arrays may be constructed where one array is on top of the other with a polarization axis of each array being aligned in the same direction. The elevation axis of the two arrays can be at a right angle or orthogonal to one another. Exemplary embodiments can employ transducer assemblies such as those described in U.S. Pat. No. 7,066,887, the entire contents of which is incorporated herein by reference, or transducers sold by Vernon of Tours Cedex, France, for example. Illustrated by FIG. 39A, the array orientation is represented by arrangement 3900. The polarization axis 3908, of both arrays are pointed in the z-axis 3906. The elevation axis of the bottom array, is pointed in y-direction 3902, and the elevation axis of the top array, is in the x-direction 3904.

Figure 39C:
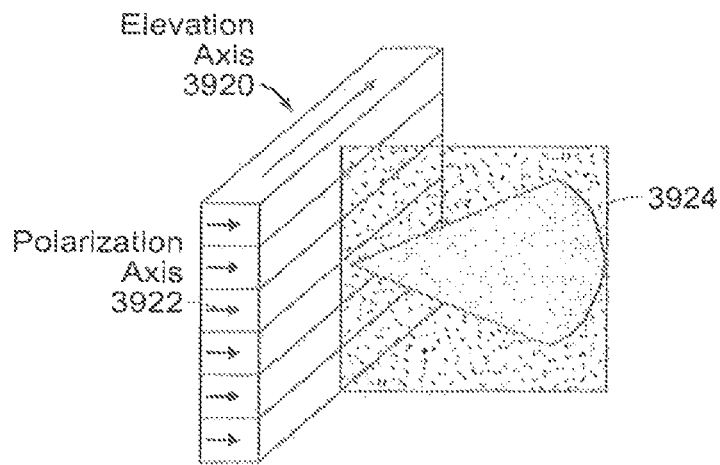

Further illustrated by FIG. 39B, a one dimensional multi-element array forms an image as depicted in arrangement 3912. A one-dimensional array with an elevation axis 3910, in a y-direction 3914, forms the ultrasound image 3914, on the x-axis 3904, z-axis 3906, plane. A one-dimensional array with the elevation axis 3910, in the x-direction 3904, forms the ultrasound image 3914, on the y-axis 3902, z-axis 3906. A one dimensional transducer array with elevation axis 3910, along a y-axis 3902, and polarization axis 3908, along a z-axis 3906, will result in a ultrasound image 3914, formed along the x 3904 and the z 3906 plane. An alternate embodiment illustrated by FIG. 39C depicts a one-dimensional transducer array with an elevation axis 3920, in a x-axis 904, and a polarization axis 3922, in the z-axis 3906, direction. The ultrasound image 3924, is formed on the y 3902 and the z 3906 plane.

Figure 40:
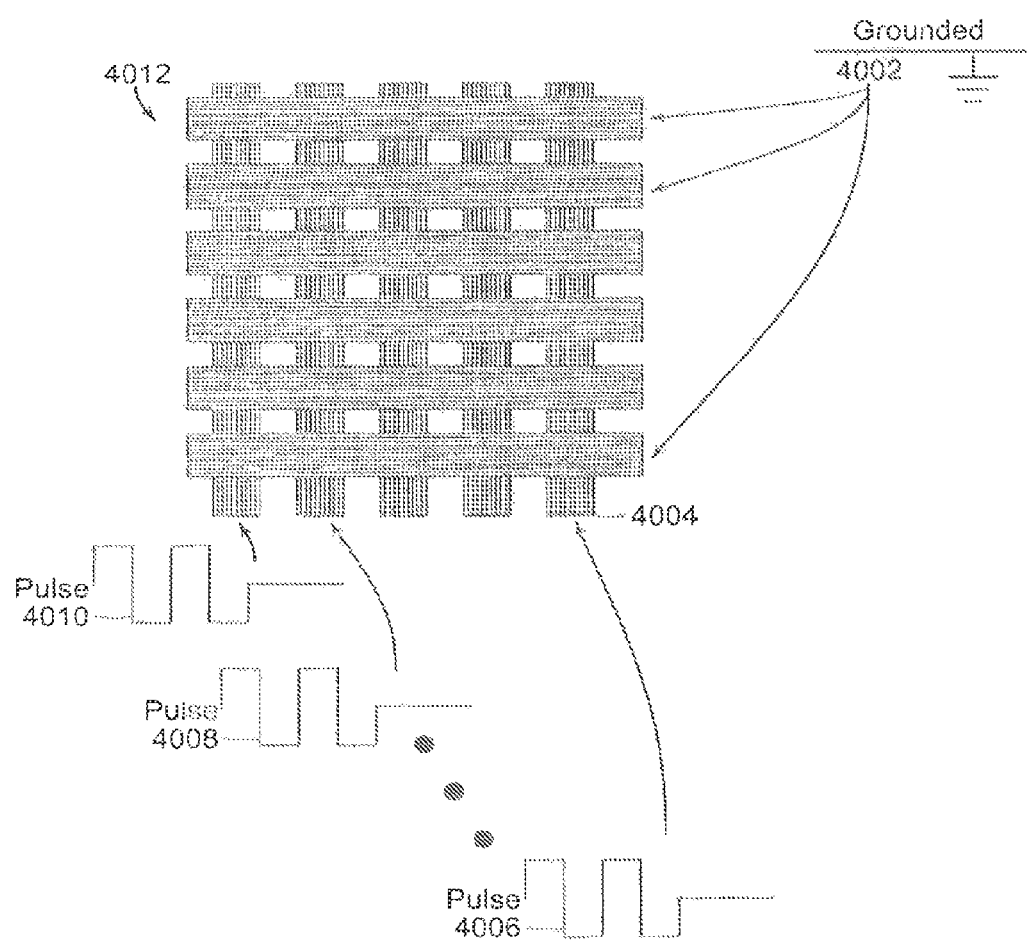
FIG. 40 illustrates the operation of a bi-plane image forming xy-probe.

FIG. 40 illustrates the operation of a bi-plane image forming xy-probe where array 4012 has a high voltage applied for forming images. High voltage driving pulses 4006, 4008, 4010, may be applied to the bottom array 4004, with a y-axis elevation. This application may result in generation of transmission pulses for forming the received image on the XZ plane, while keeping the elements of the top array 4002 at a grounded level. Such probes enable a 3D imaging mode using simpler electronics than a full 2D transducer array. A touchscreen activated user interface as described herein can employ screen icons and gestures to actuate 3D imaging operations. Such imaging operations can be augmented by software running on the tablet data processor that processes the image data into 3D ultrasound images. This image processing software can employ filtering smoothing and/or interpolation operations known in the art. Beamsteering can also be used to enable 3D imaging operations. A preferred embodiment uses a plurality of 1D sub-array transducers arranged for bi plane imaging.

Figure 41:
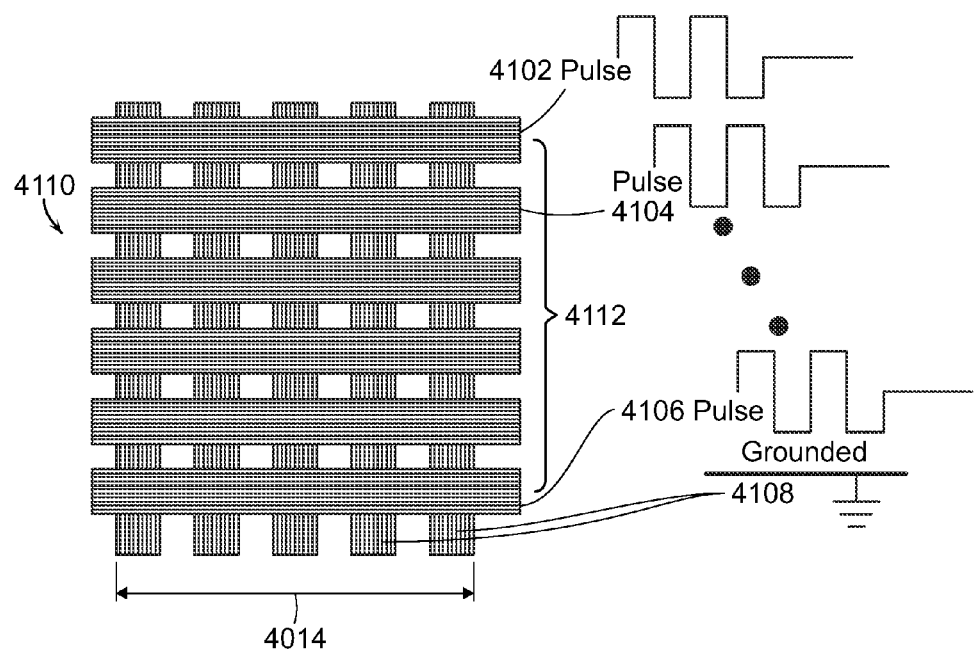
FIG. 41 illustrates the operation of a bi-plane image forming xy-probe.

FIG. 41 illustrates the operation of a bi-plane image forming xy-probe. FIG. 41 illustrates a array 4110, that has a high voltage applied to it for forming images. High voltage pulses 4102, 4104, 4106, may be applied to the top array 4112, with elevation in the x-axis, generating transmission pulses for forming the received image on the yz-plane, while keeping the elements of the bottom array 4014, grounded 4108. This embodiment can also utilize orthogonal 1D transducer arrays operated using sub-array beamforming as described herein.

Figure 42:
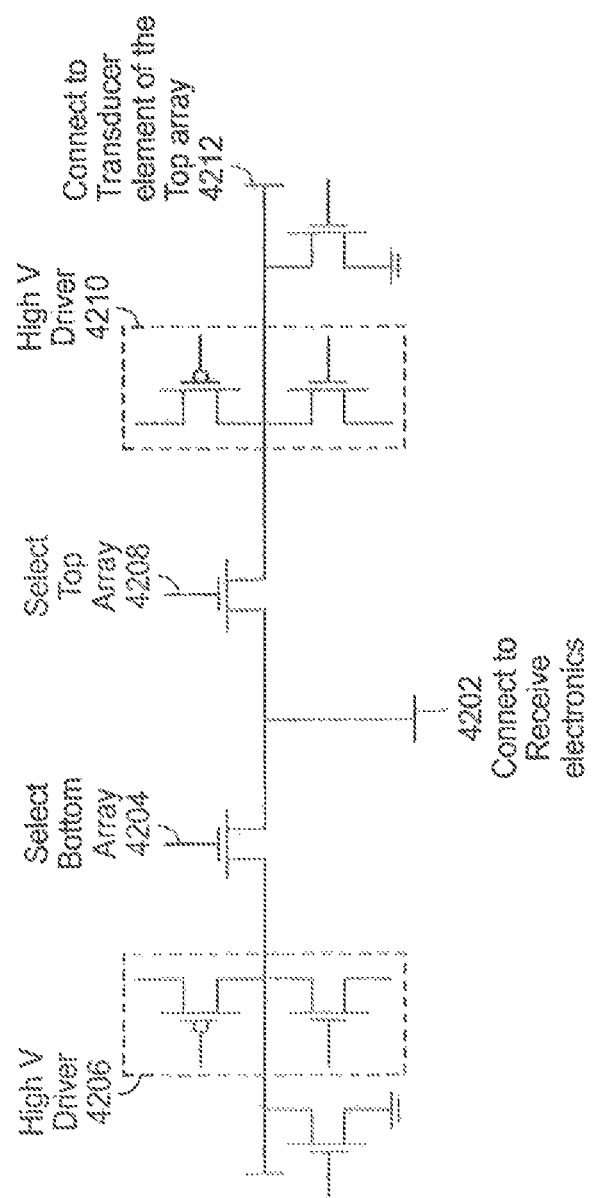
FIG. 42 illustrates a high voltage driver circuit for a bi-plane image forming xy-probe.

FIG. 42 illustrates the circuit requirements of a bi-plane image forming xy-probe. The receive beamforming requirements are depicted for a bi-plane probe. A connection to receive the electronics 4202, is made. Then elements from the select bottom array 4204, and select top array 4208, are connected to share one connect to the receive electronics 4202 channel. A two to one mux circuit can be integrated on the high voltage driver 4206, 4210. The two to one multiplexor circuit can be integrated into high voltage driver 4206, 4212. One receive beam is formed for each transmit beam. The bi-plane system requires a total of 256 transmit beams for which 128 transmit beams are used for forming a XZ-plane image and the other 128 transmit beams are used for forming a YZ-plane image. A multiple-received beam forming technique can be used to improve the frame rate. An ultrasound system with dual received beam capabilities for each transmit beam provides a system in which two received beams can be formed. The bi-plane probe only needs a total of 128 transmit beams for forming the two orthogonal plane images, in which 64 transmit beams are used to form a XZ-plane image with the other 64 transmit beams for the YZ-plane image. Similarly, for an ultrasound system with a quad or 4 receive beam capability, the probe requires 64 transmit beams to form two orthogonal-plane images.

Figure 43A:
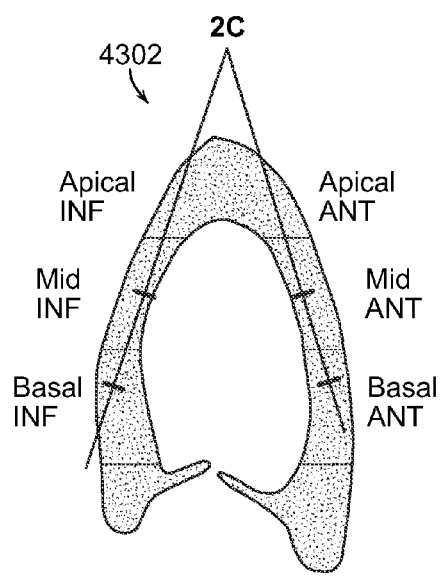
FIGS. 43A-43B illustrate simultaneous bi-plane evaluation of left ventricular condition.
Figure 43B:
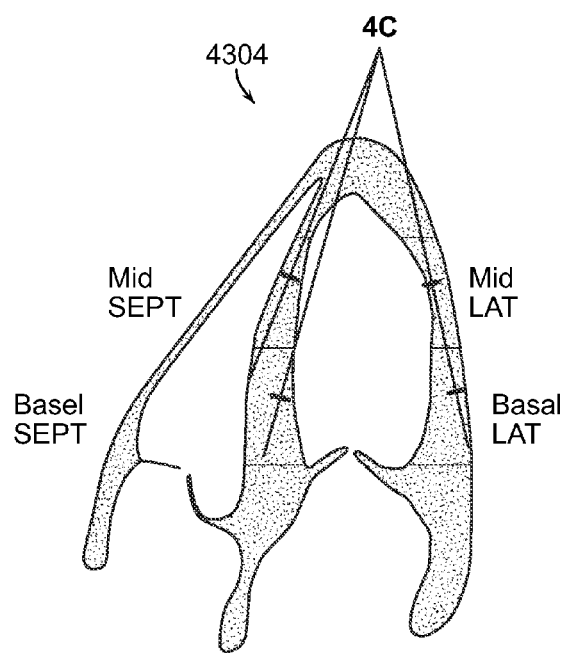

FIGS. 43A-43B illustrate an application for simultaneous bi-plane evaluation. The ability to measure the LV mechanical dyssynchrony with echocardiograph can help identify patients that are more likely to benefit from Cardiac Resynchronization Therapy. LV parameters needed to be quantified are Ts-(lateral-septal), Ts-SD, Ts-peak, etc. The Ts-(lateral-septal) can be measured on a 2D apical 4-chamber view Echo image, while the Ts-SD, Ts-peak (medial), Ts-onset (medial), Ts-peak(basal), Ts-onset (basal) can be obtained on two separated parasternal short-axis views with 6 segments at the level of mitral valve and at the papillary muscle level, respectively, providing a total of 12 segments. FIG. 43A-43B depicts an xy-probe providing apical four chamber 4304, and apical two chamber 4302 images, to be viewed simultaneously.

Figure 44A:
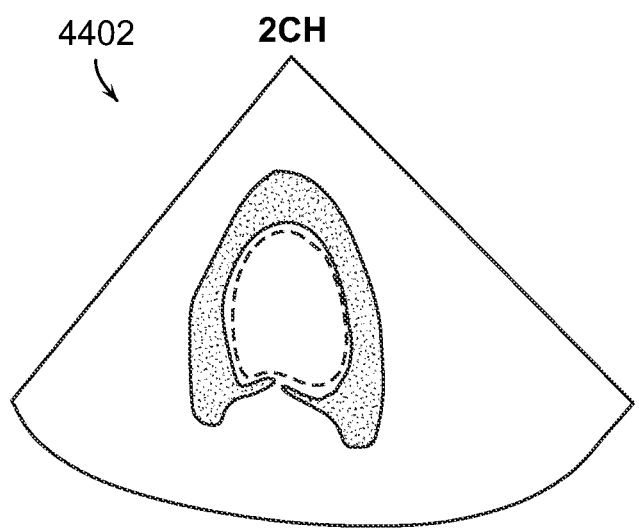
FIGS. 44A-44B illustrate ejection fraction probe measurement techniques in accordance with preferred embodiments of the invention.
Figure 44B:
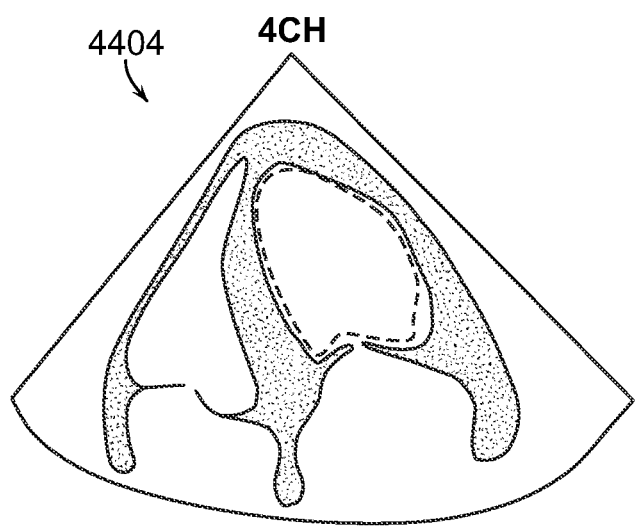

FIGS. 44A-44B illustrate ejection fraction probe measurement techniques. The biplane-probe provides for EF measurement, as visualization of two orthogonal planes ensure on-axis views are obtained. Auto-border detection algorithm, provides quantitative Echo results to select implant responders and guide the AV delay parameter setting. As depicted in FIG. 44 A XY probe acquires real-time simultaneous images from two orthogonal planes and the images 4402, 4404 are displayed on a split screen. A manual contour tracing or automatic boarder tracing technique can be used to trace the endocardial boarder at both end-systole and end-diastolic time from which the EF is calculated. The LV areas in the apical 2CH 4402, and 4CH 4404, views, A1 and A2 respectively, are measured at the end of diastole and the end of systole. The LVEDV, left ventricular end-diastolic volume, and LVESV, left ventricular the end-systole volume, are calculated using the formula:

$$V = \frac{8}{3\pi} \frac{A_1 A_2}{L}.$$

And the ejection fraction is calculated by $$EF = \frac{LVEDV - LVESD}{LVEDV}.$$

It is noted that the operations described herein are purely exemplary, and imply no particular order. Further, the operations can be used in any sequence, when appropriate, and/or can be partially used. Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2, etc., or by rounded-off approximations thereof, unless otherwise specified.

With the above illustrative embodiments in mind, it should be understood that such embodiments can employ various computer-implemented operations involving data transferred or stored in computer systems. Such operations are those requiring physical manipulation of physical quantities. Typically, though not necessarily, such quantities take the form of electrical, magnetic, and/or optical signals capable of being stored, transferred, combined, compared, and/or otherwise manipulated.

Further, any of the operations described herein that form part of the illustrative embodiments are useful machine operations. The illustrative embodiments also relate to a device or an apparatus for performing such operations. The apparatus can be specially constructed for the required purpose, or can incorporate general-purpose computer devices selectively activated or configured by a computer program stored in the computer. In particular, various general-purpose machines employing one or more processors coupled to one or more computer readable media can be used with computer programs written in accordance with the teachings disclosed herein, or it may be more convenient to construct a more specialized apparatus to perform the required operations.

The foregoing description has been directed to particular illustrative embodiments of this disclosure. It will be apparent, however, that other variations and modifications may be made to the described embodiments, with the attainment of some or all of their associated advantages. Moreover, the procedures, processes, and/or modules described herein may be implemented in hardware, software, embodied as a computer-readable medium having program instructions, firmware, or a combination thereof. For example, one or more of the functions described herein may be performed by a processor executing program instructions out of a memory or other storage device.

It will be appreciated by those skilled in the art that modifications to and variations of the above-described systems and methods may be made without departing from the inventive concepts disclosed herein. Accordingly, the disclosure should not be viewed as limited except as by the scope and spirit of the appended claims.

The invention claimed is:

1. A handheld medical ultrasound imaging device comprising:
    a transducer probe housing a transducer array; and
    a tablet housing powered by a battery, the housing having a front panel, a computer in the tablet housing, the computer including at least one processor and at least one memory, a touch screen display that displays an ultrasound image and a graphical user interface having a plurality of touch actuated icons, the touch screen display positioned on the front panel, and an ultrasound beamformer processing circuit disposed in the tablet housing that receives image signals from the transducer array, the touch screen display and the ultrasound beamformer processing circuit being communicably connected to the computer, the computer being configured to respond to a first input from the touch screen display to alter an operation of the ultrasound beamformer processing circuit to display an ultrasound image, a second input from the touch screen display actuating a needle guide operation such that a needle can be visualized with an image on the touch screen display, a third input from the touch screen display that actuates an imaging depth control adjustment with a touch gesture, and a fourth input from the touch screen display that actuates split screen viewing of the ultrasound image and a second diagnostic image on the touch screen display.

2. The device of claim 1 wherein the first input corresponds to a moving gesture on the touch screen display.

3. The device of claim 1 wherein the transducer array comprises a bi plane transducer array.

4. The device of claim 3 further comprising a second input that includes a double tap gesture against the touch screen display.

5. The device of claim 3 further comprising in response to the second input from the touch screen display, displaying a first cursor inside a region of a virtual window displaying a magnified image.

6. The device of claim 5 further comprising receiving, at the computer, a fifth input from the touch screen display, the fifth input being received inside the region of the virtual window.

7. The device of claim 6 wherein the fifth input corresponds to a drag gesture on the touch screen display.

8. The device of claim 6 further comprising in response to the fifth input from the touch screen display, moving the first cursor to a first location inside the region of the virtual window.

9. The device of claim 8 further comprising receiving, at the computer, a sixth input from the touchscreen display, the sixth input being received at the first location inside the region of the virtual window.

10. The device of claim 6 further comprising in response to the fifth input from the touch screen display, fixing the first cursor at the first location inside the region of the virtual window.

11. The device of claim 10 further comprising performing, by the computer, at least one measurement on the ultrasound image based at least in part on the first cursor at the first location.

12. The device of claim 1 further comprising a further input that corresponds to a double tap gesture against the touchscreen display.

13. The device of claim 10 wherein the computer receives a further input from the touchscreen display, the further input being received inside the region of the virtual window.

14. The device of claim 13 wherein the further input corresponds to a press and drag gesture against the touch screen display.

15. The device of claim 13 further comprising in response to the further input from the touch screen display connecting a line on the touch screen display extending from the first cursor across at least a portion of the ultrasound image to a second location inside the region of the virtual window.

16. The device of claim 1 wherein the wherein the housing has a volume of less than 2500 cubic centimeters.

17. The device of claim 1 wherein the housing is connected to a stand.

18. The device of claim 17 wherein the stand rotates relative to the housing.

19. The device of claim 1 wherein the housing mounts on a cart.

20. The device of claim 1 wherein a multiplexor on the cart can electrically connect to the tablet housing to connect to a plurality of transducer arrays.

21. The device of claim 17 wherein the housing docks with the stand.

22. The device of claim 21 wherein the stand housing is electrically connected to the stand and wherein the stand has external communication parts.

23. The device of claim 20 wherein the multiplexor can be switched using a touch gesture.

24. The device of claim 1, wherein the ultrasound image includes an image of a portion of a patient's body.

25. The device of claim 1, further comprising a needle guide to position the needle with respect to a portion of the patient's body.

26. The device of claim 1, wherein the touch screen display further displays a visualization of the needle in a split screen format.

27. The device of claim 1, wherein the touch screen further displays an image of the needle within a patient's body.

28. The device of claim 1, wherein the touch screen display further displays at least one needle visualization touch control.

29. The device of claim 1, wherein the at least one needle visualization touch control is configured to guide the needle during a needle injection.

30. The device of claim 1, wherein the at least one needle visualization touch control includes controlling the dynamic range or performing a desired map operation.

31. The device of claim 1, wherein the at least one needle visualization touch control includes at least one of a press gesture, or a press and drag gesture.

32. The device of claim 1, further comprising a needle position sensing system.

33. The device of claim 32, wherein the needle position sensing system includes a passive ultrasound transducer element.

34. The device of claim 32, wherein the needle position sensing system includes at least one ultrasound transducer element operatively coupled to a needle guide.

35. The device of claim 32, wherein the needle position sensing system includes an ultrasound imaging probe assembly.

36. The device of claim 1, further comprising a needle guide mounted to the ultrasound imaging probe assembly via a needle guide mounting bracket.

37. The device of claim 32, wherein the needle position sensing system includes an ultrasound reflector configured to reflect ultrasonic waves.

38. The device of claim 37, wherein the ultrasound reflector is operatively coupled to the needle.

39. The device of claim 37, wherein the ultrasound reflector is operatively coupled to an exposed end of the needle.

40. The device of claim 37, wherein a position of the ultrasound reflector is determined by transmitting an ultrasonic wave from a transducer element on a needle guide.

41. The device of claim 37, wherein the ultrasound reflector is configured to reflect the ultrasonic wave back to the transducer element.

42. The device of claim 37, wherein a distance between the ultrasound reflector and the transducer element is calculated based on a time delay of the reflected ultrasonic wave.

43. The device of claim 32, wherein the needle position sensing system includes a needle guide and transducer elements enclosed in an enclosure of an imaging probe.

44. The device of claim 32, wherein the needle position sensing system includes a linear ultrasound array mounted substantially parallel to a direction of movement of the needle.

45. A method of operating a handheld medical ultrasound imaging device, the medical ultrasound imaging device comprising a transducer probe, a tablet housing, the tablet housing having a front panel, a computer in the housing, the computer including at least one processor and at least one memory, a touch screen display that displays an ultrasound image, the image being adjustable in response to an imaging depth control touch gesture and that displays a split screen icon such that the touch screen can operate in a split screen format to display the ultrasound image and a second diagnostic image, the touch screen display positioned on the front panel, and an ultrasound beamformer processing circuit disposed in the tablet housing that is powered by a battery, the touch screen display and the ultrasound beamformer processing circuit being communicably coupled to the computer, the method comprising the steps of:
receiving, at the computer, a first input from the touch screen display to actuate a needle guide operation; and
in response to a second input from the touch screen display, operating the ultrasound beamformer processing circuit to image a needle inserted into a patient.

46. The method of claim 45 further comprising a further input corresponding to a moving gesture on the touch screen display.

47. The method of claim 45 further comprising receiving, at the computer, a third input from the touch screen display that corresponds to a double tap gesture against the touch screen display.

48. The method of claim 45 wherein a third input corresponds to a drag gesture on the touch screen display.

49. The method of claim 48 further comprising in response to the third input from the touch screen display, moving the first cursor to a first location inside the region of a virtual window.

50. The method of claim 49 further comprising receiving, at the computer, a fourth input from the touchscreen display, the fourth input being received at the first location inside the region of the virtual window.

51. The method of claim 45 wherein a third input corresponds to a press gesture against the touch screen display.

52. The method of claim 45 further comprising receiving, at the computer, a second further input from the touchscreen display, the second further input being received substantially simultaneously with the further input.

53. The method of claim 45 wherein the second further input corresponds to a tap gesture against the touchscreen display.

54. The method of claim 45 wherein a third input corresponds to a double tap gesture against the touchscreen display.

55. The method of claim 54 further comprising in response to the third further input from the touch screen display, displaying a second cursor at a second location inside the region of a virtual window.

56. The method of claim 55 further comprising performing, by the computer, at least one measurement on the ultrasound image based at least in part on the respective locations of the first and second cursors inside the region of the virtual window.

57. The method of claim 55 further comprising receiving, at the computer, a fourth further input from the touch screen display, the fourth further input being received inside the region of the virtual window.

58. The method of claim 57 wherein the fourth further input corresponds to a press and drag gesture against the touch screen display.

59. The method of claim 57 further comprising in response to the fourth further input from the touch screen display, providing a connecting line on the touch screen display extending from the first cursor across at least a portion of the ultrasound image to a second location inside the region of the virtual window.

* * * * *